US007527973B2

(12) United States Patent
Diamond et al.

(10) Patent No.: US 7,527,973 B2
(45) Date of Patent: May 5, 2009

(54) ANTIBODIES AGAINST WEST NILE VIRUS AND THERAPEUTIC AND PROPHYLACTIC USES THEREOF

(75) Inventors: Michael Diamond, St. Louis, MO (US); Theodore Oliphant, St. Louis, MO (US); Christopher Michael Doane, New Albany, IN (US)

(73) Assignee: Washington University, St. Louis, MO (US)

( * ) Notice: Subject to any disclaimer, the term of this patent is extended or adjusted under 35 U.S.C. 154(b) by 245 days.

(21) Appl. No.: 11/159,046

(22) Filed: Jun. 21, 2005

(65) Prior Publication Data

US 2006/0067940 A1 Mar. 30, 2006

Related U.S. Application Data

(60) Provisional application No. 60/581,819, filed on Jun. 21, 2004.

(51) Int. Cl.
*C12N 5/06* (2006.01)
*C12N 5/10* (2006.01)
*C12P 21/01* (2006.01)
*A61K 49/00* (2006.01)
*A61K 39/395* (2006.01)
*A61K 39/42* (2006.01)
*A61K 39/12* (2006.01)
*A61K 39/193* (2006.01)

(52) U.S. Cl. .................... 435/331; 435/70.21; 435/326; 435/328; 435/339; 435/354; 424/9.2; 424/141; 424/147.1; 424/218.1

(58) Field of Classification Search ........................ None
See application file for complete search history.

(56) References Cited

U.S. PATENT DOCUMENTS

2003/0148261 A1* 8/2003 Fikrig et al. .................... 435/5
2006/0067940 A1 3/2006 Diamond et al.
2006/0115837 A1 6/2006 Fremont et al.

OTHER PUBLICATIONS

Beasley et al. Journal of Virology, Dec. 2002, vol. 76, No. 24, pp. 13097-13100. See IDS Apr. 25, 2008 p. 1.*
Roehrig et al. Annals of the New York Academy of Sciences, Dec. 2001, vol. 951, pp. 286-297. See IDS Apr. 25, 2008, p. 6.*
Agrawal et al., 2003, "Human immunoglobulin as a treatment for West Nile virus infection," J. Infect. Dis. 188(1) :1-4, University of Chicago Press, Chicago, IL.
Allison et al., 1999, "Mapping of functional elements in the stem-anchor region of tick-borne encephalitis virus envelope protein E," J. Virol. 73(7):5605-12, American Society for Microbiology, Washington, DC.
Anderson et al., 2002, "Efficacy of interferon alpha-2b and ribavirin against West Nile virus in vitro," Emerg. Infect. Dis. 8(1):107-8.
Asnis et al., 2000, "The West Nile Virus outbreak of 1999 in New York: the Flushing Hospital experience," Clin. Infect. Dis. 30(3):413-8.
Beasley et al., 2001, "Epitopes on the dengue 1 virus envelope protein recognized by neutralizing IgM monoclonal antibodies," Virology 279(2):447-58, Academic Press, New York, NY.
Beasley et al, 2002, "Identification of neutralizing epitopes within structural domain III of the West Nile virus envelope protein," J. Virol. 76(24):13097-100; American Society for Microbiology, Washington, DC.
Ben-Nathan et al., 1996, "West Nile virus neuroinvasion and encephalitis induced by macrophage depletion in mice," Arch. Virol. 141(3-4):459-69, Springer-Verlag, Vienna, Austria.
Ben-Nathan et al., 2003, "Prophylactic and therapeutic efficacy of human intravenous immunoglobulin in treating West Nile virus infection in mice," J. Infect. Dis. 188(1):5-12, University of Chicago Press, Chicago, IL.
Brandriss et al., 1986, "Lethal 17D yellow fever encephalitis in mice. I. Passive protection by monoclonal antibodies to the envelope proteins of 17D yellow fever and dengue 2 viruses," J. Gen. Virol. 67 (Pt 2):229-34, Society for General Microbiology, London, England.
Broom et al., 2000, "Immunisation with gamma globulin to Murray Valley encephalitis virus and with an inactivated Japanese encephalitis virus vaccine as prophylaxis against Australian encephalitis: Evaluation in a mouse model," J. Med. Virol. 61:259-265, Wiley-Liss, New York.
Camenga et al., 1974, "Cyclophosphamide-potentiated West Nile viral encephalitis: relative influence of cellular and humoral factors," J. Infect. Dis. 130(6):634-41, University of Chicago Press, Chicago, IL.
Cardosa et al., 1986, "Interaction of West Nile virus with primary murine macrophages: role of cell activation and receptors for antibody and complement," J. Virol. 57(3):952-9, American Society for Microbiology, Washington, DC.
Cecilia et al., 1991, "Nucleotide changes responsible for loss of neuroinvasiveness in Japanese encephalitis virus neutralization-resistant mutants," Virology 181(1):70-7, Academic Press, New York, NY.
Chambers et al., 1990, "Flavivirus genome organization, expression, and replication," Annu. Rev. Microbiol. 44:649-88, Annual Reviews, Palo Alto, CA.

(Continued)

*Primary Examiner*—Bruce Campell
*Assistant Examiner*—Sharon Hurt
(74) *Attorney, Agent, or Firm*—Drinker Biddle & Reath LLP

(57) ABSTRACT

The present invention relates to compositions comprising antibodies or fragments thereof that immunospecifically bind to one or more antigens of a flavivirus, particularly of West Nile Virus (WNV), and methods for preventing, treating or ameliorating symptoms associated with a flavivirus, particularly of West Nile Virus (WNV), infection utilizing said compositions. In particular, the present invention relates to methods for preventing, treating or ameliorating symptoms associated with WNV infection, said methods comprising administering to a human subject an effective amount of one or more antibodies or fragments thereof that immunospecifically bind to a WNV antigen. The present invention also relates to detectable or diagnostic compositions comprising antibodies or fragments thereof that immunospecifically bind to a WNV antigen and methods for detecting or diagnosing WNV infection utilizing said compositions.

39 Claims, 21 Drawing Sheets

OTHER PUBLICATIONS

Figure 3:
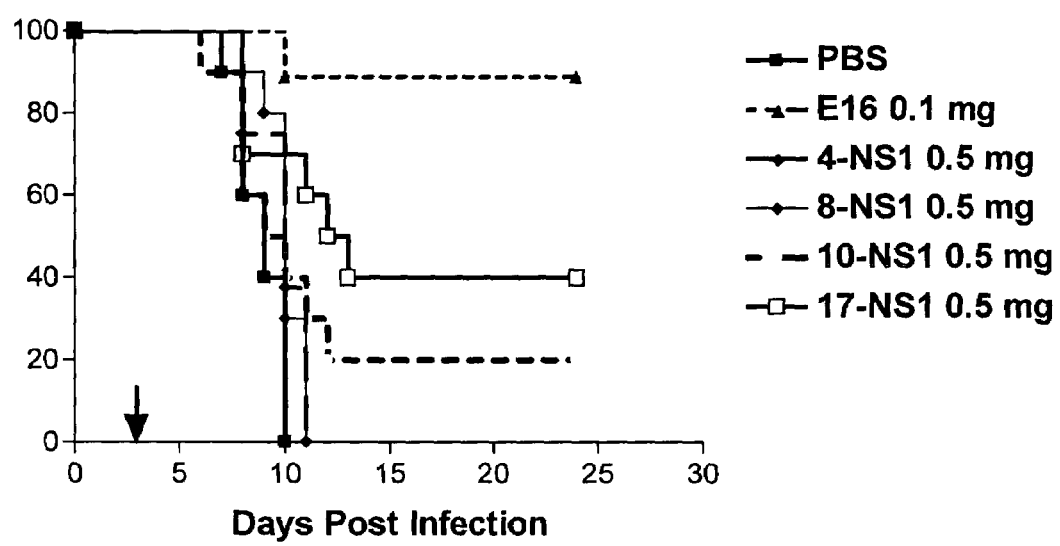

Chiba et al., 1999, "Protection against tick-borne encephalitis virus isolated in Japan by active and passive immunization," Vaccine 17(11-12):1532-9, Elsevier, Amsterdam, Holland.

Chu et al., 2005, "Inhibition of West Nile virus entry by using a recombinant domain III from the envelope glycoprotein," J. Gen. Virol. 86(Pt 2):405-12, Society for General Microbiology, London, England.

Crill et al., 2001, "Monoclonal antibodies that bind to domain III of dengue virus E glycoprotein are the most efficient blockers of virus adsorption to Vero cells," J. Virol. 75(16):7769-73, American Society for Microbiology, Washington, DC.

Diamond et al., 2000, "Infection of Human Cells by Dengue Virus Is Modulated by Different Cell Types and Viral Strains," J. Virol. 74:7814-7823, American Society for Microbiology, Washington, DC.

Diamond et al., 2003, "A critical role for induced IgM in the protection against West Nile virus infection," J. Exp. Med. 198(12):1853-62, Rockefeller Univ. Press, New York, NY.

Diamond et al., 2003, "B Cells and Antibody Play Critical Roles in the Immediate Defense of Disseminated Infection by West Nile Encephalitis Virus," 1. Virol. 77:2578-2586.

Diamond et al., 2003, "Innate and Adaptive Immune Responses Determine Protection against Disseminated Infection by West Nile Encephalitis Virus," Viral Immunol. 16(3):259-278.

Eisenstein, 2005, "Antibody neutralizes West Nile virus," Lab. Anim. (NY) 34(6):10.

Engle et al., 2003, "Antibody prophylaxis and therapy against West Nile virus infection in wild-type and immunodeficient mice," J. Virol. 77(24):12941-9, American Society for Microbiology, Washington, DC.

Falconar et al., 1999, "Identification of an epitope on the dengue virus membrane (M) protein defined by cross-protective monoclonal antibodies: design of an improved epitope sequence based on common determinants present in both envelope (E and M) proteins," Arch. Virol. 144(12):2313-30, Springer-Verlag, Vienna, Austria.

Goncalvez et al., 2004, "Chimpanzee Fab fragments and a derived humanized immunoglobulin G1 antibody that efficiently cross-neutralize dengue type 1 and type 2 viruses," J. Virol. 78(23):12910-8, American Society for Microbiology, Washington, DC.

Halevy et al., 1994, "Loss of active neuroinvasiveness in attenuated strains of West Nile virus: pathogenicity in immunocompetent and SCID mice," Arch. Virol. 137(3-4):355-70, Springer-Verlag, Vienna, Austria.

Haley et al., 2003, "The role for intravenous immunoglobulin in the treatment of West Nile virus encephalitis," Clin. Infect. Dis. 37(6):e88-90.

Halstead et al., 1980, "Enhancement of dengue virus infection in monocytes by flavivirus antisera," Am. J. Trop. Med. Hyg. 29 (4):638-42.

Halstead et al., 1989, "Antibody, macrophages, dengue virus infection, shock, and hemorrhage: a pathogenetic cascade," Rev. Infect. Dis. Suppl 4:S830-9.

Hamdan et al., 2002, "Possible benefit of intravenous immunoglobulin therapy in a lung transplant recipient with West Nile virus encephalitis," Transpl. Infect. Dis. 4(3):160-2.

Henchal et al., 1988, "Synergistic interactions of anti-NS1 monoclonal antibodies protect passively immunized mice from lethal challenge with dengue 2 virus," J. Gen. Virol. 69 (Pt 8):2101-7, Society for General Microbiology, London, England.

Holgate et al., 2001, "Efficacy of omalizumab, an anti-immunoglobulin E antibody, in patients with allergic asthma at high risk of serious asthma-related morbidity and mortality," Curr. Mud. Res. Opin. 17(4):233-40.

Julander et al., 2005, "Treatment of West Nile virus-infected mice with reactive immunoglobulin reduces fetal titers and increases dam survival," Antiviral Res. 65(2):79-85, Elsevier/North-Holland, Amsterdam, Holland.

Kimura-Kuroda et al., 1988, "Protection of mice against Japanese encephalitis virus by passive administration with monoclonal antibodies," J. Immunol. 141(10):3606-10, The American Association of Immunologists, Baltimore, MD.

Kishore et al., 2000, "C1q: structure, function, and receptors," Immunopharmacology 49(1-2):159-70.

Li et al., 2005, "Differential expression of domain III neutralizing epitopes on the envelope proteins of West Nile virus strains," Virology 335(1):99-105, Academic Press, New York, NY.

Lin et al., 1994, "Localization of a neutralizing epitope on the envelope protein of dengue virus type 2," Virology 202(2):885-90, Academic Press, New York, NY.

Mathews et al., 1984, "Elucidation of the topography and determination of the protective epitopes on the E glycoprotein of Saint Louis encephalitis virus by passive transfer with monoclonal antibodies," J. Immunol. 132:1533-1537, The American Association of Immunologists, Baltimore, MD.

Mehlop et al., 2005, "Complement activation is required for induction of a protective antibody response against West Nile virus infection," J. Virol. 79(12):7466-77, American Society for Microbiology, Washington, DC.

Miwa et al., 2002, "Crry, but not CD59 and DAF, is indispensable for murine erythrocyte protection in vivo from spontaneous complement attack," Blood 99(10):3707-16, Blood, Grune & Stratton, Washington, DC.

Nybakken et al., 2005, "Structural basis of West Nile virus neutralization by a therapeutic antibody," Nature, Sep. 2005, vol. 437, No. 29, pp. 764-768, Nature Publishing Group, London, England.

Oliphant et al., 2005, "Development of a humanized monoclonal antibody with therapeutic potential against West Nile virus," Nat. Med. 11(5):522-30.

Peiris et al., 1982, "Monoclonal antibodies against the flavivirus West Nile," J. Gen. Virol. 58(Pt 2):283-9, Society for General Microbiology, London, England.

Rager-Zisman et. al., 2003, "Efficacy of prophylactic and therapeutic human immunoglobulin on West Nile virus infection," Isr. Med. Assoc. J. 5(10):691.

Razumov et al., 2005, "Neutralizing monoclonal antibodies against Russian strain of the West Nile virus," Viral Immunol. 18(3):558-68.

Roehrig et al., 1983, "Identification of epitopes on the E glycoprotein of Saint Louis encephalitis virus using monoclonal antibodies," Virology 128(1):118-26, Academic Press, New York, NY.

Roehrig et al., 2001, "Antibody prophylaxis and therapy for flavivirus encephalitis infections," Ann. N. Y. Acad. Sci. 951:286-97.

Sanchez et al., 2005, "Characterization of neutralizing antibodies to West Nile virus," Virology 336(1):70-82, Academic Press, New York, NY.

Sawyer, 2000, "Antibodies for the prevention and treatment of viral diseases," Antiviral Res. 47(2):57-77, Elsevier/North-Holland, Amsterdam, Holland.

Schlesinger et al., 1993, "The Fc portion of antibody to yellow fever virus NS1 is a determinant of protection against YF encephalitis in mice," Virology 192(1):132-41, Academic Press, New York, NY.

Schlesinger et al., 1996, "Replication of yellow fever virus in the mouse central nervous system: comparison of neuroadapted and non-neuroadapted virus and partial sequence analysis of the neuroadapted strain," J. Gen. Virol. 77 (Pt 6):1277-85, Society for General Microbiology, London, England.

Secko, 2005, "Immunotherapy for West Nile virus infection," CMAJ 173(6):591.

Seif et al., 1995, "Finer mapping of neutralizing epitope(s) on the C-terminal of Japanese encephalitis virus E protein expressed in recombinant *Escherichia coli* system," Vaccine 13(16):1515-21, Elsevier, Amsterdam, Holland.

Shimoni et al., 2001, "Treatment of West Nile virus encephalitis with intravenous immunoglobulin," Emerg. Infect. Dis. 7(4):759.

Shrestha et al., 2004, "Role of CD8+ T cells in control of West Nile virus infection," J. Virol. 78(15):8312-21, American Society for Microbiology, Washington, DC.

Stanley et al., 1986, "Monoclonal antibody cure and prophylaxis of lethal Sindbis virus encephalitis in mice," J. Virol. 58(1):107-15, American Society for Microbiology, Washington, DC.

Volk et al., 2004, "Solution structure and antibody binding studies of the envelope protein domain III from the New York strain of West Nile virus," J. Biol. Chem. 279(37):38755-61.

Wu et al., 1997, "Japanese encephalitis virus antigenic variants with characteristic differences in neutralization resistance and mouse virulence," Virus Res. 51:173-181.

Yang et al., 2001, "Induction of potent Th1-type immune responses from a novel DNA vaccine for West Nile virus New York isolate (WNV-NY 1999).," J. Infect. Dis. 184(7):809-16, University of Chicago Press, Chicago, IL.

* cited by examiner

A.
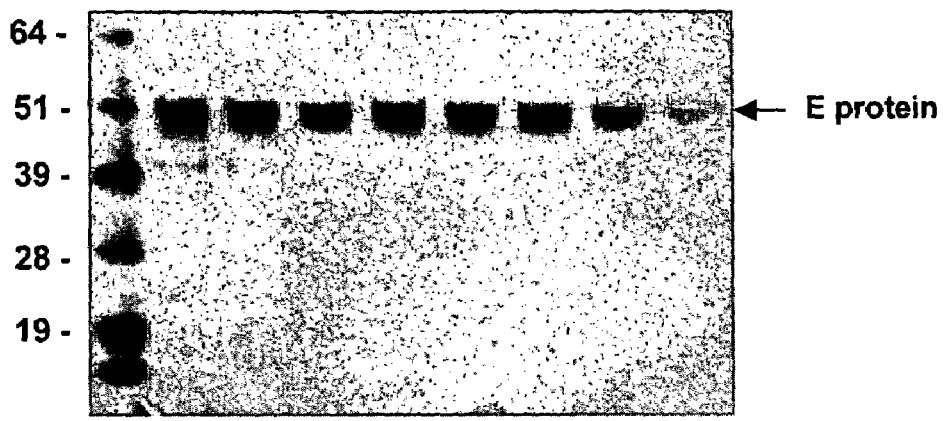
B.
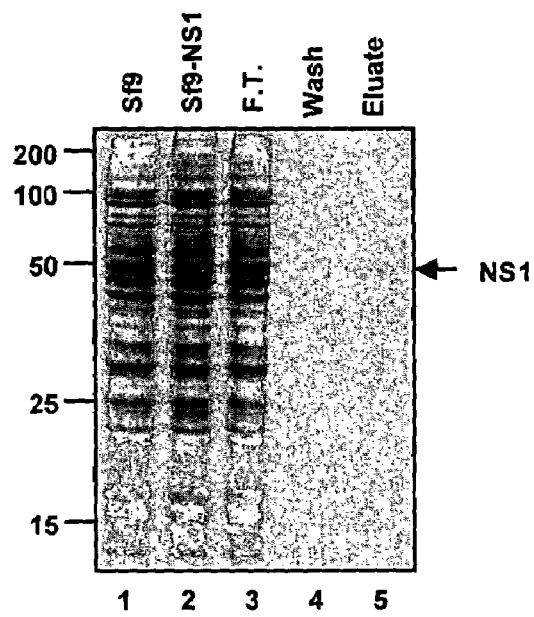
FIG. 1

A.
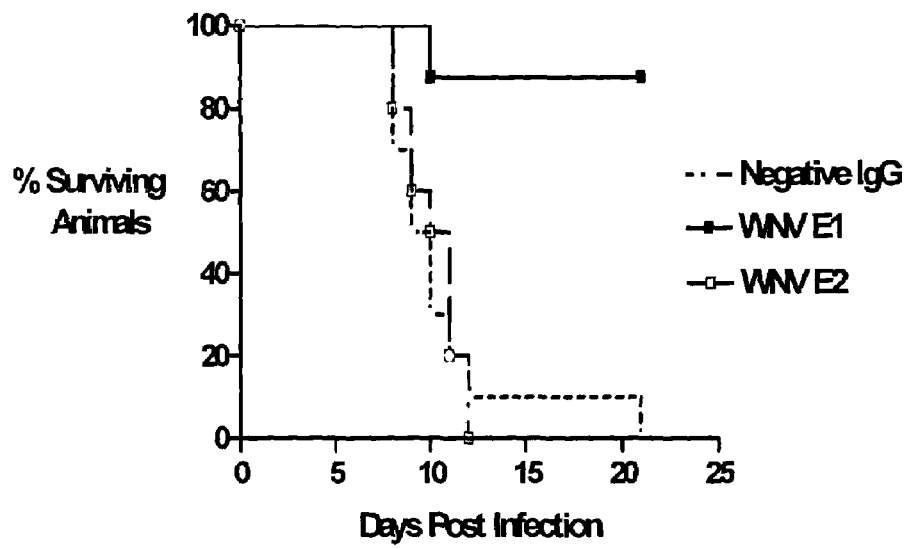
B.
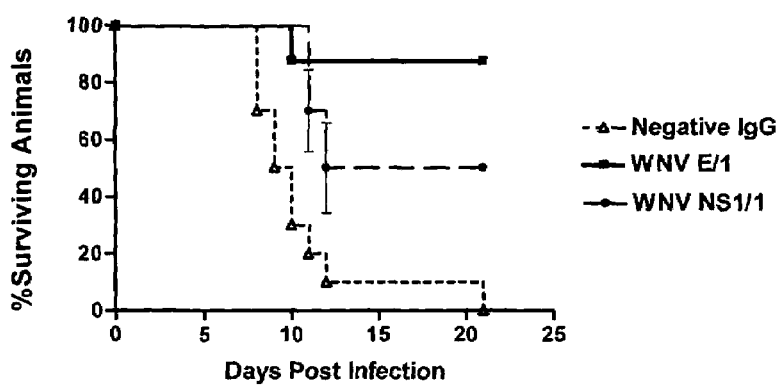
FIG.2

A
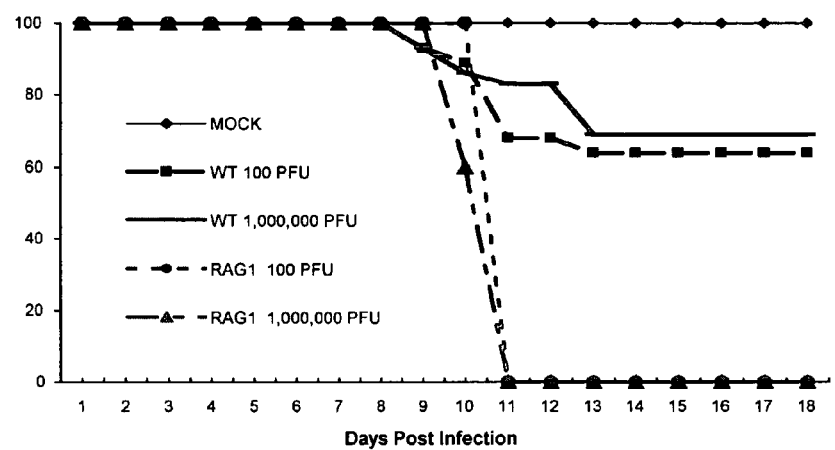
B
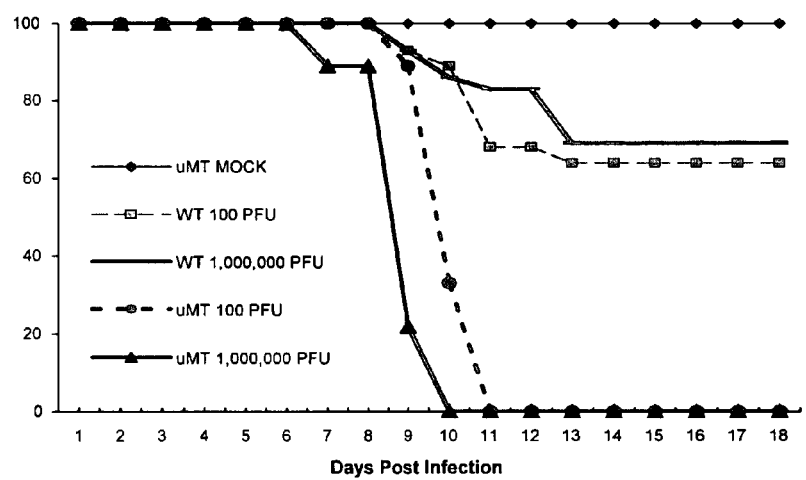
FIG. 5

A
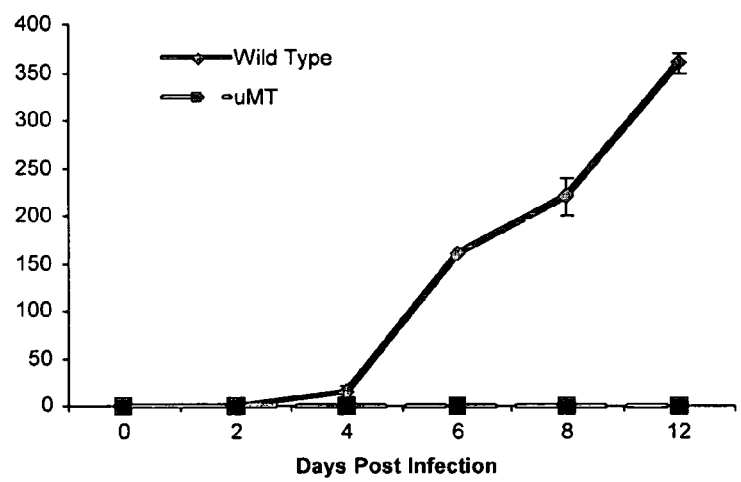
B
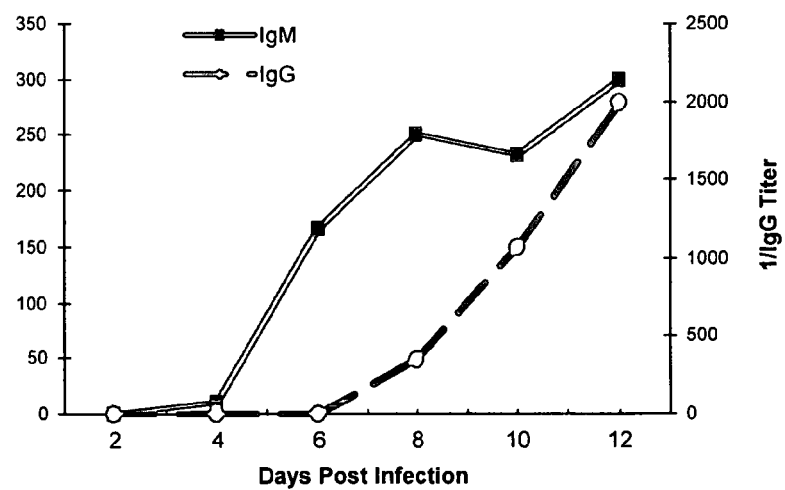
FIG. 7

A
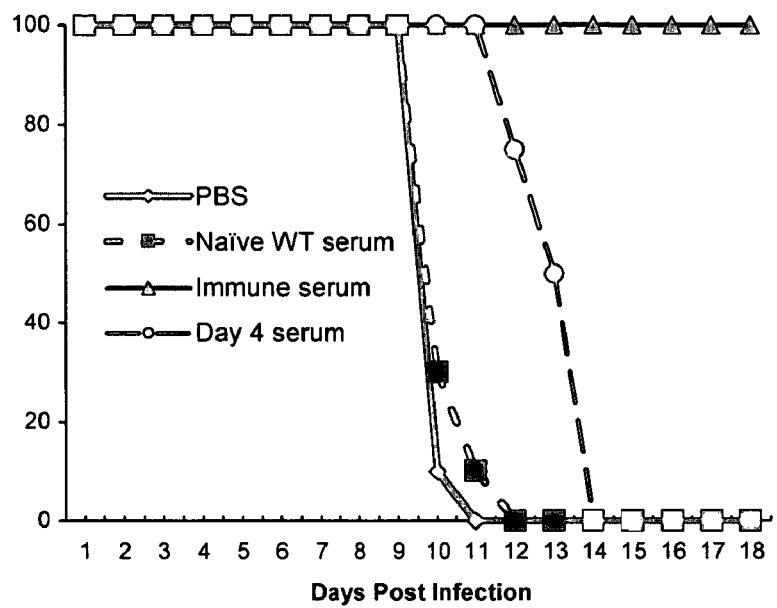
B
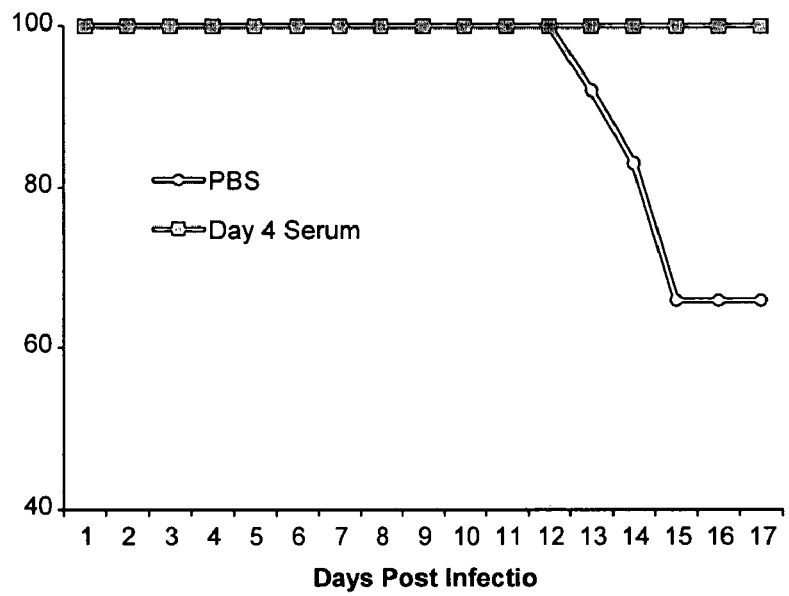
FIG. 8

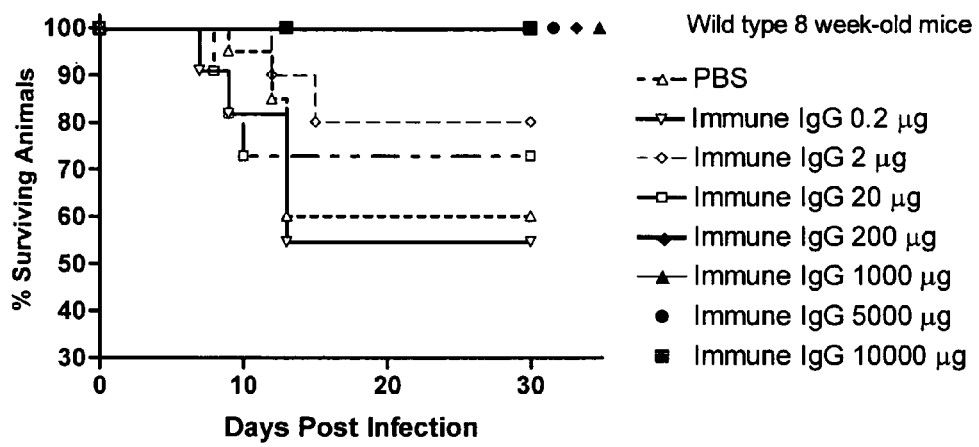
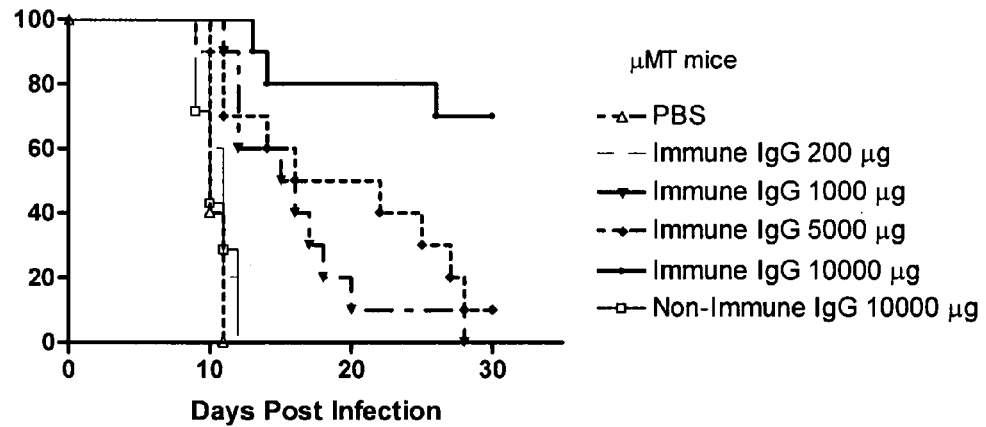
FIG. 9

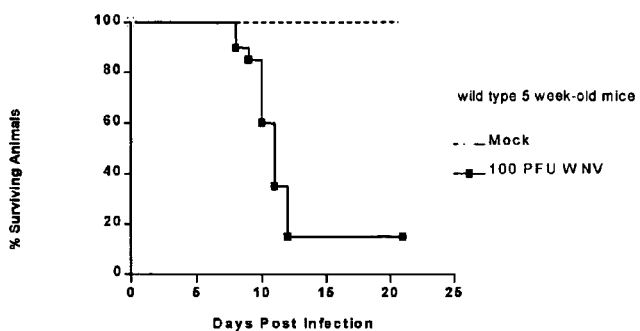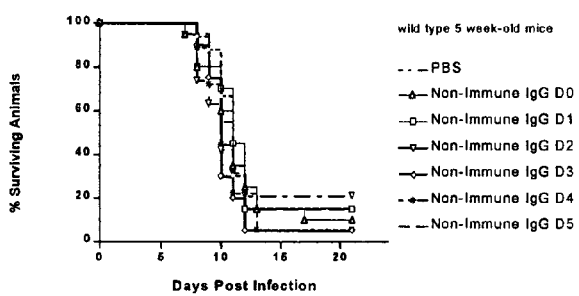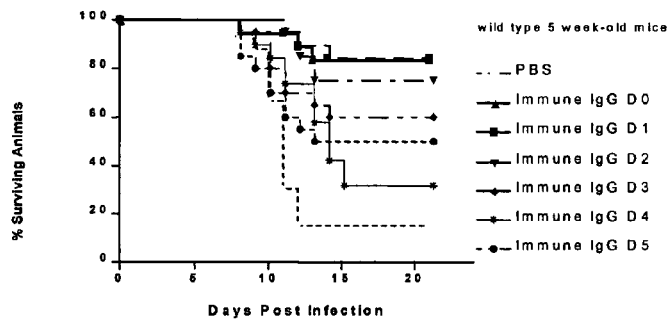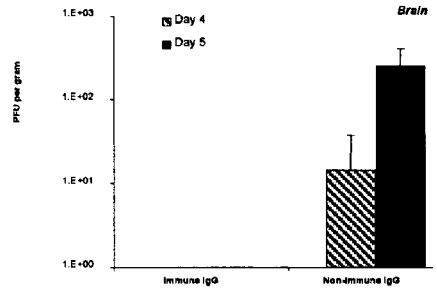
FIG. 11

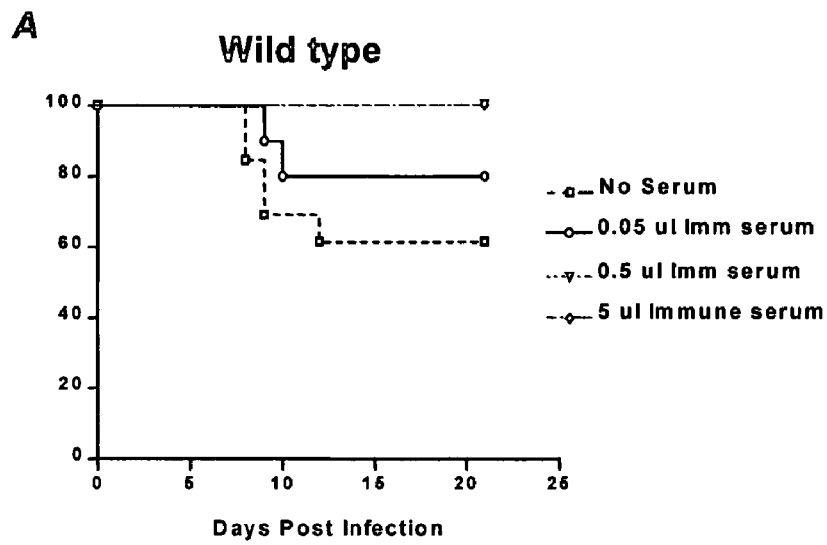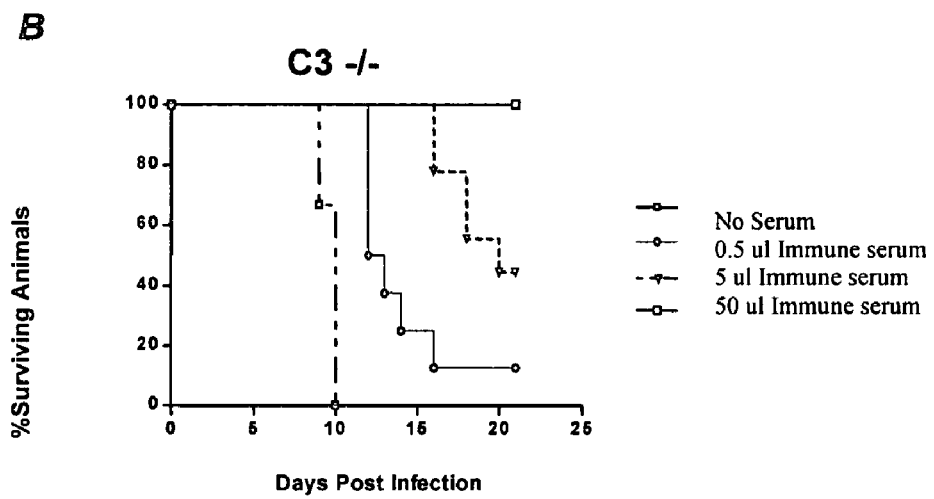
FIG. 12

A
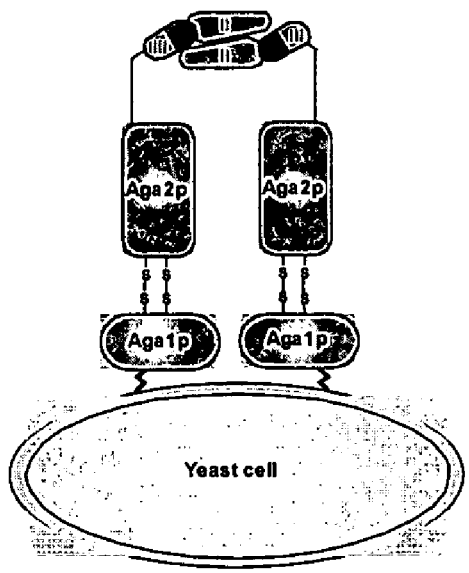
B
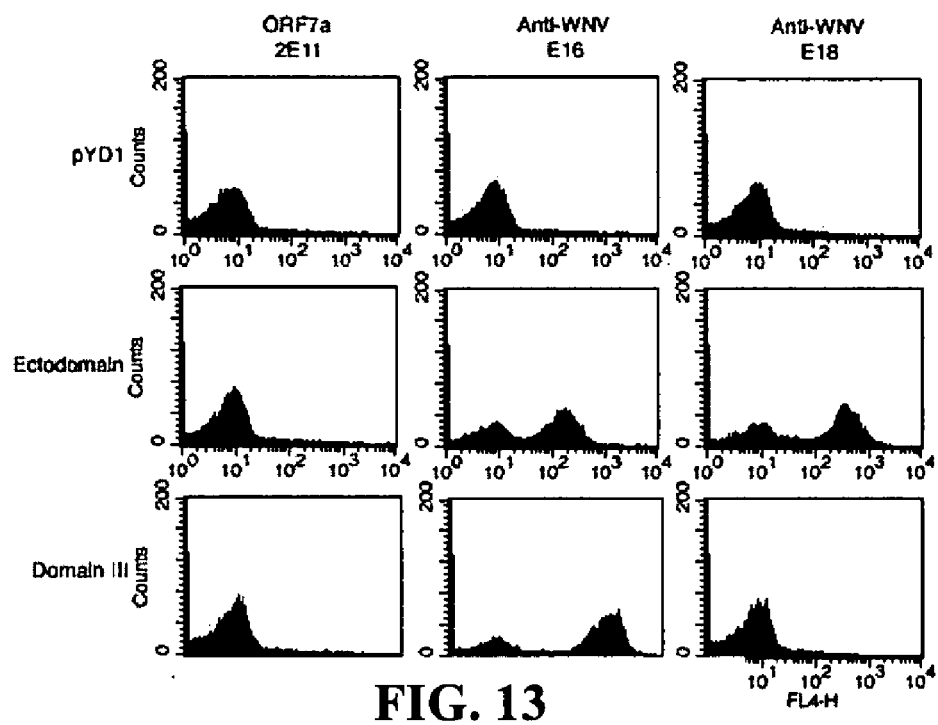
FIG. 13

A

Neutralization of Lineage I WNV

- SARS anti-ORF8
- WNV anti-E7
- WNV anti-E16

B

Neutralization of Lineage II WNV

- Anti-SARS
- Anti-WNV E7
- Anti-WNV E16

FIG. 15

A. Complement-Dependent
Neutralization of WNV

% Plaques Generated vs % Complement

- WNV E1 (IgG2a)
- WNV E8 (IgG1)
- ORF7a (IgG2a)
- No Antibody

B. Complement-Mediated
Cytotoxicity of WNV Infected Cells

% Cell Death (PI Staining) vs % Complement

- Infected anti-WNV E16
- Infected anti-WNV E1
- Infected anti-SARS
- Infected No Ab
- Uninfected anti-WNV E16
- Uninfected anti-WNV E1
- Uninfected anti-SARS
- Uninfected No Ab

FIG. 16

A
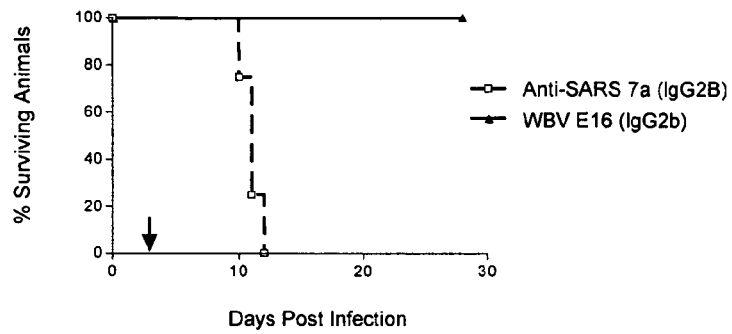
B
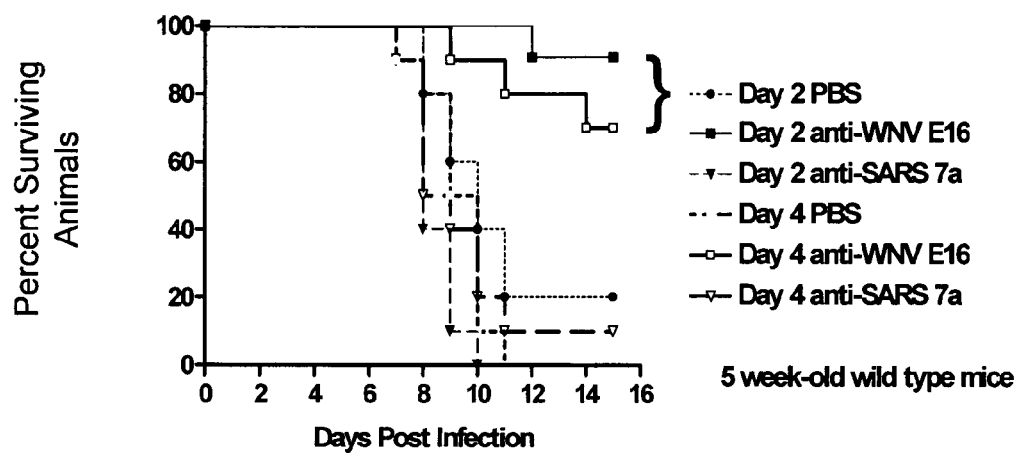
FIG. 17

```
Purify E and NS1 proteins
        │
        ▼
Generate mouse mAbs against
    E and NS1 proteins
        │
        ▼
Test mAbs for inhibitory activity and specificity (in vitro)
        │
        ▼
Test mAbs for in vivo
   inhibitory activity
        │
        ▼
Choice of 6 candidate mAbs ─────────▶ Clone and sequence candidate
                                       mouse mAbs
                                              │
                                              ▼
Re-test chimerized mAbs for binding  ◀──── Chimerization of 6 mAbs
specificity and in vivo inhibitory activity:   With small-scale production
Choice of best 4 mAbs
        │
        ▼
                                      Design of humanized mAbs by CDR
                                      grafting
                                              │
                                              ▼
                                      Generation of stable cell lines that
                                      produce humanized mAbs
Re-test humanized mAbs for binding  ◀────
specificity and in vivo inhibitory activity
```

FIG. 18

ANTIBODIES AGAINST WEST NILE VIRUS AND THERAPEUTIC AND PROPHYLACTIC USES THEREOF

This application claims the benefit of U.S. Provisional Application No. 60/581,819, filed on Jun. 21, 2004, which is incorporated herein by reference in its entirety.

1. FIELD OF INVENTION

The present invention relates to compositions comprising antibodies or fragments thereof that immunospecifically bind to one or more antigens of a flavivirus, particularly of West Nile Virus (WNV), and methods for preventing, treating or ameliorating symptoms associated with a flavivirus, particularly of West Nile Virus (WNV), infection utilizing said compositions. In particular, the present invention relates to methods for preventing, treating or ameliorating symptoms associated with WNV infection, said methods comprising administering to a human subject an effective amount of one or more antibodies or fragments thereof that immunospecifically bind to a WNV antigen. The present invention also relates to detectable or diagnostic compositions comprising antibodies or fragments thereof that immunospecifically bind to a WNV antigen and methods for detecting or diagnosing WNV infection utilizing said compositions.

2. BACKGROUND OF THE INVENTION

WNV cycles between mosquitoes and birds but also infects humans, horses, and other vertebrate species. It is endemic in parts of Africa, Europe, the Middle East, and Asia, and outbreaks throughout the United States during the past four years indicate that it has established its presence in the Western Hemisphere. Humans develop a febrile illness that can progress rapidly to a meningitis or encephalitis syndrome (Hubalek et al., 1999, Emerg Inf Dis 5:643-650), and no specific therapy or vaccine has been approved for use in humans.

Virology. A member of the *Flavivirus* genus of the Flaviviridae family, WNV is a neurotropic enveloped virus with a single-stranded, positive-polarity 11-kilobase RNA genome. It is translated in the cytoplasm as a polyprotein, and cleaved into structural (C, M, and E) and non-structural (NS1, NS2A, NS2B, NS3, NS4A, NS4B, and NS5) proteins by virus- and host-encoded proteases. The structural proteins include a capsid protein (C), a transmembrane protein (M) that regulates fusion of the virus with the host membrane, and an envelope protein (E) that functions in receptor binding, membrane fusion, and viral assembly. The role of nonstructural proteins is not fully delineated but these proteins form the viral protease (NS2B, NS3), NTPase (NS3), RNA helicase (NS3), and RNA-dependent RNA polymerase (NS5) (Chambers et al., 1990, Annu. Rev. Microbiol. 44: 649-88). After the E protein of WNV binds to an uncharacterized cell surface receptor, viral uptake is believed to occur through receptor-mediated endocytosis (Chambers et al., 1990, Annu. Rev. Microbiol. 44: 649-88). In the endosome, an acid-catalyzed conformational change in E (Gollins et al., 1986, J. Gen. Virol. 67:1941-1950; Kimura et al., T., 1986, J Gen Virol 67:2423-33) releases the nucleocapsid into the cytoplasm. At the endoplasmic reticulum (ER) membrane, the structural proteins and NS1 undergo co-translational translocation, glycosylation, and membrane-associated cleavage, while the other nonstructural proteins are translated in the cytoplasm (Falgout et al., 1995, J Virol 69:7232-43; Markoff et al., 1994, Virology 204:526-40). Assembly occurs at the ER, and viral particles are exocytosed.

WNV Immunology. Host factors including immune status influence the expression of WNV disease in humans (Camenga et al., 1974, J Infect Dis 130:634-41). Infants, the elderly, and patients with impaired immune systems are at greatest risk for severe neurological disease (Asnis et al., 2000, Clin Infect Dis 30:413-8; Hubalek et al., 1999, Emerg Inf Dis 5:643-650; Tsai et al., 1998, Lancet 352:767-71. Investigations are beginning to elucidate the molecular basis of WNV infection and the protective immune system response. Maturation of the immune system correlates with resistance to WNV infection (Eldadah et al., 1967, Am J Epidemiol 86:776-90; Eldadah et al., 1967, Am J Epidemiol 86:765-75; Weiner et al., 1970, J Hyg (Lond) 68:435-46. Depletion of macrophages increases the neuro-invasiveness and virulence of an attenuated strain (Ben-Nathan et al., 1996, Arch Virol 141:459-69). Lymphocytes are critical for protection against WNV infection as SCID and RAG1 mice uniformly succumb to infection with WNV (Diamond et al., 2003, J Virol 77:2578-2586; Halevy et al., 1994, Arch Virol 137:355-70. Several studies demonstrate that components of humoral immunity (IgM, IgG, and complement) have essential functions early in the course of infection and prevent dissemination to the central nervous system (CNS) (Diamond et al., 2003, J Virol 77:2578-2586; Diamond et al., 2003, Viral Immunology 16:259-278; Diamond et al., 2003, J Exp Med. 198:1853-62; Engle et al., 2003, J Virol 77:12941-9). The cellular basis of immunity against WNV is beginning to be delineated. Several studies suggest a protective role for cytotoxic and helper T cells. In vitro, T cells kill targets, proliferate, and release inflammatory cytokines after exposure to WNV-infected cells (Douglas et al., 1994, Immunology 82:561-70; Kesson et al., 1987, J Gen Virol 68:2001-6; Kulkarni et al., 1991, Viral Immunol 4:73-82; Liu et al., 1989, J Gen Virol 70:565-73). In vivo, antigen-specific helper and cytotoxic T cell responses are generated in mice after administration of a candidate vaccine strain of WNV (Yang et al., 2001, J Infect Dis 184:809-16). Although the precise contribution of T cell-mediated immunity in vivo to viral clearance and long-term immunity has yet to be established, recent studies demonstrate an essential role for T cells in the control of WNV infection. Mice that lack $CD8^+$ T cells or classical class I MHC molecules show increased mortality and viral loads, and long-term viral persistence in the CNS after WNV infection (Shrestha et al., 2004, J Virol. 78:8312-21), and an absence of γδ T cells results in increased mortality after WNV infection (Wang et al., 2003, J Immunol 171:2524-2531).

Antivirals. At present, treatment for all flavivirus infections, including WNV, is supportive. Ribavirin has been suggested as a candidate agent because it inhibits WNV infection in cells (Jordan et al., 2000, J Infect Dis 182:1214-7); however, its activity was modest at concentrations that are achievable in the CNS (Anderson et al., 2002, Emerg Infect Dis 8:107-8; Jordan et al., 2000, J Infect Dis 182:1214-7). The limited in vivo experience with ribavirin against flaviviruses has not been promising, as it failed to attenuate infection of the closely related Dengue (DEN) virus in mice (Koff et al., 1983, Antimicrob Agents Chemother 24:134-6) and monkeys (Malinoski et al., 1990, Antiviral Res 13:139-49). Based on preliminary cell culture studies (Anderson et al., 2002, Emerg Infect Dis 8:107-8), interferon (IFN) $α_{2b}$ was recently been proposed as a possible therapy for WNV. Although in vivo studies have not been performed with WNV, based on experiments with related flaviviruses, IFNs may inhibit WNV dissemination (Harinasuta et al., 1985, Southeast Asian J Trop Med Public Health 16:332-6). Mice that are deficient in IFN α, β, and γ receptors succumb to DEN (Johnson et al., 1999, J Virol 73:783-6) or Murray Valley encephalitis (Lobigs et al., 2003, J Gen Virol 84:567-72) virus infection and mice deficient in IFN γ produced higher viral loads after yellow fever virus infection (Liu et al., 2001, J Virol 75:2107-18). IFN α was effective as prophylaxis and therapy against Saint Louis encephalitis virus in mice (Brooks et al., 1999, Antiviral Res 41:57-64) although clinical benefit was achieved only when therapy was initiated within 24 hours of infection. Indeed, clinical trials on patients with serologically confirmed Japanese encephalitis virus demonstrated no benefit of IFN therapy (Solomon et al., 2003, Lancet 361:821-6). Thus, the window of opportunity for IFN α therapy against WNV infection may be too narrow to be clinically relevant.

The present invention is aimed at addressing the concerns and shortcomings of currents prophylactic and therapeutic methods against flaviviral, particularly WNV, infections.

All references cited herein are incorporated herein by reference in their entirety and for all purposes to the same extent as if each individual publication or patent or patent application was specifically and individually indicated to be incorporated by reference in its entirety for all purposes.

3. SUMMARY OF THE INVENTION

The present invention is based, in part, on the development of methods for achieving or inducing a prophylactically and/or therapeutically effective response against flaviviral infections, particularly west nile virus (WNV) infections. The invention encompasses methods for achieving or inducing a prophylactically and/or therapeutically effective response against flaviviral infections including but not limited to, Japanese Encephalitis (JE, e.g., JE SA14-14-2), Dengue (DEN, e.g., any of the Dengue serotypes 1-4); Murray Valley encephalitis, St Louis Encephalitis, West Nile, Tick borne encephalitis, Hepatitis C viruses, Kunjin virus, Powassan virus, Kyasanur Forest Disease virus, Yellow Fever Virus and Omsk Hemorrhagic Fever Virus. The methods of the instant invention are more effective prophylactically and therapeutically compared to conventional modes of treatment or prophylaxis of flaviviral infections, particularly WNV infections, including but not limited to, passive administration of immune serum or purified polyclonal antibody, administration of γ-globulin, interferon alpha therapy and intravenous immunoglobulin (IVIG) therapies. The present invention is based, in part, on the discovery by the inventors of monoclonal antibodies that immunospecifically bind distinct functional and structural domains of the structural, e.g., E protein, and non-structural, e.g., NS1 protein proteins of the WNV. The antibodies of the invention are effective in aborting an established infection and thus significantly limit morbidity and mortality of hosts susceptible to WNV infections.

The methods and compositions of the instant invention are particularly effective for prophylaxis against flaviviral infections in a human population which is at an increased risk of flaviviral infections. In specific preferred embodiments, the methods and compositions of the instant invention are particularly useful to a human population which is at an increased risk for of WNV infection including, but not limited to, human infants, elderly, and human patients with impaired immune system.

The present invention provides methods for treating, preventing, or ameliorating a flaviviral infection by administration of one or more antibodies of the invention. Although not intending to be bound by a particular mechanism of action, the optimized monoclonal antibodies of the invention are more effective than current treatments against flaviviral infections such as, for example, treatment using IVIG for WNV infections from donors with high neutralizing titres. Because IVIG is made from human blood plasma, it has an inherent risk of transmitting an infectious agent. Although the source plasma donors are screened and the plasma is solvent/detergent treated to inactivate viruses such as HIV, virus removal and inactivation must be validated to remove a wide variety of agents as a precaution; and the list of agents that can be transmitted by blood grows with every emerging infection. This is especially true for non-enveloped viruses (e.g., parvovirus B19) and prions, which are resistant to most commercial inactivation procedures (see, e.g., Azzi et al., Transfusion Medicine Reviews. 1999. 13:194-204; Blumel et al., Transfusion. 2002. 42:1473-1481). These recent studies confirm that there is never 100% assurance of elimination of infectious agents. Finally, most preparations have excipients such as human albumin, another blood product, and sucrose, which can increase the risk of adverse events. Another limitation of IVIG can be the large volumes needed, especially in patients with cardiac or renal co-morbidities. In using a specific immune globulin from vaccinated donors, while enriched for antibodies to the target agent, most of the preparation contains unrelated antibodies. The present invention cures the deficiency of current IVIG regimens. Antibodies of the instant invention offer an inherently safer and potentially more efficacious alternative to IVIG for the prevention and treatment of flaviviral infections such as those caused by WNV. Additional benefits of the antibodies of the invention include, but are not limited to, their ability to be grown in tissue culture under defined conditions with chemically defined medium without the addition of animal or human-derived proteins; unlike polyclonal serum, they can be selected for desired properties including epitope specificity, affinity and neutralizing capacity, allowing lower doses; and they can be formulated at high concentration to reduce the volume of administration.

The present invention provides isolated antibodies, preferably monoclonal antibodies (including humanized or other engineered versions of antibodies produced by a hybridoma) or fragments thereof that immunospecifically bind to one or more flaviviral antigens, preferably WNV antigens. Preferably, the isolated antibodies of the invention or fragments thereof immunospecifically bind to one or more flaviviral antigens, preferably WNV antigens, regardless of the strain of the virus. In some embodiments, the isolated antibodies of the invention bind with similar affnities and/or avidities to all WNV strains including lineage I and II strains and virulent strains circulating in North America, e.g., New York 1999.

In most preferred embodiments, the present invention provides isolated antibodies, preferably monoclonal antibodies, that immunospecifically bind a structural protein of WNV, e;g., E protein, for prevention and/or treatment of WNV infections in mammals. In a specific embodiment, the isolated antibodies of the invention bind to the ectodomain of WNV E protein, as determined by standard methods known to one skilled in the art and exemplified herein, e.g., ELISA with purified E protein, immunoprecipitation, immunoblotting. In another specific embodiment, the isolated antibodies of the invention bind to domain III of the WNV E protein, comprising amino acids 290 to 415 (see, e.g., Chambers et al., 1990, Annu. Rev. Microbiol. 44: 649-88), as determined by standard methods known to one skilled in the art and exemplified herein, e.g., ELISA, immunoprecipitation, immunoblotting.

The present invention provides methods for treating, preventing, or ameliorating a flaviviral infection by administration of one or more antibodies of the invention. In a specific embodiment, the invention encompasses methods for treating, preventing, or ameliorating a WNV infection comprising administering a first antibody that immunospecifically binds a structural protein of WNV, e.g., E protein, and a second antibody that binds a non-structural protein of WNV, e.g., NS1 protein. Although not intending to be bound by a particular mechanism of action such combination regimens are more effective than single antibody treatment regimens because the RNA-dependent RNA polymerase of WNV has a high error rate and thus a potential to rapidly alter immunodominant residues. In other specific embodiments, the invention encompasses methods for treating, preventing, or ameliorating a WNV infection comprising administering a first antibody that immunospecifically binds an epitope of a structural protein of WNV, e.g., E protein, and a second antibody that binds the same structural protein of WNV but binds at a distinct site.

In other preferred embodiments, the present invention provides isolated monoclonal antibodies that immunospecifically bind a non-structural protein of flaviviral protein particularly WNV, e.g., NS1 protein for prevention and/or treatment of WNV infections in mammals. In some embodiments, the antibodies of the invention bind to one or more epitopes of a structural protein and/or one or more epitopes of a non-structural protein of an WNV. In other embodiments, the present invention also provides antibodies or fragments thereof that differentially or preferentially bind to flaviviral antigens from one strain of the flavivirus versus another strain.

In preferred embodiments, the invention encompasses monoclonal antibodies produced by hybridoma clones E16 C4 E4 ("E16"), E24 D8 C1 ("E24"), and E34 D5 E2 ("E34"), having ATCC Accession Nos. PTA-6050, PTA-6051, and PTA-6052, respectively, variants, or antigen binding fragments thereof, e.g., a humanized or chimerized form, an Fab fragment, etc. In some embodiments, the present invention provides isolated monoclonal antibodies or fragments thereof that immunospecifically bind to one or more WNV antigens, said antibodies or antibody fragments comprising a variable heavy ("VH") chain having an amino acid sequence of any one of the VH domains listed in SEQ ID NOs. 4, 8, and 12. The present invention also provides isolated monoclonal antibodies or fragments thereof that immunospecifically bind to one or more WNV antigens, said antibodies or antibody fragments comprising a VL domain having an amino acid sequence of any one of the VL domains listed in SEQ ID NOs. 2, 6, and 10. The present invention also provides isolated monoclonal antibodies or fragments thereof that immunospecifically bind to one or more WNV antigens, said antibodies or fragments comprising an amino acid sequence of any one of the VH CDRs listed in SEQ ID NOs. 16-17, 20-22, or 26-28, listed in Table 1. The present invention also provides isolated monoclonal antibodies or fragments thereof that immunospecifically bind to one or more WNV antigens, said antibodies or fragments comprising an amino acid sequence of any one of the VL CDRs listed in SEQ ID NOs. 33, 37, or 40-41, listed in Table 1.

TABLE 1

| Segment | Kabat # | E16 | E24 | E34 |
|---|---|---|---|---|
| VH FR1 | 1-30 | QVQLQQSGSELMKPGASV QISCKATGYTFS (SEQ ID NO: 13) | QVQLQQSGPELVKPGALVK ISCKASGHTFT (SEQ ID NO: 14) | QVQLQQSGPELVKPGTLVK ISCKTSGYTFT (SEQ ID NO: 15) |
| CDR H1 | 31-35 | DYWIE (SEQ ID NO: 16) | SYDIN (SEQ ID NO: 17) | SYDIN (SEQ ID NO: 17) |
| FR2 | 36-49 | WVKQRPGHGLEWIG (SEQ ID NO: 18) | WVKQRPGQGLEWIG (SEQ ID NO: 19) | WVKQRPGQGLEWIG (SEQ ID NO: 19) |
| CDR H2 | 50-65 | DILCGTGRTRYNEKL (SEQ ID NO: 20) | WIYPGDGRIKYNEKFKG (SEQ ID NO: 21) | WIFPGDGRIKYNEQIKD (SEQ ID NO: 22) |
| FR3 | 66-94 | KAMATFTADTSSNTAFMQ LSSLTSEDSAVYYCAR (SEQ ID NO: 23) | KAILTADKSSSTAYMQLSS LTSENSAVYFCAR (SEQ ID NO: 24) | KATLTADKSSSTAYMELSS LTSENSAVYFCAR (SEQ ID NO: 25) |
| CDR H3 | 95-102 | SASYGDYADY (SEQ ID NO: 26) | GGSSGTYFDY (SEQ ID NO: 27) | ASYYGSIFDY (SEQ ID NO: 28) |
| FR4 | 103-113 | WGHGTTLTVSS (SEQ ID NO: 29) | WGQGTTLTVSS (SEQ ID NO: 30) | WGQGTTLTVSS (SEQ ID NO: 30) |
| VL FR1 | 1-23 | DIVMTQSHKFMSTSVGDRV SITC (SEQ ID NO: 31) | DIVMTQSHKFMSTSVGDRV SITC (SEQ ID NO: 31) | DIVMTQSHKFMSTSVGDRV NITC (SEQ ID NO: 32) |
| CDR L1 | 24-34 | KASQDVSTAVA (SEQ ID NO: 33) | KASQDVSTAVA (SEQ ID NO: 33) | KASQDVSTAVA (SEQ ID NO: 33) |
| FR2 | 35-49 | WYQQKPGQSPKLLIS (SEQ ID NO: 34) | WYQQKPGQSPKVLIY (SEQ ID NO: 35) | WYQQKPGQSPKLLIY (SEQ ID NO: 36) |
| CDR L2 | 50-56 | WASTRHT (SEQ ID NO: 37) | WASTRHT (SEQ ID NO: 37) | WASTRHT (SEQ ID NO: 37) |
| FR3 | 57-88 | GVPDRFTGSGSGTDYTLTIS SVQAEDLALYYC (SEQ ID NO: 38) | GVPDRFTGSGSGTDYTLTIS SVQAEDLALYYC (SEQ ID NO: 38) | GVPDRFTGSGSGTHYTLTIS SVQAEDLALYYC (SEQ ID NO: 39) |

TABLE 1-continued

| Segment | Kabat # | E16 | E24 | E34 |
|---|---|---|---|---|
| CDRL3 | 89-97 | QQHYTTPLT (SEQ ID NO: 40) | QQHYSNPPT (SEQ ID NO: 40) | QQHYTTPLT (SEQ ID NO: 40) |
| FR4 | 98-107 | FGAGTKLELK (SEQ ID NO: 42) | FGGGTKLEIK (SEQ ID NO: 43) | FGAGTKLELK (SEQ ID NO: 42) |

In most preferred embodiments, the invention encompasses antibodies (e.g., anti-E antibodies) or fragments thereof that have potent neutralizing activity as measured for example using standard methods known in the art and exemplified herein in Example 6.4, e.g., in vitro plaque reduction neutralization titer (PRNT) assay. Although not intending to be bound by a particular mechanims of action the antibodies of the invention may directly neutralize virus, block entry of the virus into the cell, or block fusion and uncoating of the virus inside the cell, thus treating or preventing viral infections. In some embodiments, the invention encompasses antibodies which immunospecifically bind WNV-E protein such that the $PRNT_{50}$ values are at least 1/500, at least 1/750, at least 1/1000, at least 1/1500, at least 1/2000, at least 1/2500, at least 1/3000, at least 1/3500, at least 1/4000, at least 1/4500, at least 1/5000, at least 1/5500, at least 1/6000, at least 1/6500, at least 1/7000, at least 1/7500, at least 1/8000, at least 1/8500, at least 1/9000, at least 1/9500, or at least 1/10,000, preferably at least 1/10,000 at a concentration of 1 mg/mL. The anti-NS1 antibodies of the invention do not have neutralizing activity as determined using the disclosed methods. Although not intending to be bound by a particular mechanism of action the lack of neutralizing activity of the anti-NS1 antibodies of the invention may, in part, be explained by complement lysis of virally infected cells.

In yet other preferred embodiments, antibodies of the invention have enhanced antibody-dependent complement mediated neutralization of WNV infected virions and trigger lysis of WNV-infected cells more effectively, as determined using standard methods known in the art and exemplified herein. Antibodies are added to virus particles in the presence of complement. Subsequently, inhibition of virus activity is determined by plaque reduction assay. For complement-dependent cell lysis, antibodies are added to infected cells in the presence of complement. Subsequently, cell lysis is evaluated by standard methods (e.g., propidium iodide staining and flow cytometry). Although not intending to be bound by a particular mechanism of action, the antibodies of the invention have enhanced clinical efficacy, therapeutically and prophylactically, as they have enhanced effector functions, neutralize virus attachment, trigger complement mediated lysis, promote clearance from the circulatory systems and prevent emergence of viral resistance. The antibodies of the invention preferably have a potent in vivo inhibitory activity, i.e., protect against WNV infection by at least 50%, at least 60%, at least 70%, at least 80%, at least 90%, at least 99%. In vivo inhibitory activity as used herein refers to the activity of the antibodies of the invention to neutralize virus activity, for example, by inhibiting a step in the viral life cycle, e.g., virus attachment. In vivo inhibitory activity may also refer to the ability of the antibody to reduce morbidity and mortality in an animal model of infection.

The present invention provides antibodies or fragments thereof which immunospecifically bind to one or more flaviviral antigens, particularly WNV antigens, and have an apparent dissociation constant of less than 100 ng/mL as determined by a sandwich ELISA. The present invention provides antibodies or fragments thereof which immuospecifically bind to one or more flaviviral antigens, particularly WNV antigens, and have an apparent dissociation constant of about 1-10 nM as measured by surface plasmon resonance (SPR) using a BIAcore sensor. The present invention provides antibodies or fragments thereof which immuospecifically bind to one or more flaviviral antigens, particularly WNV antigens, and have an on rate of about $1 \times 10^4$, about $5 \times 10^4$, about $1 \times 10^5$, about $5 \times 10^5$, about $1 \times 10^6$, or about $5 \times 10^6$ and an off rate of about $1 \times 10^{-3}$, about $5 \times 10^{-4}$, about $1 \times 10^{-4}$, about $5 \times 10^{-5}$, about $1 \times 10^{-5}$, about $5 \times 10^{-6}$, as measured by surface plasmon resonance (SPR) using a BIAcore sensor.

The present invention provides antibodies or fragments thereof which immunospecifically bind to one or more flaviviral antigens, particularly WNV antigens, and have a median effective concentration ($EC_{50}$) of less than 100 ng/mL, in an in vitro microneutralization assay. In particular, the present invention provides compositions for use in the prevention, treatment or amelioration of one or more symptoms associated with a flaviviral infection, said compositions comprising one or more antibodies or fragments thereof which immunospecifically bind to one or more one or more flaviviral antigens, particularly WNV antigens, and have an $EC_{50}$ of less than 0.01 nM, less than 0.025 nM, less than 0.05 nM, less than 0.1 nM, less than 0.25 nM, less than 0.5 nM, less than 0.75 nM, less than 1 nM, less than 1.25 nM, less than 1.5 nM, less than 1.75 nM, or less than 2 nM, in an in vitro microneutralization assay.

The present invention also provides antibodies which immunospecifically bind to one or more flaviviral antigens, particularly WNV antigens, and have increased in vivo half-lives, e.g., by 30 days, relative to known antibodies. In particular, the present invention encompasses antibodies which immunospecifically bind to one or more flaviviral antigens, particularly WNV antigens, and have increased in vivo half-lives relative to known antibodies, said increased half-lives resulting from one or more modifications (e.g., substitutions, deletions, or insertions) in amino acid residues identified to be involved in the interaction of the Fc domain of said antibodies and the FcRn receptor. The present invention also encompasses pegylated antibodies and fragments thereof which immunospecifically bind to one or more flaviviral antigens, particularly WNV antigens, and have increased in vivo half-lives relative to known antibodies. The increased in vivo half-lives of antibodies or fragments thereof which immunospecifically bind to one or more flaviviral antigens, particularly WNV antigens, reduce the dosage and/or frequency of administration of said antibodies or fragments thereof to a subject.

The present invention encompasses the production of novel monoclonal antibodies with specificities for one or more WNV antigens. In particular, the invention provides a method for producing monoclonal antibodies that specifically bind one or more WNV antigens, said method comprising: (a) immunizing one or more BALB/c mice with purified WNV proteins, e.g., NS1, E protein, or an immunogenic fragment thereof using a carbohydrate and lipid based adjuvant; (b) measuring the polyclonal antibody response using a solid phase ELISA based assay; (c) producing hybridoma cells lines from spleen cells of said one or more mice; (d) screening said hybridoma cell lines for one or more hybridoma cell lines that produce antibodies that specifically bind the particular WNV protein; (e) selecting candidate immune mice; (f) priming a single mouse with a high-titer polyclonal (e.g., 1/10,000) response intravenously with purified E or NS1 proteins; (g) harvesting splenocytes and fusing then to the non-secreting P3X63Ag8.6.5.3 myeloma according to standard protocols (Harlow et al., 1988. Antibodies, A laboratory manual. Cold Spring Harbor Laboratory, Cold Spring Harbor). The invention encompasses any antibody produced by said method.

In a preferred embodiment, the invention provides a monoclonal antibody produced by clones E16, E24, or E34, having ATCC Accession Nos. PTA-6050, PTA-6051, and PTA-6052, respectively. In another embodiment, the invention provides an isolated antibody or a fragment thereof that competes for binding with a monoclonal antibody produced by clones E16, E24, or E34. Furthermore, the invention provides hybridoma cell lines E16, E24, or E34, having ATCC Accession Nos. PTA-6050, PTA-6051, and PTA-6052, respectively. In other preferred embodiments, the invention encompasses monoclonal antibodies produced by hybridoma clones E16, E24, or E34, having ATCC Accession Nos. PTA-6050, PTA-6051, and PTA-6052, respectively, variants, or antigen binding fragments thereof, e.g., a humanized or chimerized form, an Fab fragment, etc.

The methods of the invention also encompass polynucleotides that encode the antibodies of the invention. In one embodiment, the invention provides an isolated nucleic acid sequence encoding a heavy chain or a light chain of an antibody or a fragment thereof that specifically binds one or more flaviviral antigens, particularly WNV antigens. The invention also relates to a vector comprising said nucleic acid. In specific embodiments, the invention encompasses any of the nucleotides of SEQ ID Nos. 1, 5, 9, 3, 7, or 11. The invention further provides a vector comprising a first nucleic acid molecule encoding a heavy chain and a second nucleic acid molecule encoding a light chain, said heavy chain and light chain being of an antibody or a fragment thereof that specifically binds one or more flaviviral antigens, particularly WNV antigens. In one specific embodiment, said vector is an expression vector. The invention further provides host cells containing the vectors of or polynucleotides encoding the antibodies of the invention. Preferably, the invention encompasses polynucleotides encoding heavy and light chains of the antibodies produced by the deposited hybridoma clones, having ATCC accession numbers PTA-6050, PTA-6051, and PTA-6052, respectively, or portions thereof, e.g., CDRs, variable domains, etc. and humanized versions thereof.

The invention further provides methods for the production of antibodies of the invention or fragments thereof. The antibodies of the invention or fragments thereof can be produced by any method known in the art for the production of antibodies, in particular, by secretion from cultured hybridoma cells, chemical synthesis or by recombinant expression techniques known in the art. In one specific embodiment, the invention relates to a method for recombinantly producing a flaviviral antigen-specific antibody, said method comprising: (i) culturing under conditions suitable for the expression of said antibody in a medium, a host cell containing a first nucleic acid molecule, operably linked to a heterologous promoter and a second nucleic acid operably linked to the same or a different heterologous promoter, said first nucleic acid and second nucleic acid encoding a heavy chain and a light chain, respectively, of an antibody or a fragment thereof that specifically binds one or more flaviviral antigens; and (ii) recovery of said antibody from said medium.

Preferably, the antibodies of the invention are monoclonal antibodies, and more preferably, humanized or human antibodies. In one specific preferred embodiment, the antibodies of the invention bind to the WNV E protein. In another specific embodiment, the antibodies of the invention specifically or selectively recognize one or more epitopes of WNV E protein. Another embodiment of the invention encompasses the use of phage display technology, DNA shuffling or other methods known in the art to increase the affinity of the antibodies of the invention for WNV E protein. In one specific preferred embodiment, the antibodies of the invention bind to the WNV NS1 protein. In another specific embodiment, the antibodies of the invention specifically or selectively recognize one or more epitopes of WNV NS1 protein. Another embodiment of the invention encompasses the use of phage display technology, DNA shuffling or other methods known in the art to increase the affinity of the antibodies of the invention for WNV NS1 protein. Any screening method known in the art can be used to identify mutant antibodies with increased avidity for WNV E protein (e.g., ELISA). In another specific embodiment, antibodies of the invention are screened using antibody screening assays well known in the art (e.g., BIACORE assays) to identify antibodies with $K_{off}$ rate of about $1\times10^{-3}$, about $5\times10^{-4}$, about $1\times10^{-4}$, about $5\times10^{-5}$, about $1\times10^{-5}$, about $5\times10^{-6}$, about $1\times10^{-6}$, as measured by surface plasmon resonance (SPR) using a BIAcore sensor.

The invention encompasses the use of the antibodies of the invention to detect the presence of one or more flaviviral antigens specifically in a biological sample.

The present invention provides methods of preventing, treating and ameliorating one or more symptoms associated with flaviviral infection, particularly WNV infection, in a subject comprising administering to said subject one or more antibodies or fragments thereof which immunospecifically bind to one or more flaviviral antigens, particularly WNV antigens, with high affinity and/or high avidity. The antibodies of the invention are useful for prevention or treatment of a flaviviral infection for example, in one embodiment, as a single agent therapy. Alternatively, the antibodies of the inventon may be use in a combination therapfor the treatement of prevention of a flaviviral infection with new drugs as they become available.

The invention further provides a pharmaceutical composition comprising (i) a therapeutically or prophylactically effective amount of the antibody or a fragment thereof that specifically binds one or more flaviviral antigens, e.g., WNV antigen; and (ii) a pharmaceutically acceptable carrier.

The present invention encompasses methods of delivering one or more antibodies or fragments thereof which immunospecifically bind to one or more flaviviral antigens, e.g., WNV antigen, directly to the site of flaviviral infection.

The present invention provides antibodies or fragments thereof which immunospecifically bind to one or more flaviviral antigens, particularly WNV antigens, and have an association rate constant or $k_{on}$ rate (antibody (Ab)+antigen (Ag)$^{k_{on}} \rightarrow$Ab-Ag) of at least $1\times10^4$, about $5\times10^4$, about $1\times10^5$, about $5\times10^5$, about $1\times10^6$, or about $5\times10^6$. In particular, the present invention provides compositions for use in the prevention, treatment or amelioration of one or more symptoms associated with a flaviviral infection, said compositions comprising one or more antibodies or fragments thereof which immunospecifically bind to one or more one or more flaviviral antigens, particularly WNV antigens, and have an a $k_{on}$ rate of at least $1\times10^4$, about $5\times10^4$, about $1\times10^5$, about $5\times10^5$, about $1\times10^6$, or about $5\times10^6$.

In another embodiment, the invention provides a method of diagnosis of a flaviviral infection in a subject comprising: (i) contacting a biological sample from said subject with an effective amount of an antibody of the invention; and (ii) detecting binding of said antibody or a fragment thereof, wherein detection of said detectable marker above a background or standard level indicates that said subject has a flaviviral infection.

3.1. DEFINITIONS

As used herein, the term "specifically binds to a flaviviral antigen" and analogous terms refer to antibodies or fragments thereof that specifically bind to a flaviviral antigen or fragment thereof and do not specifically bind to other viral antigens. Examples of flavivrial antigens include, but are not limited to, structural proteins, e.g., C, M, and E, and non-structural proteins, e.g., NS1, NS2A, NS2B, NS3, NS4A, NS4B and NS5. An antibody that specifically binds to a flaviviral antigen or fragment thereof may bind to other peptides or polypeptides with lower affinity as determined by, e.g., immunoassays, BIAcore, or other assays known in the art. Preferably, antibodies or fragments that specifically bind to to a flaviviral antigen or fragment thereof do not cross-react with other antigens. Antibodies or fragments that specifically bind to a flaviviral antigen or fragment thereof can be identified, for example, by immunoassays, BIAcore, or other techniques known to those of skill in the art. An antibody or a fragment thereof binds specifically to a flaviviral antigen or fragment thereof with higher affinity than to any cross-reactive antigen as determined using experimental techniques, such as western blots, radioimmunoassays (RIA) and enzyme-linked immunosorbent assays (ELISAs). See, e.g., Paul, ed., 1989, *Fundamental Immunology Second Edition*, Raven Press, New York at pages 332-336 for a discussion regarding antibody specificity.

As used herein, the terms "antibody" and "antibodies" refer to monoclonal antibodies, multispecific antibodies, human antibodies, humanized antibodies, synthetic antibodies, chimeric antibodies, camelized antibodies, single-chain Fvs (scFv), single chain antibodies, Fab fragments, F(ab') fragments, disulfide-linked Fvs (sdFv), intrabodies, and anti-idiotypic (anti-Id) antibodies (including, e.g., anti-Id and anti-anti-Id antibodies to antibodies of the invention), bispecific, and epitope-binding fragments of any of the above. In particular, antibodies include immunoglobulin molecules and immunologically active fragments of immunoglobulin molecules, i.e., molecules that contain an antigen binding site. Immunoglobulin molecules can be of any type (e.g., IgG, IgE, IgM, IgD, IgA and IgY), class (e.g., $IgG_1$, $IgG_2$, $IgG_3$, $IgG_4$, $IgA_1$ and $IgA_2$) or subclass.

The term "analog" as used herein refers to a polypeptide that possesses a similar or identical function as a flaviviral, including WNV, polypeptide, a fragment of a flaviviral, including WNV polypeptide, an antibody, or antibody fragment but does not necessarily comprise a similar or identical amino acid sequence of a flaviviral, including WNV, polypeptide, a fragment of a flaviviral, including WNV, polypeptide, an antibody, or antibody fragment, or possess a similar or identical structure of a flaviviral, including WNV, polypeptide, a fragment of a flaviviral, including WNV, polypeptide, an antibody, or antibody fragment. A polypeptide that has a similar amino acid sequence refers to a polypeptide that satisfies at least one of the following: (a) a polypeptide having an amino acid sequence that is at least 30%, at least 35%, at least 40%, at least 45%, at least 50%, at least 55%, at least 60%, at least 65%, at least 70%, at least 75%, at least 80%, at least 85%, at least 90%, at least 95% or at least 99% identical to the amino acid sequence of a flaviviral, including WNV, polypeptide, a fragment of a flaviviral, including WNV, polypeptide, an antibody, or antibody fragment described herein; (b) a polypeptide encoded by a nucleotide sequence that hybridizes under stringent conditions to a nucleotide sequence encoding a flaviviral, including WNV, polypeptide, a fragment of a flaviviral, including WNV polypeptide, an antibody, or antibody fragment described herein of at least 5 amino acid residues, at least 10 amino acid residues, at least 15 amino acid residues, at least 20 amino acid residues, at least 25 amino acid residues, at least 30 amino acid residues at least 40 amino acid residues, at least 50 amino acid residues, at least 60 amino acid residues, at least 70 amino acid residues, at least 80 amino acid residues, at least 90 amino acid residues, at least 100 amino acid residues, at least 125 amino acid residues, or at least 150 amino acid residues; and (c) a polypeptide encoded by a nucleotide sequence that is at least 30%, at least 35%, at least 40%, at least 45%, at least 50%, at least 55%, at least 60%, at least 65%, at least 70%, at least 75%, at least 80%, at least 85%, at least 90%, at least 95% or at least 99% identical to the nucleotide sequence encoding a flaviviral, including WNV, polypeptide, a fragment of a flaviviral, including WNv, polypeptide, an antibody, or antibody fragment described herein. A polypeptide with similar structure to a flaviviral, including WNV, polypeptide, a fragment of a flaviviral, including WNV, polypeptide, an antibody, or antibody fragment described herein refers to a polypeptide that has a similar secondary, tertiary or quaternary structure of a WNV polypeptide, a fragment of a flaviviral, including WNV, an antibody, or antibody fragment described herein. The structure of a polypeptide can determined by methods known to those skilled in the art, including but not limited to, X-ray crystallography, nuclear magnetic resonance, and crystallographic electron microscopy.

The term "derivative" as used herein refers to a polypeptide that comprises an amino acid sequence of a flaviviral, including WNV, polypeptide, a fragment of a flaviviral, including WNV, polypeptide, an antibody that immunospecifically binds to a flaviviral, including WNV, polypeptide, or an antibody fragment that immunospecifically binds to a flaviviral, including WNV, polypeptide which has been altered by the introduction of amino acid residue substitutions, deletions or additions. The term "derivative" as used herein also refers to a flaviviral, including WNV, polypeptide, a fragment of a flaviviral, including WNV, polypeptide, an antibody that immunospecifically binds to a flaviviral, including WNV, polypeptide, or an antibody fragment that immunospecifically binds to a flaviviral, including WNV, polypeptide which has been modified, i.e, by the covalent attachment of any type of molecule to the polypeptide. For example, but not by way of limitation, a flaviviral, including WNV, polypeptide, a fragment of a flaviviral, including WNV, polypeptide, an antibody, or antibody fragment may be modified, e.g., by glycosylation, acetylation, pegylation, phosphorylation, amidation, derivatization by known protecting/blocking groups, proteolytic cleavage, linkage to a cellular ligand or other protein, etc. A derivative of a flaviviral, including WNV, polypeptide, a fragment of a flaviviral, including WNV, polypeptide, an antibody, or antibody fragment may be modified by chemical modifications using techniques known to those of skill in the art, including, but not limited to specific chemical cleavage, acetylation, formylation, metabolic synthesis of tunicamycin, etc. Further, a derivative of a flaviviral, including WNV, polypeptide, a fragment of a flaviviral, including WNV, polypeptide, an antibody, or antibody fragment may contain one or more non-classical amino acids. A polypeptide derivative possesses a similar or identical function as a flaviviral, including WNV, polypeptide, a fragment of a flaviviral, including WNV, polypeptide, an antibody, or antibody fragment described herein.

The term "effective neutralizing titer" as used herein refers to the amount of antibody which corresponds to the amount present in the serum of animals that has been shown to be either clinically efficacious (in humans) or to reduce virus by 50%, 80%, 90% or 99% in, for example, mice. The 99% reduction is defined by a specific challenge, e.g., $10^3$ pfu, $10^4$ pfu, $10^5$ pfu, $10^6$ pfu, $10^7$ pfu, $10^8$ pfu, or $10^9$ pfu, of a flavivirus, e.g., a WNV, or by the relative amount of virus present in the blood of an animal before and after therapeutic intervention. The terms "effective neutralizing titer" or "neutralizing titer" also refer to the titer of antibody that results in a given (e.g., 90%) reduction in the number of cells producing infectious virus using the plaque reduction assay, which is an in vitro assay and evaluates the ability of a given concentration of of antibody to inhibit 50 (PRNT50) or 90 (PRNT90) % of infection in BHK21 or Vero cells.

The term "epitopes" as used herein refers to portions of a flavivirus, including WNV, polypeptide having antigenic or immunogenic activity in an animal, preferably a mammal, and most preferably in a human. An epitope having immunogenic activity is a portion of a flavivirus, including WNV, polypeptide that elicits an antibody response in an animal. An eptiope having antigenic activity is a portion of a flaviviral, including WNV, polypeptide to which an antibody immunospecifically binds as determined by any method well known in the art, for example, by the immunoassays described herein. Antigenic epitopes need not necessarily be immunogenic.

The term "fragment" as used herein refers to a peptide or polypeptide comprising an amino acid sequence of at least 5 contiguous amino acid residues, at least 10 contiguous amino acid residues, at least 15 contiguous amino acid residues, at least 20 contiguous amino acid residues, at least 25 contiguous amino acid residues, at least 30 contiguous amino acid residues, at least 35 contiguous amino acid residues, at least 40 contiguous amino acid residues, at least 50 contiguous amino acid residues, at least 60 contiguous amino residues, at least 70 contiguous amino acid residues, at least contiguous 80 amino acid residues, at least contiguous 90 amino acid residues, at least contiguous 100 amino acid residues, at least contiguous 125 amino acid residues, at least 150 contiguous amino acid residues, at least contiguous 175 amino acid residues, at least contiguous 200 amino acid residues, or at least contiguous 250 amino acid residues of the amino acid sequence of a flaviviral, including WNV, polypeptide or an antibody that immunospecifically binds to a flaviviral, including WNV, polypeptide. In certain embodiments, a fragment refers to a peptide or polypeptide comprising an amino acid sequence of at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, or at least 50 contiguous amino acid residues of a WNV structural or non-structural protein. In other embodiments, a fragment refers to a peptide or polypeptide comprising an amino acid of at least 5 contiguous amino acid residues, at least 10 contiguous amino acid residues, at least 15 contiguous amino acid residues, at least 20 contiguous amino acid residues, at least 25 contiguous amino acid residues, at least 30 contiguous amino acid residues, at least 35 contiguous amino acid residues, at least 40 contiguous amino acid residues, or at least 50 contiguous amino acid residues of a VH and/or VL domain of an antibody that immunospecifically binds to a flaviviral, including WNV, polypeptide. Preferably, a fragment of a flaviviral, including WNV, polypeptide or a fragment of an antibody that immunospecifically binds to a flaviviral, including WNV, polypeptide retains at least one function of said flaviviral, including WNV, polypeptide or antibody.

An "isolated" or "purified" antibody or fragment thereof is substantially free of cellular material or other contaminating proteins from the cell or tissue source from which the protein is derived, or substantially free of chemical precursors or other chemicals when chemically synthesized. The language "substantially free of cellular material" includes preparations of an antibody or antibody fragment in which the antibody or antibody fragment is separated from cellular components of the cells from which it is isolated or recombinantly produced. Thus, an antibody or antibody fragment that is substantially free of cellular material includes preparations of antibody or antibody fragment having less than about 30%, 20%, 10%, or 5% (by dry weight) of heterologous protein (also referred to herein as a "contaminating protein"). When the antibody or antibody fragment is recombinantly produced, it is also preferably substantially free of culture medium, i.e., culture medium represents less than about 20%, 10%, or 5% of the volume of the protein preparation. When the antibody or antibody fragment is produced by chemical synthesis, it is preferably substantially free of chemical precursors or other chemicals, i.e., it is separated from chemical precursors or other chemicals which are involved in the synthesis of the protein. Accordingly such preparations of the antibody or antibody fragment have less than about 30%, 20%, 10%, 5% (by dry weight) of chemical precursors or compounds other than the antibody or antibody fragment of interest. In a preferred embodiment, antibodies of the invention or fragments thereof are isolated or purified.

An "isolated" nucleic acid molecule is one which is separated from other nucleic acid molecules which are present in the natural source of the nucleic acid molecule. Moreover, an "isolated" nucleic acid molecule, such as a cDNA molecule, can be substantially free of other cellular material, or culture medium when produced by recombinant techniques, or substantially free of chemical precursors or other chemicals when chemically synthesized. In a preferred embodiment, nucleic acid molecules encoding antibodies of the invention or fragments thereof are isolated or purified.

The term "fusion protein" as used herein refers to a peptide, polypeptide or protein that comprises an amino acid sequence of an antibody or fragment thereof that immunospecifically binds to a flaviviral, including WNV, antigen and an amino acid sequence of a heterologous peptide, polypeptide or protein. In certain embodiments, a fusion protein retains the ability to immunospecifically bind to a flaviviral, including WNV, antigen. In other embodiments, a fusion protein does not retain the ability to immunospecifically bind to a flaviviral, including WNV, antigen.

As used herein, the term "humanized antibody" refers to forms of non-human (e.g., murine) antibodies that are chimeric antibodies which contain minimal sequence derived from non-human immunoglobulin. For the most part, humanized antibodies are human immunoglobulins (recipient antibody) in which hypervariable region residues of the recipient are replaced by hypervariable region residues from a non-human species (donor antibody) such as mouse, rat, rabbit or non-human primate having the desired specificity, affinity, and capacity. In some instances, Framework Region (FR) residues of the human immunoglobulin are replaced by corresponding non-human residues. Furthermore, humanized antibodies may comprise residues which are not found in the recipient antibody or in the donor antibody. These modifications are made to further refine antibody performance. In general, the humanized antibody will comprise substantially all of at least one, and typically two, variable domains, in which all or substantially all of the hypervariable regions correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin that immunospecifically binds to one or more flaviviral antigens, that has been altered by the introduction of amino acid residue substitutions, deletions or additions (i.e., mutations). In some embodiments, a humanized antibody is a derivative. Such a humanized antibody comprises amino acid residue substitutions, deletions or additions in one or more non-human CDRs. The humanized antibody derivative may have substantially the same binding, better binding, or worse binding when compared to a non-derivative humanized antibody. In specific embodiments, one, two, three, four, or five amino acid residues of the CDR have been substituted, deleted or added (i.e., mutated). For further details in humanizing antibodies, see European Patent Nos. EP 239,400, EP 592,106, and EP 519,596; International Publication Nos. WO 91/09967 and WO 93/17105; U.S. Pat. Nos. 5,225,539, 5,530,101, 5,565,332, 5,585,089, 5,766,886, and 6,407,213; and Padlan, 1991, *Molecular Immunology* 28(4/5):489-498; Studnicka et al., 1994, *Protein Engineering* 7(6):805-814; Roguska et al. 1994, *Proc Natl Acad Sci USA* 91:969-973; Tan et al., 2002, *J. Immunol.* 169:1119-25; Caldas et al., 2000, *Protein Eng.* 13:353-60; Morea et al., 2000, *Methods* 20:267-79; Baca et al., 1997, *J. Biol. Chem.* 272:10678-84; Roguska et al., 1996, *Protein Eng.* 9:895-904; Couto et al., 1995, *Cancer Res.* 55 (23 Supp):5973s-5977s; Couto et al., 1995, *Cancer Res.* 55:1717-22; Sandhu, 1994, *Gene* 150:409-10; Pedersen et al., 1994, *J. Mol. Biol.* 235:959-73; Jones et al., 1986, *Nature* 321:522-525; Reichmann et al., 1988, *Nature* 332:323-329; and Presta, 1992, *Curr. Op. Struct. Biol.* 2:593-596.

As used herein, the term "hypervariable region" refers to the amino acid residues of an antibody which are responsible for antigen binding. The hypervariable region comprises amino acid residues from a "Complementarity Determining Region" or "CDR" (i.e., residues 24-34 (L1), 50-56 (L2) and 89-97 (L3) in the light chain variable domain and 31-35 (H1), 50-65 (H2) and 95-102 (H3) in the heavy chain variable domain; Kabat et al., *Sequences of Proteins of Immunological Interest,* 5th Ed. Public Health Service, National Institutes of Health, Bethesda, Md. (1991)) and/or those residues from a "hypervariable loop" (i.e., residues 26-32 (L1), 50-52 (L2) and 91-96 (L3) in the light chain variable domain and 26-32 (H1), 53-55 (H2) and 96-101 (H3) in the heavy chain variable domain; Chothia and Lesk, 1987, *J. Mol. Biol.* 196:901-917). "Framework Region" or "FR" residues are those variable domain residues other than the hypervariable region residues as herein defined.

As used herein, the terms "single-chain Fv" or "scFv" refer to antibody fragments comprise the VH and VL domains of antibody, wherein these domains are present in a single polypeptide chain. Generally, the Fv polypeptide further comprises a polypeptide linker between the VH and VL domains which enables the scFv to form the desired structure for antigen binding. For a review of scFv, see Pluckthun in *The Pharmacology of Monoclonal Antibodies,* vol. 113, Rosenburg and Moore eds. Springer-Verlag, New York, pp. 269-315 (1994). In specific embodiments, scFvs include bi-specific scFvs and humanized scFvs.

As used herein, the terms "nucleic acids" and "nucleotide sequences" include DNA molecules (e.g., cDNA or genomic DNA), RNA molecules (e.g., mRNA), combinations of DNA and RNA molecules or hybrid DNA/RNA molecules, and analogs of DNA or RNA molecules. Such analogs can be generated using, for example, nucleotide analogs, which include, but are not limited to, inosine or tritylated bases. Such analogs can also comprise DNA or RNA molecules comprising modified backbones that lend beneficial attributes to the molecules such as, for example, nuclease resistance or an increased ability to cross cellular membranes. The nucleic acids or nucleotide sequences can be single-stranded, double-stranded, may contain both single-stranded and double-stranded portions, and may contain triple-stranded portions, but preferably is double-stranded DNA.

The term "host" as used herein refers to a mammal, preferably a human.

The term "host cell" as used herein refers to the particular subject cell transfected with a nucleic acid molecule and the progeny or potential progeny of such a cell. Progeny of such a cell may not be identical to the parent cell transfected with the nucleic acid molecule due to mutations or environmental influences that may occur in succeeding generations or integration of the nucleic acid molecule into the host cell genome.

The term "patient" as used herein refers to a mammal (e.g., a horse, cow, pig, dog or cat), preferably a primate, and most preferably a human.

The phrases "a peptide, polypeptide or protein comprising a variable or hypervariable region of an antibody of the invention", "a peptide, polypeptide or protein comprising a VH or VL domain of an antibody of the invention", "a peptide, polypeptide or protein comprising one or more CDRs having an amino acid sequence of one or more of the CDRs listed in Table 1", and analogous phrases as used herein refer to fusion proteins.

In certain embodiments of the invention, a "prophylactically effective serum titer" is the serum titer in a mammal, preferably a human, that reduces the incidence of a flaviviral infection in said mammal. Preferably, the prophylactically effective serum titer reduces the incidence of flaviviral infections in humans with the greatest probability of complications resulting from flaviviral infection (e.g., an immunocompromised, a human infant, or an elderly human). In certain other embodiments of the invention, a "prophylactically effective serum titer" is the serum titer in a mouse model that results in a flaviviral titer 3 days after challenge with $10^3$ pfu that is 99% lower than the flaviviral titer 3 days after challenge with $10^3$ pfu of flaviviral in the same strain of mouse not administered an antibody or antibody fragment that immunospecifically binds to a flaviviral antigen.

In certain embodiments of the invention, a "therapeutically effective serum titer" is the serum titer in a mammal, preferably a human, that reduces the severity, the duration and/or the symptoms associated with a flaviviral infection in said mammal. Preferably, the therapeutically effective serum titer reduces the severity, the duration and/or the number symptoms associated with flaviviral infections in humans with the greatest probability of complications resulting from a flaviviral infection (e.g., a human infant, or an elderly human). In certain other embodiments of the invention, a "therapeutically effective serum titer" is the serum titer in a mouse model that results in a flaviviral titer 3 days after challenge with $10^2$, $10^3$ or $10^4$, pfu that is 99% lower than the flaviviral titer 3 days after challenge with $10^2$, $10^3$ or $10^4$ pfu of flaviviral in the same strain of mouse not administered an antibody or antibody fragment that immunospecifically binds to a flaviviral antigen.

The term "flaviviral antigen" refers to a flaviviral polypeptide or fragment thereof to which an antibody or antibody fragment immunospecifically binds. A flaviviral antigen also refers to an analog or derivative of a flaviviral polypeptide or fragment thereof to which an antibody or antibody fragment immunospecifically binds. In a preferred embodiment, a flaviviral antigen is a WNV E or NS1 protein, a fragment, an analog or a derivative thereof to which an antibody or antibody fragment immunospecifically binds.

The term "antibodies or fragments that immunospecifically bind to a flaviviral antigen" as used herein refers to antibodies or fragments thereof that specifically bind to a flaviviral polypeptide or a fragment of a flaviviral polypeptide and do not non-specifically bind to other polypeptides. Antibodies or fragments that immunospecifically bind to a flaviviral polypeptide or fragment thereof may have cross-reactivity with other antigens. Preferably, antibodies or fragments that immunospecifically bind to a flaviviral polypeptide or fragment thereof do not cross-react with other antigens. Antibodies or fragments that immunospecifically bind to a flaviviral polypeptide can be identified, for example, by immunoassays or other techniques known to those of skill in the art.

To determine the percent identity of two amino acid sequences or of two nucleic acid sequences, the sequences are first aligned for optimal comparison purposes (e.g., gaps can be introduced in the sequence of a first amino acid or nucleic acid sequence for optimal alignment with a second amino acid or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=number of identical overlapping positions/total number of positions×100%). In one embodiment, the two sequences are the same length. The determination of percent identity between two sequences can also be accomplished using a mathematical algorithm. A preferred, non-limiting example of a mathematical algorithm utilized for the comparison of two sequences is the algorithm of Karlin and Altschul, 1990, Proc. Natl. Acad. Sci. U.S.A. 87:2264-2268, modified as in Karlin and Altschul, 1993, Proc. Natl. Acad. Sci. U.S.A. 90:5873-5877. Such an algorithm is incorporated into the NBLAST and XBLAST programs of Altschul et al., 1990, J. Mol. Biol. 215:403. BLAST nucleotide searches can be performed with the NBLAST nucleotide program parameters set, e.g., for score=100, wordlength=12 to obtain nucleotide sequences homologous to a nucleic acid molecule of the present invention. BLAST protein searches can be performed with the XBLAST program parameters set, e.g., to score=50, wordlength=3 to obtain amino acid sequences homologous to a protein molecule of the present invention. To obtain gapped alignments for comparison purposes, Gapped BLAST can be utilized as described in Altschul et al., 1997, Nucleic Acids Res. 25:3389-3402. Alternatively, PSI-BLAST can be used to perform an iterated search which detects distant relationships between molecules (Id.). When utilizing BLAST, Gapped BLAST, and PSI-Blast programs, the default parameters of the respective programs (e.g., of XBLAST and NBLAST) can be used. Another preferred, non-limiting example of a mathematical algorithm utilized for the comparison of sequences is the algorithm of Myers and Miller, 1988, CABIOS 4:11-17. Such an algorithm is incorporated in the ALIGN program (version 2.0) which is part of the GCG sequence alignment software package. When utilizing the ALIGN program for comparing amino acid sequences, a PAM 120 weight residue table, a gap length penalty of 12, and a gap penalty of 4 can be used. The percent identity between two sequences can be determined using techniques similar to those described above, with or without allowing gaps. In calculating percent identity, typically only exact matches are counted.

As used herein, a "therapeutically effective amount" refers to that amount of the therapeutic agent sufficient to treat or manage flaviviral infection or to enhance the therapeutic efficacy of another therapy, e.g., therapeutic antibody, vaccine therapy, etc. A therapeutically effective amount may refer to the amount of therapeutic agent sufficient to delay or minimize the onset of disease. A therapeutically effective amount may also refer to the amount of the therapeutic agent that provides a therapeutic benefit in the treatment or management of a disease. Further, a therapeutically effective amount with respect to a therapeutic agent of the invention means that amount of therapeutic agent alone, or in combination with other therapies, that provides a therapeutic benefit in the treatment or management of a disease, e.g., sufficient to enhance the therapeutic efficacy of a therapeutic antibody sufficient to treat or manage a disease. Used in connection with an amount of an antibody of the invention, the term can encompass an amount that improves overall therapy, reduces or avoids unwanted effects, or enhances the therapeutic efficacy of or synergies with another therapeutic agent.

As used herein, the terms "prophylactic agent" and "prophylactic agents" refer to any agent(s) which can be used in the prevention of a disorder, or prevention of recurrence or spread of a disorder. A prophylactically effective amount may also refer to the amount of the prophylactic agent that provides a prophylactic benefit in the prevention of disease. Further, a prophylactically effective amount with respect to a prophylactic agent of the invention means that amount of prophylactic agent alone, or in combination with other agents, that provides a prophylactic benefit in the prevention of disease. Used in connection with an amount of an antibody of the invention, the term can encompass an amount that improves overall prophylaxis or enhances the prophylactic efficacy of or synergies with another prophylactic agent, such as but not limited to a therapeutic antibody.

As used herein, the terms "manage," "managing" and "management" refer to the beneficial effects that a subject derives from administration of a prophylactic or therapeutic agent, which does not result in a cure of the disease. In certain embodiments, a subject is administered one or more prophylactic or therapeutic agents to "manage" a disease so as to prevent the progression or worsening of the disease.

As used herein, the terms "prevent", "preventing" and "prevention" refer to the prevention of the recurrence or onset of one or more symptoms of a disorder in a subject resulting from the administration of a prophylactic or therapeutic agent.

As used herein, the term "in combination" refers to the use of more than one prophylactic and/or therapeutic agents. The use of the term "in combination" does not restrict the order in which prophylactic and/or therapeutic agents are administered to a subject with a disorder, e.g., hyperproliferative cell disorder, especially cancer. A first prophylactic or therapeutic agent can be administered prior to (e.g., 1 minute, 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 1 minute, 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second prophylactic or therapeutic agent to a subject which had, has, or is susceptible to a disorder. The prophylactic or therapeutic agents are administered to a subject in a sequence and within a time interval such that the agent of the invention can act together with the other agent to provide an increased benefit than if they were administered otherwise. Any additional prophylactic or therapeutic agent can be administered in any order with the other additional prophylactic or therapeutic agents.

4. DESCRIPTION OF THE FIGURES

FIGS. 1A AND B. EXPRESSION OF SOLUBLE WNV E AND NS1 PROTEINS.

A. E PROTEIN. The first 430 amino acids of WNV E gene (New York 1999 strain) was cloned by PCR into pFastBac-His, a modified baculovirus shuttle vector that contains an N-terminal polyhedrin promoter and C-terminal histidine repeat. Expression of histidine-tagged soluble WNV virus E protein from recombinant baculovirus in SF9 or Hi-5 cells. Protein was purified by Ni-affinity chromatography after elution with increasing concentrations of imidazole and subjected to SDS-PAGE and silver staining. Molecular weight markers are indicated on the left.

B. NS1 PROTEIN. The full length WNV NS1 gene was cloned into pFastBac upstream of a histidine repeat. NS1 was obtained from SF9 cell supernatants, purified by Ni-affinity chromatography, size exclusion, and Mono Q ionexchange and subjected to SDS-PAGE and Coomassie staining.

FIGS. 2A and B. PROPHYLAXIS STUDIES WITH MABS AGAINST E AND NS1.

A. One mg of purified irrelevant IgG (Anti-DEN type 3, negative IgG), WNV E1 or WNV E2 was administered as a single dose via i.p. route immediately prior to administration of $10^2$ PFU of WNV via footpad inoculation. Data reflects at least 10 mice per condition.

B. One mg of purified negative IgG (anti-DV3), WNV E/1 or WNV NS1/1 was administered as a single dose via an intraperitoneal route immediately prior to administration of $10^2$ PFU of WNV via footpad inoculation. Data reflects at least 10 mice per condition.

FIG. 3. PROPHYLAXIS STUDIES WITH WNV E16, WNV 4-NS1, WNV8-NS1, WNV 10-NS1 or WNV 17-NS1. C57BL/6 mice were administered $10^2$ PFU of virus at day 0. Two days later, infected mice were administered PBS, or 0.5 mg of WNV E16, WNV 4-NS1, WNV8-NS1, WNV 10-NS1 or WNV 17-NS1 antibodies via an intraperitoneal route (arrow) and followed for survival. Data reflects at least 10 mice per condition.

FIG. 4. WNV BURDEN IN PERIPHERAL AND CNS TISSUES IN 8-10 WEEK-OLD ADULT WILD TYPE. Virus levels were measured from serum, kidney, spleen, liver, brain, and spinal cord of wild type mice using a viral plaque assay after tissues were harvested at the indicated days after inoculation. Data is shown as the average PFU per gram of tissue or ml of serum and reflects five to ten mice per time point.

FIGS. 5A AND B. WNV INFECTION IN RAG1 AND μMT IMMUNODEFICIENT MICE.

A. Survival curve: RAG1. T and B cell-deficient or wild type C57BL/6 mice were inoculated via the footpad with $10^2$ or $10^6$ PFU of WNV. The survival curves were constructed from at least three independent experiments.

B. Survival curve: μMT. B cell-deficient or wild type C57BL/6 mice were inoculated via the footpad with $10^2$ or $10^6$ PFU of WNV. The survival curves were constructed from at least three independent experiments.

FIGS. 6A-I. WNV ANTIGEN EXPRESSION IN THE BRAIN OF WILD TYPE AND μMT MICE. The brains of wild type (2 left panels) and μMT (right panel) mice were harvested 8 days after infection with WNV, sectioned, and stained with rat anti-WNV polyclonal serum or a control negative polyclonal rat serum. Typical sections are shown from the cerebellum, brain stem, and cerebral cortex.

FIGS. 7A AND B. KINETICS OF WNV ANTIBODY PRODUCTION IN C57BL/6 MICE.

A. Development of neutralizing antibodies against WNV. Serum was collected from wild type or μMT mice at the indicated days after infection. Neutralizing antibody titers were determined by a plaque reduction neutralization assay. Data is expressed as the reciprocal $PRNT_{50}$, the antibody titer that reduces the number of plaques by 50%.

B. Isotype-specific ELISA. The development of isotype (IgM or IgG) specific antibodies was determined after incubating serum with adsorbed control or viral antigen.

FIGS. 8A AND B. PASSIVE ADMINISTRATION OF SERUM TO 8 WEEK-OLD μMT AND WILD TYPE MICE. Serum was collected from naïve, immune, or mice that were infected with WNV for 4 days. After heat-inactivation, 0.5 ml of serum was administered to μMT (panel A) or wild type mice (panel B) 1 day prior and after infection with $10^2$ PFU of WNV.

FIGS. 9A AND B. PROPHYLAXIS STUDIES WITH HUMAN γ-GLOBULIN

A. Passive administration of human immune γ-globulin to 8 week-old wild type mice. The indicated amounts of purified immune γ-globulin (Lot G12101) (Omrix™) were administered as a single dose via an intraperitoneal route immediately prior to administration of $10^2$ PFU of WNV via footpad inoculation. Data reflects at least 20 mice per condition. Statistical differences compared to the PBS control were as follows. 0.2 μg, 2 μg, and 20 μg: P>0.3; 200 μg, 1000 μg, 5000 μg, and 10,000 μg: P≦0.0002.

B. Passive administration of human immune γ-globulin to 8 week-old μMT mice. The indicated amounts of purified immune γ-globulin (Lot G12101) were administered as a single dose via an intraperitoneal route immediately prior to administration of $10^2$ PFU of WNV via footpad inoculation. Statistical differences compared to the PBS control were as follows. Immune IgG: 200 μg, P>0.3; 1000 μg, P=0.0002; 5000 μg, P=0.009; 10,000 μg, P<0.0001. Non-Immune IgG: 10,000 μg, P>0.7

FIGS. 10A AND B. THERAPEUTIC STUDIES WITH HUMAN γ-GLOBULIN IN 8 WEEK-OLD μMT MICE. A single 15 mg dose of purified non-immune (Panel A, Lot # F43312) or immune (Panel B, Lot # G24191) γ-globulin was administered via an intraperitoneal route immediately prior to (day 0) or at the indicated days after (day 1, 2, or 3) administration of $10^2$ PFU of WNV via footpad inoculation. Data reflects between five and ten mice per condition. Statistical differences compared to the PBS control were as follows. Immune IgG: day 0, P<0.005; day 1, P<0.005; day 2, P=0.06, day 3, P=0.12. Non-immune IgG: day 0, 1, 2, and 3: P>0.4.

FIGS. 11A-D. THERAPEUTIC STUDIES WITH HUMAN γ-GLOBULIN IN 5 WEEK-OLD WILD TYPE MICE.

A. Survival curve of 5 week-old wild type mice after inoculation with $10^2$ PFU of WNV.

B. A single 15 mg dose of purified non-immune γ-globulin was administered via an intraperitoneal route to 5 week-old wild type mice immediately prior to (day 0) or at the indicated days after (day 1, 2, 3, 4 or 5) administration of $10^2$ PFU of WNV via footpad inoculation. Data reflects approximately 20 mice per condition.

C. A single dose of 15 mg of purified immune γ-globulin was administered to 5 week-old wild type mice via an intraperitoneal route immediately prior to (day 0) or at the indicated days after (day 1, 2, 3, 4 or 5) administration of $10^2$ PFU of WNV via footpad inoculation. Data reflects approximately 20 mice per condition.

D. WNV burden in the brain of 5 week-old wild type mice. 5 week-old mice were treated with a single 15 mg dose of immune or non-immune human γ-globulin immediately prior to infection with $10^2$ PFU of WNV. At days 4 and 5 after infection, brains were harvested and viral burdens were determined by plaque assay after tissue homogenization. The data is expressed as PFU per gram.

FIGS. 12A AND B. PASSIVE TRANSFER OF IMMUNE SERUM TO WILD TYPE AND C3 -/- MICE. Eight week-old Wild type (A) or C3 -/- (B) congenic mice were administered the indicated dose of immune serum that had undergone 4 cycles of freeze-thawing to inactivate C3. One day later mice were inoculated with $10^2$ PFU of WNV and evaluated for survival. The data reflects between 10 to 15 mice per arm of each experimental group.

FIGS. 13A AND B. USE OF YEAST DISPLAY TO LOCALIZE MAB BINDING TO E PROTEIN BINDING.

A. To map the region to which anti-WNV E mAbs bound, either the full-length extracellular portion of the E protein or domain III alone were expressed on the surface of yeast cells as an Aga2 fusion protein.

B. Binding of the mAbs to the yeast cells expressing these proteins was measured by FACS analysis. MAb WNV E16 binds to both the entire ectodomain displaying and domain III displaying yeast cells.

FIGS. 14A AND B. YEAST MAPPING OF E16 CONTACT RESIDUES

A. Serial flow cytometric sorts were performed with a mutagenized cDNA library of domain III. Prior to the first sort <1% of the domain III-positive yeast were WNV E16 negative. After the second sort, >85% of the domain III positive yeast were recognized by a polyclonal antibody but not by WNV E16.

B. Yeast Mapping of E16 contact residues with clone 17. A single domain III expressing yeast clone was isolated that lacked binding to WNV E16 but retained binding to 14 other domain III antibodies. Binding profiles to WNV E16 and 4 other example antibodies are shown. This clone has a T332M mutation; thus, one of the contact residues for WNVE16 is at amino acid T332.

FIG. 15. NEUTRALIZATION OF WNV WITH MABS. 100 PFU of WNV was mixed with varying concentrations of two mAbs against WNV (WNV anti-E16 or WNV anti-E7) or a mAb against the ORF7a protein of the SARS coronavirus, and added to monolayers of BHK cells. After addition of an agarose overlay, plates were incubated for 72 h and plaques were scored visually. For both anti-WNV mAbs, ~1/10,000 dilution of a 1 mg stock inhibited infection by approximately 50%.

FIGS. 16A AND B. ANTIBODY-DEPENDENT COMPLEMENT-MEDIATED NEUTRALIZATION AND LYSIS OF WNV

A. Antibody-dependent complement-mediated neutralization of WNV. 100 PFU of WNV was mixed with 25 µg of poorly neutralizing mAbs against WNV E (WNV E1, IgG2a; WNV E8, IgG1) or control protein (SARS-CoV ORF7a 2E11, IgG2b) in the presence of varying concentrations of rabbit complement for 1 h at 37° C. Subsequently, the virus-antibody-complement was added to monolayers of BHK cells. After addition of an agarose overlay, plates were incubated for an additional 72 h and plaques were scored visually.

B. Antibody-dependent complement-mediated lysis of WNV-infected cells. MC57GL cells that were uninfected or infected with WNV (MOI of 5, 24 hours post infection) were incubated with increasing concentrations of baby rabbit complement in the presence or absence of mAbs to WNV E protein (WNV E1, IgG2a; WNV E16, IgG2b) or SARS-Coronavirus (CoV) ORF7a (2E11, IgG2b). After two hours, cells were incubated with propidium iodide and the percentage of dead cells was determined by flow cytometry.

FIGS. 17A AND B. THERAPEUTIC STUDIES WITH WNV E16 IN 8 WEEK-OLD sIgM -/- MICE AND 5 WEEK-OLD WILD TYPE MICE.

A. 8 week-old sIgM -/- mice were inoculated at day 0 with 100 PFU of WNV via subcutaneous route. At 48 hours after infection (arrow), mice were given 1 mg of mAb against the SARS ORF7a (2E11, IgG2b) or WNV E (WNV E16, IgG2b) protein by intraperitoneal route and followed for survival. N=4 for each group.

B. 5 week-old wild type mice were inoculated at day 0 with 100 PFU of WNV via subcutaneous route. At either 2 or 4 days after infection, mice were given a single dose of 0.5 mg of mAb against the SARS ORF7a (2E11, IgG2b) or WNV E (WNV E16, IgG2b) protein by intraperitoneal route and followed for survival. N=10 for each group. Bracket indicates protection provided by WNV E16.

FIG. 18. FLOW CHART OF SPECIFIC EMBODIMENT

FIG. 19. FLOW CHART OF SPECIFIC EMBODIMENT

Figure 20:
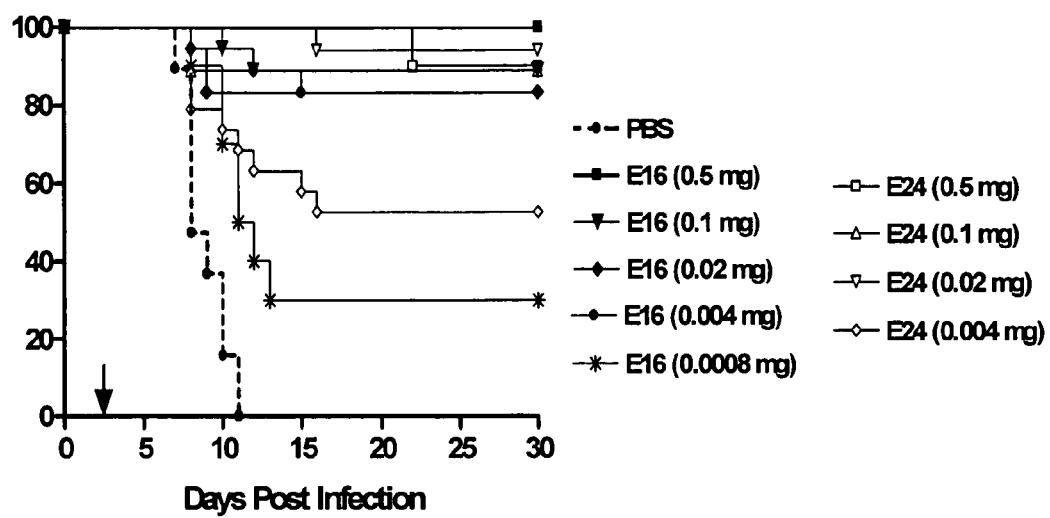

FIG. 20. DOSE RESPONSE OF PROTECTION OF WNV E16 AND E24 MONOCLONAL ANTIBODIES. 5 week pld C576BL/6 mice were infected with $10^2$ PFU of WNV. 48 hours later (hour), mice were inoculated with a single indicated does of monoclonal antibody or PBS and then followed for survival. N=20 for each mice condition.

Figure 21:
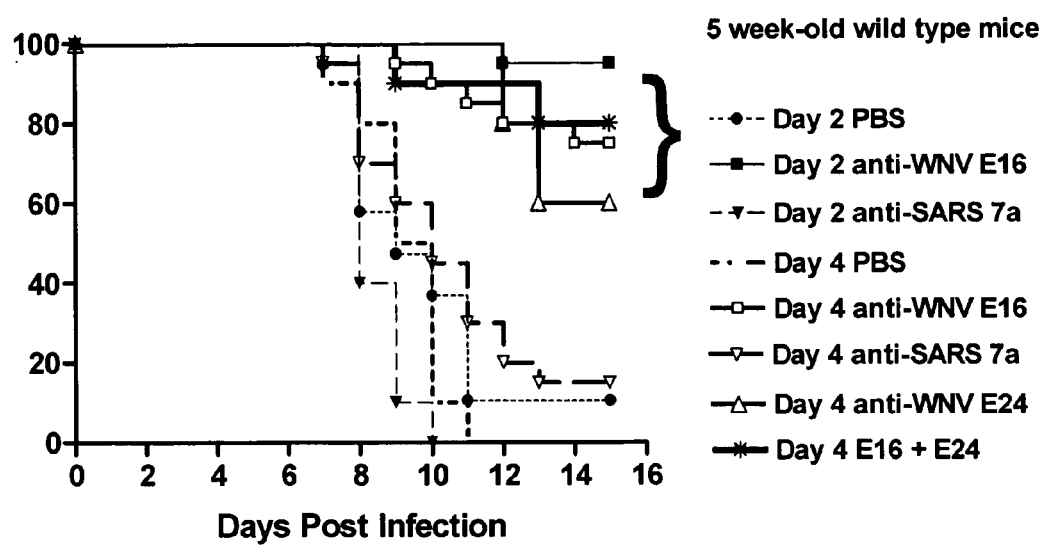

FIG. 21 THERAPEUTIC STUDIES OF WNV E16 AND E24 MONOCLONAL ANTIBODIES. Therapeutic studies WNV E16 and WNV E24 mAbs. 5 week-old C57BL/6 mice were infected with $10^2$ PFU of WNV. At two or four days after infection, mice received a single dose of PBS, anti-SARS 7a (0.5 mg), anti WNV E16 or E24 (0.5 mg), or a combination of anti-WNV E16+E24 (0.25 mg of each). Subsequently, mice were followed for survival. N=20 mice for each condition. The bracket indicates significant (P<0.001) differences from the saline or negative mAb control.

5. DETAILED DESCRIPTION OF THE INVENTION

The present invention is based, in part, on the development of methods for achieving or inducing a prophylactically and/or therapeutically effective response against flaviviral infections, particularly west nile virus (WNV) infections. The invention encompasses methods for achieving or inducing a prophylactically and/or therapeutically effective response against flaviviral infections including, but not limited to, Japanese Encephalitis (JE, e.g., JE SA14-14-2), Dengue (DEN, e.g., any of the Dengue serotypes 1-4); Murray Valley encephalitis, St Louis Encephalitis, West Nile, Tick borne encephalitis, Hepatitis C viruses, Kunjin virus, Powassan virus, Kyasanur Forest Disease virus, yellow fever virus, and Omsk Hemorrhagic Fever Virus. The methods of the instant invention are more effective prophylactically and therapeutically compared to conventional modes of treatment or prophylaxis of flaviviral infections, particularly WNV infections, including, but not limited to, passive administration of immune serum or purified polyclonal antibody, administration of γ-globulin, interferon alpha therapy and IVIG therapies. The methods and compositions of the instant invention are particularly effective for prophylaxis against flaviviral infections in a human population which is at an increased risk of flaviviral infections. In specific preferred embodiments, the methods and compositions of the instant invention are particularly useful to a human population which is at an increased risk for of WNV infection including, but not limited to, human infants, elderly, and human patients with impaired immune system.

The present invention provides methods for treating, preventing, or ameliorating a flaviviral infection by administration of one or more antibodies of the invention. Although not intending to be bound by a particular mechanism of action, antibodies of the invention are more effective than current treatments against flavivrial infections such as, for example, treatment using IVIG for WNV infections from donors with high neutralizing titres. Because IVIG is made from human blood plasma, it has an inherent risk of transmitting an infectious agent. Although the source plasma donors are screened and the plasma is solvent/detergent treated to inactivate viruses such as HIV, virus removal and inactivation must be validated to remove a wide variety of agents as a precaution; and the list of agents that can be transmitted by blood grows with every emerging infection. Even with all these precautions, there is never 100% assurance of elimination of infectious agents. Finally, most preparations have excipients such as human albumin, another blood product, and sucrose, which can increase the risk of adverse events. Another limitation of IVIG can be the large volumes needed, especially in patients with cardiac or renal co-morbidities. In using a specific immune globulin from vaccinated donors, while enriched for antibodies to the target agent, most of the preparation contains unrelated antibodies. The present invention cures the deficiency of current IVIG regimens. Antibodies of the instant invention offer an inherently safer and potentially more efficacious alternative to IVIG for the prevention and treatment of flaviviral infections such as those caused by WNV. Additional benefits of the antibodies of the invention include, but are not limited to, their ability to be grown in tissue culture under defined conditions with chemically defined medium without the addition of animal or human-derived proteins; unlike polyclonal serum, they can be selected for desired properties including epitope specificity, affinity and neutralizing capacity, allowing lower doses; and they can be formulated at high concentration to reduce the volume of administration.

The present invention provides isolated antibodies, preferably monoclonal antibodies (including humanized or other engineered versions of antibodies produced by a hybridoma) or fragments thereof that immunospecifically bind to one or more flaviviral antigens, preferably WNV antigens. Preferably, the isolated antibodies of the invention or fragments thereof immunospecifically bind to one or more flaviviral antigens, preferably WNV antigens, regardless of the strain of the virus. In some embodiments, the isolated antibodies of the invention bind with similar affnities and/or avidities to all WNV strains including lineage I and II strains such as North American West Nile strains including those related to the New York 1999 strain.

In most preferred embodiments, the present invention provides isolated antibodies, preferably monoclonal antibodies, that immunospecifically bind a structural protein of WNV, e.g., E protein, for prevention and/or treatment of WNV infections in mammals. In a specific embodiment, the isolated antibodies of the invention bind to the ectodomain of WNV E protein, as determined by standard methods known to one skilled in the art and exemplified herein, e.g., yeast two hybrid system. In another specific embodiment, the isolated antibodies of the invention bind to domain III of the WNV E protein, comprising amino acids 290 to 415, as determined by standard methods known to one skilled in the art and exemplified herein, e.g., ELISA, immunoprecipitation, immunoblotting. In other specific embodimetns, the isolated antibodies of the invention bind to the viral fusion peptide in domain II, comprising amino acids 98-109, or to other regions in domain I (e.g., amino acids 1-52, 132-193, and 280-290), or domain II (e.g., amino acids 52-132 and 193-280).

The present invention provides methods for treating, preventing, or ameliorating a flaviviral infection by administration of one or more antibodies of the invention. In a specific embodiment, the invention encompasses methods for treating, preventing, or ameliorating a WNV infection comprising administering a first antibody that immunospecifically binds a structural protein of WNV, e.g., E protein, and a second antibody that binds a non-structural protein of WNV, e.g., NS1 protein. In other specific embodiments, the invention encompasses methods for treating, preventing, or ameliorating a WNV infection comprising administering a first antibody that immunospecifically binds an epitope of a structural protein of WNV, e.g., E protein, and a second antibody that binds the same structural protein of WNV but binds at a distinct site.

In other preferred embodiments, the present invention provides isolated monoclonal antibodies that immunospecifically bind a non-structural protein of flaviviral protein particularly WNV, e.g., NS1 protein for prevention and/or treatment of WNV infections in mammals. In some embodiments, the antibodies of the invention bind to one or more epitopes of a structural protein and/or one or more epitopes of a non-structural protein of an WNV. In other embodiments, the present invention also provides antibodies or fragments thereof that differentially or preferentially bind to flaviviral antigens from one strain of the flavivirus versus another strain.

In preferred embodiments, the invention encompasses monoclonal antibodies produced by hybridoma clones E16, E24, or E34, having ATCC Accession Nos. PTA-6050, PTA-6051, and PTA-6052, respectively, variants, or antigen binding fragments thereof, e.g., a humanized or chimerized form, an Fab fragment, etc. In some embodiments, the present invention provides isolated monoclonal antibodies or fragments thereof that immunospecifically bind to one or more WNV antigens, said antibodies or antibody fragments comprising a variable heavy ("VH") chain having an amino acid sequence of any one of the VH domains listed in SEQ ID NOs 4, 8, or 12. The present invention also provides isolated monoclonal antibodies or fragments thereof that immunospecifically bind to one or more WNV antigens, said antibodies or antibody fragments comprising a VL domain having an amino acid sequence of any one of the VL domains listed in SEQ ID NOs 2, 6, or 10. The present invention also provides isolated monoclonal antibodies or fragments thereof that immunospecifically bind to one or more WNV antigens, said antibodies or fragments comprising a VH complementarity determining region ("CDR") having an amino acid sequence of any one of the sequences listed in SEQ ID NOs. 16-17, 20-22, or 26-28. The present invention also provides isolated monoclonal antibodies or fragments thereof that immunospecifically bind to one or more WNV antigens, said antibodies or fragments comprising a VL complementarity determining region ("CDR") having an amino acid sequence of any one of the sequences listed in SEQ ID NOs. 33, 37, or 40-41.

In most preferred embodiments, the invention encompasses antibodies or fragments thereof that have potent neutralizing activity as measured for example using standard methods known in the art and exemplified herein in Example 6.4, e.g., in vitro plaque reduction neutralization titer (PRNT) assay. Although not intending to be bound by a particular mechanims of action the antibodies of the invention may directly neutralize virus or block entry of the virus into the cell, thus treating or preventing viral infections. In some embodiments, the invention encompasses antibodies which immunospecifically bind WNV-E protein such that the $PRNT_{50}$ values are at least 1/500, at least 1/750, at least 1/1000, at least 1/1500, at least 1/2000, at least 1/2500, at least 1/3000, at least 1/3500, at least 1/4000, at least 1/4500, at least 1/5000, at least 1/5500, at least 1/6000, at least 1/6500, at least 1/7000, at least 1/7500, at least 1/8000, at least 1/8500, at least 1/9000, at least 1/9500, or at least 1/10,000, preferably at least 1/10,000 at a concentration of 1 mg/mL. PRNT assays may be done using any method known to one skilled in the art, such as those described in Diamond et al., 2003, J. Virol. 77: 2578-2586, which is incorporated herein by reference in its entirety.

In yet other preferred embodiments, antibodies of the invention have enhanced antibody-dependent complement mediated neutralization of WNV infected virions and trigger lysis of WNV-infected cells more effectively, as determined using standard methods known in the art and exemplified herein, such as complement fixation and cell viability assays. Although not intending to be bound by a particular mechanism of action, the antibodies of the invention have enhanced clinical efficacy, therapeutically and prophylactically as they have enhanced effector functions, neutralize virus attachment, trigger complement mediated lysis, promote clearance from the circulatory systems and prevent emergence of viral resistance. The antibodies of the invention preferably have a potent in vivo inhibitory activity, i.e., protect against WNV infection by at least 50%, at least 60%, at least 70%, at least 80%, at least 90%, at least 99%.

The present invention provides antibodies or fragments thereof which immunospecifically bind to one or more flaviviral antigens particularly WNV antigens and have an apparent dissociation constant of about 1-10 nM, as determined by a sandwich ELISA. The present invention provides antibodies or fragments thereof which immuospecifically bind to one or more flaviviral antigens particularly WNV antigens and have an $K_{on}$ rate of about $1\times10e^4$, about $5\times10^4$, about $1\times10^5$, about $5\times10^5$, about $1\times10^6$, or about $5\times10^6$ and a $K_{off}$ rate of about $1\times10^{-3}$, about $5\times10^{-4}$, about $1\times10^{-4}$, about $5\times10^{-5}$, about $1\times10^{-5}$, about $5\times10^{-6}$, or about $1\times10^{-6}$ as measured by surface plasmon resonance (SPR) using a BIAcore sensor.

The present invention provides antibodies or fragments thereof which immunospecifically bind to one or more flaviviral antigens, particularly WNV antigens, and have a median effective concentration ($EC_{50}$) of less than 1 μg/ml, in an in vitro microneutralization assay. In particular, the present invention provides compositions for use in the prevention, treatment or amelioration of one or more symptoms associated with a flaviviral infection, said compositions comprising one or more antibodies or fragments thereof which immunospecifically bind to one or more one or more flaviviral antigens particularly WNV antigens and have an $EC_{50}$ of less than 0.01 nM, less than 0.025 nM, less than 0.05 nM, less than 0.1 nM, less than 0.25 nM, less than 0.5 nM, less than 0.75 nM, less than 1 nM, less than 1.25 nM, less than 1.5 nM, less than 1.75 nM, or less than 2 nM, in an in vitro microneutralization assay.

The present invention also provides antibodies which immunospecifically bind to one or more flaviviral antigens, particularly WNV antigens, and have increased in vivo half-lives (by for example 30 days) relative to known antibodies. In particular, the present invention encompasses antibodies which immunospecifically bind to one or more flaviviral antigens, particularly WNV antigens, and have increased in vivo half-lives relative to known antibodies, said increased half-lives resulting from one or more modifications (e.g., substitutions, deletions, or insertions) in amino acid residues identified to be involved in the interaction of the Fc domain of said antibodies and the FcRn receptor. The present invention also encompasses pegylated antibodies and fragments thereof which immunospecifically bind to one or more flaviviral antigens, particularly WNV antigens, and have increased in vivo half-lives relative to known antibodies. The increased in vivo half-lives of antibodies or fragments thereof which immunospecifically bind to one or more flaviviral antigens, particularly WNV antigens, reduce the dosage and/or frequency of administration of said antibodies or fragments thereof to a subject.

The present invention encompasses the production of novel monoclonal antibodies with specificities for one or more WNV antigens. In particular, the invention provides a method for producing monoclonal antibodies that specifically bind one or more WNV antigens, said method comprising: (a) immunizing one or more BALB/c mice with purified WNV proteins, e.g., NS1, E protein, or an immunogenic fragment thereof using a carbohydrate and lipid based adjuvant; (b) measuring the polyclonal antibody response using a solid phase ELISA based assay; (c) producing hybridoma cells lines from spleen cells of said one or more mice; (d) screening said hybridoma cell lines for one or more hybridoma cell lines that produce antibodies that specifically bind the particular WNV protein; (e) selecting candidate immune mice; (f) priming a single mouse with a high-titer polyclonal (1/10,000) response intravenously with purified E or NS1 proteins (g) harvesting splenocytes and fusing then to the non-secreting P3X63Ag8.6.5.3 myeloma according to standard protocols (Harlow et al., 1988. Antibodies, A laboratory manual. Cold Spring Harbor Laboratory, Cold Spring Harbor). The invention encompasses any antibody produced by said method.

In a preferred embodiment, the invention provides a monoclonal antibody produced by clones E16, E24, or E34, having ATCC Accession Nos. PTA-6050, PTA-6051, and PTA-6052, respectively. In another embodiment, the invention provides an isolated antibody or a fragment thereof that competes for binding with a monoclonal antibody produced by clones E16, E24, or E34. Furthermore, the invention provides hybridoma cell lines E16, E24, or E34, having ATCC Accession Nos. PTA-6050, PTA-6051, and PTA-6052, respectively. In other preferred embodiments, the invention encompasses monoclonal antibodies produced by hybridoma clones E16, E24, or E34, having ATCC Accession Nos. PTA-6050, PTA-6051, and PTA-6052, respectively, variants, or antigen binding fragments thereof, e.g., a humanized or chimerized form, an Fab fragment, etc.

The methods of the invention also encompass polynucleotides that encode the antibodies of the invention. In one embodiment, the invention provides an isolated nucleic acid sequence encoding a heavy chain or a light chain of an antibody or a fragment thereof that specifically binds one or more flaviviral antigens, particularly WNV antigens. The invention also relates to a vector comprising said nucleic acid. The invention further provides a vector comprising a first nucleic acid molecule encoding a heavy chain and a second nucleic acid molecule encoding a light chain, said heavy chain and light chain being of an antibody or a fragment thereof that specifically binds one or more flaviviral antigens, particularly WNV antigens. In one specific embodiment, said vector is an expression vector. The invention further provides host cells containing the vectors of or polynucleotides encoding the antibodies of the invention. Preferably, the invention encompasses polynucleotides encoding heavy and light chains of the antibodies produced by the deposited hybridoma clones, having ATCC accession numbers PTA-6050, PTA-6051, and PTA-6052, respectively, or portions thereof, e.g., CDRs, variable domains, etc. and humanized versions thereof.

The invention further provides methods for the production of antibodies of the invention or fragments thereof. The antibodies of the invention or fragments thereof can be produced by any method known in the art for the production of antibodies, in particular, by secretion from cultured hybridoma cells, chemical synthesis or by recombinant expression techniques known in the art. In one specific embodiment, the invention relates to a method for recombinantly producing a flaviviral antigen-specific antibody, said method comprising: (i) culturing under conditions suitable for the expression of said antibody in a medium, a host cell containing a first nucleic acid molecule, operably linked to a heterologous promoter and a second nucleic acid operably linked to the same or a different heterologous promoter, said first nucleic acid and second nucleic acid encoding a heavy chain and a light chain, respectively, of an antibody or a fragment thereof that specifically binds one or more flaviviral antigens; and (ii) recovery of said antibody from said medium.

Preferably, the antibodies of the invention are monoclonal antibodies, and more preferably, humanized or human antibodies. In one specific preferred embodiment, the antibodies of the invention bind to the WNV E protein. In another specific embodiment, the antibodies of the invention specifically or selectively recognize one or more epitopes of WNV E protein. Another embodiment of the invention encompasses the use of phage display technology, DNA shuffling, or any other similar method known to one skilled in the art, to increase the affinity of the antibodies of the invention for WNV E protein. In one specific preferred embodiment, the antibodies of the invention bind to the WNV NS1 protein. In another specific embodiment, the antibodies of the invention specifically or selectively recognize one or more epitopes of WNV NS1 protein. Another embodiment of the invention encompasses the use of phage display technology to increase the affinity of the antibodies of the invention for WNV NS1 protein. Any screening method known in the art can be used to identify mutant antibodies with increased avidity for WNV E protein (e.g., ELISA). In another specific embodiment, antibodies of the invention are screened using antibody screening assays well known in the art (e.g., BIACORE assays) to identify antibodies with $K_{off}$ rate of about $1\times10^{-3}$, about $5\times10^{-4}$, about $1\times10^{-4}$, about $5\times10^{-5}$, about $1\times10^{-5}$, about $5\times10^{-6}$, or about $1\times10^{-6}$.

The invention encompasses the use of the antibodies of the invention to detect the presence of one or more flaviviral antigens specifically in a biological sample.

The present invention provides methods of preventing, treating and ameliorating one or more symptoms associated with flaviviral infection, particularly WNV infection, in a subject comprising administering to said subject one or more antibodies or fragments thereof which immunospecifically bind to one or more flaviviral antigens, particularly WNV antigens, with high affinity and/or high avidity. The antibodies of the invention are useful for prevention or treatment of a flaviviral infection for example, in one embodiment, as a single agent therapy.

The invention further provides a pharmaceutical composition comprising (i) a therapeutically or prophylactically effective amount of the antibody or a fragment thereof that specifically binds one or more flaviviral antigens, e.g., WNV antigen; and (ii) a pharmaceutically acceptable carrier.

The present invention encompasses methods of delivering one or more antibodies or fragments thereof which immunospecifically bind to one or more flaviviral antigens, e.g., WNV antigens, directly to the site of flaviviral infection.

The present invention provides antibodies or fragments thereof which immunospecifically bind to one or more flaviviral antigens, particularly WNV antigens, and have an association rate constant or $k_{on}$ rate (antibody (Ab)+antigen $(Ag)^{k_{on}} \rightarrow$Ab-Ag) of at least $1\times10^4$, about $5\times10^4$, about $1\times10^5$, about $5\times10^5$, about $1\times10^6$, or about $5\times10^6$. In particular, the present invention provides compositions for use in the prevention, treatment or amelioration of one or more symptoms associated with a flaviviral infection, said compositions comprising one or more antibodies or fragments thereof which immunospecifically bind to one or more one or more flaviviral antigens, particularly WNV antigens, and have an a $k_{on}$ rate of at least $1\times10^4$, about $5\times10^4$, about $1\times10^5$, about $5\times10^5$, about $1\times10^6$, or about $5\times10^6$.

In another embodiment, the invention provides a method of diagnosis of a flaviviral infection in a subject comprising: (i) contacting a biological sample from said subject with an effective amount of an antibody of the invention; and (ii) detecting binding of said antibody or a fragment thereof, wherein detection of said detectable marker above a background or standard level indicates that said subject has a flaviviral infection.

5.1 Antibodies

The present invention provides isolated antibodies, preferably monoclonal antibodies or fragments thereof, that immunospecifically bind to one or more flaviviral antigens, preferably WNV antigens. Preferably, the isolated antibodies of the invention or fragments thereof immunospecifically bind to one or more flaviviral antigens, preferably WNV antigens, regardless of the strain of the virus. In some embodiments, the isolated antibodies of the invention bind with similar affinities and/or avidities to all WNV strains including lineage I and II strains such as North American strains (e.g., the New York 1999 and related strains).

In most preferred embodiments, the present invention provides isolated antibodies, preferrably monoclonal antibodies, that immunospecifically bind a structural protein of WNV, e.g., E protein, for prevention and/or treatment of WNV infections in avians or mammals, particularly humans. In a specific embodiment, the isolated antibodies of the invention bind to the ectodomain of WNV E protein, as determined by standard methods known to one skilled in the art and exemplified herein, e.g., ELISA, flow cytometry, immunoprecipitation, immunoblot. In another specific embodiment, the isolated antibodies of the invention bind to domain III of the WNV E protein, comprising amino acids 290 to 415, as determined by standard methods known to one skilled in the art and exemplified herein, e.g., ELISA, immunoprecipitation, immunoblotting.

In other preferred embodiments, the present invention provides isolated antibodies, preferably monoclonal antibodies that immunospecifically bind a non-structural protein of WNV, e.g., NS1 protein for prevention and/or treatment of WNV infections in mammals. In some embodiments, the antibodies of the invention bind to one or more epitopes of a structural protein and/or one or more epitopes of a non-structural protein of an WNV. In other embodiments, the present invention also provides antibodies or fragments thereof that differentially or preferentially bind to flaviviral antigens from one strain of the flavivirus versus another strain.

In some embodiments, the present invention provides isolated monoclonal antibodies or fragments thereof that immunospecifically bind to one or more WNV antigens, said antibodies or antibody fragments comprising a variable heavy ("VH") chain having an amino acid sequence of any one of the VH domains listed in SEQ ID NOs. 4, 8, or 12. The present invention also provides isolated monoclonal antibodies or fragments thereof that immunospecifically bind to one or more WNV antigens, said antibodies or antibody fragments comprising a VL domain having an amino acid sequence of any one of the VL domains listed in SEQ ID NOs. 2, 6, or 10. The present invention also provides isolated monoclonal antibodies or fragments thereof that immunospecifically bind to one or more WNV antigens, said antibodies or fragments comprising an amino acid sequence of any one of sequences listed in Table 1.

The present invention also provides for antibodies or fragments thereof that immunospecifically bind to one or more flaviviral antigens, particularly WNV antigens, said antibodies or antibody fragments comprising the amino acid sequence listed in any of SEQ ID NOs. 13-43, 4, 8, 12, 2, 6, or 10 with one or more amino acid residue substitutions in one or more VL CDRs and/or one or more VH CDRs. In accordance with this embodiment, the amino acid residue substitutions can be conservative or non-conservative. The antibody or antibody fragment generated by introducing substitutions in the VH domain, VH CDRs, VL domain and/or VL CDRs of the antibodies of the invention can be tested in vitro and in vivo, for example, for its ability to bind to flaviviral antigens, particularly WNV antigens, for its ability to neutralize a flavivirus, particularly WNV, or for its ability to prevent, treat or ameliorate one or more symptoms associated with a flavivirus, particularly WNV, infection.

In one embodiment of the present invention, antibodies or fragments thereof comprise a VH CDR1 having the amino acid sequence of any of SEQ ID NOs. 16-17. In another embodiment, antibodies or fragments thereof comprise a VH CDR2 having the amino acid sequence of any of SEQ ID Nos. 20-22. In another embodiment, antibodies comprise a VH CDR3 having the amino acid sequence of any of SEQ ID Nos. 26-28.

In one embodiment of the present invention, antibodies or fragments thereof comprise a VL CDR1 having the amino acid sequence of SEQ ID NO. 33. In another embodiment, antibodies or fragments thereof comprise a VL CDR2 having the amino acid sequence of SEQ ID NO. 37. In another embodiment, antibodies comprise a VL CDR3 having the amino acid sequence of any of SEQ ID NOs. 40-41.

The present invention also provides antibodies or fragments thereof that immunospecifically bind to one or more WNV antigens, said antibodies or antibody fragments comprising a VH domain disclosed herein combined with a VL domain disclosed herein, or other VL domain. The present invention further provides antibodies or fragments thereof that immunospecifically bind to one or more WNV antigens, said antibodies or fragments comprising a VL domain disclosed herein combined with a VH domain disclosed herein, or other VH domain.

The present invention also provides antibodies or fragments thereof comprising one or more VH CDRs and one or more VL CDRs listed in SEQ ID NOs. 16-17, 20-22, 26-28, 33, 37, or 40-41. In particular, the invention provides for an antibody or fragment thereof comprising a VH CDR1 and a VL CDR1, a VH CDR1 and a VL CDR2, a VH CDR1 and a VL CDR3, a VH CDR2 and a VL CDR1, VH CDR2 and VL CDR2, a VH CDR2 and a VL CDR3, a VH CDR3 and a VH CDR1, a VH CDR3 and a VL CDR2, a VH CDR3 and a VL CDR3, or any combination thereof of the VH CDRs and VL CDRs listed in SEQ ID NOs. 16-17, 20-22, 26-28, 33, 37, or 40-41. The invention also provides for an antibody or fragment thereof comprising a VH CDR1 and a VL CDR1, a VH CDR1 and a VL CDR2, a VH CDR1 and a VL CDR3, a VH CDR2 and a VL CDR1, VH CDR2 and VL CDR2, a VH CDR2 and a VL CDR3, a VH CDR3 and a VH CDR1, a VH CDR3 and a VL CDR2, a VH CDR3 and a VL CDR3, or any combination thereof of the VH CDRs and VL CDRs listed in SEQ ID NOs. 16-17, 20-22, 26-28, 33, 37, or 40-41. The invention also provides for an antibody or fragment thereof comprising a VH CDR1 and a VL CDR1, a VH CDR1 and a VL CDR2, a VH CDR1 and a VL CDR3, a VH CDR2 and a VL CDR1, VH CDR2 and VL CDR2, a VH CDR2 and a VL CDR3, a VH CDR3 and a VH CDR1, a VH CDR3 and a VL CDR2, a VH CDR3 and a VL CDR3, or any combination thereof of the VH CDRs and VL CDRs listed in SEQ ID NOs. 16-17, 20-22, 26-28, 33, 37, or 40-41.

In another embodiment, an antibody or fragment thereof that immunospecifically binds to a WNV antigen comprises an amino acid sequence of a VH domain that is at least 35%, at least 40%, at least 45%, at least 50%, at least 55%, at least 60%, at least 65%, at least 70%, at least 75%, at least 80%, at least 85%, at least 90%, at least 95%, or at least 99% identical to any one of the VH domains listed in SEQ ID NOs. 4, 8, or 12. In another embodiment, an antibody or fragment thereof that immunospecifically binds to a WNV antigen comprises an amino acid sequence of one or more VH CDRs that are at least 35%, at least 40%, at least 45%, at least 50%, at least 55%, at least 60%, at least 65%, at least 70%, at least 75%, at least 80%, at least 85%, at least 90%, at least 95%, or at least 99% identical to any of the VH CDRs listed in SEQ ID NOs. 16-17, 20-22, or 26-28.

In another embodiment, an antibody or fragment thereof that immunospecifically binds to a WNV antigen comprises an amino acid sequence of a VL domain that is at least 35%, at least 40%, at least 45%, at least 50%, at least 55%, at least 60%, at least 65%, at least 70%, at least 75%, at least 80%, at least 85%, at least 90%, at least 95%, or at least 99% identical to any one of the VL domains listed in SEQ ID NOs. 2, 6, or 10. In another embodiment, an antibody or fragment thereof that immunospecifically binds to a WNV antigen comprises an amino acid sequence of one or more VL CDRs that are at least 35%, at least 40%, at least 45%, at least 50%, at least 55%, at least 60%, at least 65%, at least 70%, at least 75%, at least 80%, at least 85%, at least 90%, at least 95%, or at least 99% identical to any of the VL CDRs listed in SEQ ID NOs. 33, 37, or 40-41.

In most preferred embodiments, the invention encompasses antibodies or fragments thereof that have potent neutralizing activity as measured for example using standard methods known in the art and exemplified herein, e.g., in vivo plaque reduction neutralization titer (PRNT) assay. Although not intending to be bound by a particular mechanims of action the antibodies of the invention may directly neutralize virus or block entry of the virus into the cell, thus preventing viral infections. In some embodiments, the invention encompasses antibodies which immunospecifically bind WNV-E protein such that the $PRNT_{50}$ values are at least ⅟500, preferably at least ⅟10,000 at a concentration of 1 mg/mL.

In yet other preferred embodiments, antibodies of the invention have enhanced antibody-dependent complement mediated neutralization of WNV infected virions and trigger lysis of WNV-infected cells more effectively, as determined using standard methods known in the art and exemplified herein such as complement fixation and viability assays Although not intending to be bound by a particular mechanism of action, the antibodies of the invention have enhanced clinical efficacy, therapeutically and prophylactically as they have enhanced effector functions, neutralize virus attachment, trigger complement mediated lysis, promote clearance from the circulatory systems and prevent emergence of viral resistance. The antibodies of the invention preferably have a potent in vivo inhibitory activity, i.e., protect against WNV infection by at least 50%, at least 60%, at least 70%, at least 80%, at least 90%, at least 99%.

The present invention provides antibodies or fragments thereof which immunospecifically bind to one or more flaviviral antigens, particularly WNV antigens, and have an apparent dissociation constant of about 1-10 nM, as determined by a sandwich ELISA. The present invention provides antibodies or fragments thereof which immuospecifically bind to one or more flaviviral antigens particularly WNV antigens and have an apparent dissociation constant of about 1-10 nM as measured by surface plasmon resonance (SPR) using a BIAcore sensor.

The present invention provides antibodies or fragments thereof which immunospecifically bind to one or more flaviviral antigens, particularly WNV antigens and have a $k_{off}$ rate (antibody (Ab)+antigen (Ag)$^{K_{off}}$→Ab-Ag of less than $10^{-1}s^{-1}$, less than $5\times10^{-1}s^{-1}$, less than $10^{-2}s^{-1}$, less than $5\times10^{-2}s^{-1}$, less than $10^{-3}s^{-1}$, less than $5\times10^{-3}s^{-1}$, less than $10^{-4}s^{-1}$, less than $5\times10^{-4}s^{-1}$, less than $10^{-5}s^{-1}$, less than $5\times10^{-5}s^{-1}$, less than $10^{-6}s^{-1}$, less than $5\times10^{-6}s^{-1}$, less than $10^{-7}s^{-1}$, less than $5\times10^{-7}s^{-1}$, less than $10^{-8}s^{-1}$, less than $5\times10^{-8}s^{-1}$, less than $10^{-9}s^{-1}$, less than $5\times10^{-9}s^{-1}$, or less than $10^{-10}s^{-1}$. The present invention provides antibodies or fragments thereof which immunospecifically bind to one or more flaviviral antigens, particularly WNV antigens, and have a $k_{off}$ rate (antibody (Ab)+antigen (Ag)$^{K_{off}}$→Ab-Ag of about $1\times10^{-3}$, about $5\times10^{-4}$, about $1\times10^{-4}$, about $5\times10^{-5}$, about $1\times10^{-5}$, about $5\times10^{-6}$, or about $1\times10^{-6}$. The present invention provides antibodies or fragments thereof which immunospecifically bind to one or more flaviviral antigens, particularly WNV antigens, and have a $K_{on}$ rate of about $1\times10^{4}$, about $5\times10^{4}$, about $1\times10^{5}$, about $5\times10^{5}$, about $1\times10^{6}$, or about $5\times10^{6}$.

The present invention provides antibodies or fragments thereof which immunospecifically bind to one or more flaviviral antigens, particularly WNV antigens, and have a median effective concentration ($EC_{50}$) of less than 1 μg/ml, in an in vitro microneutralization assay. In particular, the present invention provides compositions for use in the prevention, treatment or amelioration of one or more symptoms associated with a flaviviral infection, said compositions comprising one or more antibodies or fragments thereof which immunospecifically bind to one or more one or more flaviviral antigens, particularly WNV antigens, and have an $EC_{50}$ of less than 0.01 nM, less than 0.025 nM, less than 0.05 nM, less than 0.1 nM, less than 0.25 nM, less than 0.5 nM, less than 0.75 nM, less than 1 nM, less than 1.25 nM, less than 1.5 nM, less than 1.75 nM, or less than 2 nM, in an in vitro microneutralization assay.

In one particular embodiment, the antibody is a mouse monoclonal antibody produced by clones E16, E24, or E34, having ATCC Accession Nos. PTA-6050, PTA-6051, and PTA-6052, respectively. Hybridomas producing antibodies of the invention, i.e., E16, E24, and E34, have been deposited with the American Type Culture Collection (10801 University Blvd., Manassas, Va. 20110-2209) on Jun. 4, 2004 under the provisions of the Budapest Treaty on the International Recognition of the Deposit of Microorganisms for the Purposes of Patent Procedures, and assigned ATCC Accession Nos. PTA-6050, PTA-6051, and PTA-6052, respectively and are incorporated herein by reference. In a specific embodiment, the invention encompasses an antibody with the heavy chain having the amino acid sequence of SEQ ID Nos. 4, 8, or 12 and the light chain having the amino acid sequence of SEQ ID Nos. 2, 6, or 10. In a preferred embodiment, the antibodies of the invention are human or have been humanized, preferably a humanized version of the antibody produced by clones E16, E24, or E34.

The present invention also provides antibodies which immunospecifically bind to one or more flaviviral antigens, particularly WNV antigens, and have increased in vivo half-lives relative to known antibodies. The increased in vivo half-lives of antibodies or fragments thereof which immunospecifically bind to one or more flaviviral antigens, particularly WNV antigens, reduce the dosage and/or frequency of administration of said antibodies or fragments thereof to a subject. In particular, the present invention encompasses antibodies which immunospecifically bind to one or more flaviviral antigens, particularly WNV antigens, and have increased in vivo half-lives relative to known antibodies, said increased half-lives resulting from one or more modifications (e.g., substitutions, deletions, or insertions) in amino acid residues identified to be involved in the interaction of the Fc domain of said antibodies and the FcRn receptor. The present invention also encompasses pegylated antibodies and fragments thereof which immunospecifically bind to one or more flaviviral antigens, particularly WNV antigens, and have increased in vivo half-lives relative to known antibodies. The increased in vivo half-lives of antibodies or fragments thereof which immunospecifically bind to one or more flaviviral antigens, particularly WNV antigens, reduce the dosage and/or frequency of administration of said antibodies or fragments thereof to a subject.

Antibodies of the invention include, but are not limited to, monoclonal antibodies, synthetic antibodies, recombinantly produced antibodies, bispecific, multispecific antibodies, human antibodies, humanized antibodies, chimeric antibodies, camelized antibodies, single-chain Fvs (scFv), single chain antibodies, Fab fragments, F(ab') fragments, disulfide-linked Fvs (sdFv), intrabodies, and epitope-binding fragments of any of the above. In particular, antibodies used in the methods of the present invention include immunoglobulin molecules and immunologically active portions of immunoglobulin molecules, i.e., molecules that contain an antigen binding site that immunospecifically binds to one or more flaviviral antigens, particularly WNV antigens. Antibodies of the invention may bind to one or more distinct sites of a flaviviral antigen.

The antibodies used in the methods of the invention may be from any animal origin including birds and mammals (e.g., human, non-human primate, murine, donkey, sheep, rabbit, goat, guinea pig, camel, horse, or chicken). Preferably, the antibodies are human or humanized monoclonal antibodies.

As used herein, "human" antibodies include antibodies having the amino acid sequence of a human immunoglobulin and include antibodies isolated from human immunoglobulin libraries or libraries of synthetic human immunoglobulin coding sequences or from mice that express antibodies from human genes.

The antibodies used in the methods of the present invention may be monospecific, bispecific, trispecific or of greater multispecificity. Multispecific antibodies may immunospecifically bind to different epitopes of flaviviral antigen, e.g., WNV antigen or immunospecifically bind to both an epitope of a flaviviral antigen as well a heterologous epitope, such as a heterologous polypeptide or solid support material. See, e.g., International Publication Nos. WO 93/17715, WO 92/08802, WO 91/00360, and WO 92/05793; Tutt et al., 1991, *J. Immunol.* 147:60-69; U.S. Pat. Nos. 4,474,893, 4,714,681, 4,925,648, 5,573,920, and 5,601,819; and Kostelny et al., 1992, *J. Immunol.* 148:1547-1553; Todorovska et al., 2001 *Journal of Immunological Methods,* 248:47-66, all of which are incorporated herein by reference in their entireties.

In a specific embodiment, an antibody used in the methods of the present invention is an antibody or an antigen-binding fragment thereof (e.g., comprising one or more complementarily determining regions (CDRs), preferably all 6 CDRs) of an antibody produced by clones E16, E24, or E34, having ATCC Accession Nos. PTA-6050, PTA-6051, and PTA-6052, respectively. In another embodiment, an antibody used in the methods of the present invention binds to the same epitope as a mouse monoclonal antibody produced from clones E16, E24, or E34, having ATCC Accession Nos. PTA-6050, PTA-6051, and PTA-6052, respectively and/or competes with a mouse monoclonal antibody produced from clones E16, E24, or E34, having ATCC Accession Nos. PTA-6050, PTA-6051, and PTA-6052, respectively as determined, e.g., in an ELISA assay or other appropriate competitive immunoassay.

The antibodies used in the methods of the invention include derivatives that are modified, i.e, by the covalent attachment of any type of molecule to the antibody such that covalent attachment. For example, but not by way of limitation, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to, specific chemical cleavage, acetylation, formylation, metabolic synthesis of tunicamycin, etc. Additionally, the derivative may contain one or more non-classical amino acids.

For some uses, including in vivo use of antibodies in humans and in vitro detection assays, it may be preferable to use human, chimeric or humanized antibodies. Completely human antibodies are particularly desirable for therapeutic treatment of human subjects. Human antibodies can be made by a variety of methods known in the art including phage display methods described above using antibody libraries derived from human immunoglobulin sequences. See also U.S. Pat. Nos. 4,444,887 and 4,716,111; and International Publication Nos. WO 98/46645, WO 98/50433, WO 98/24893, WO 98/16654, WO 96/34096, WO 96/33735, and WO 91/10741; each of which is incorporated herein by reference in its entirety.

Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered nonfunctional separately or simultaneously with the introduction of human immunoglobulin loci by homologous recombination. In particular, homozygous deletion of the $J_H$ region prevents endogenous antibody production. The modified embryonic stem cells are expanded and microinjected into blastocysts to produce chimeric mice. The chimeric mice are then bred to produce homozygous offspring which express human antibodies. The transgenic mice are immunized using conventional methodologies with a selected antigen, e.g., all or a portion of a polypeptide of the invention. Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar (1995, *Int. Rev. Immunol.* 13:65-93, which is incorporated herein by reference in its entirety). For a detailed discussion of this technology for producing human antibodies and human monoclonal antibodies and protocols for producing such antibodies, see, e.g., International Publication Nos. WO 98/24893, WO 96/34096, and WO 96/33735; and U.S. Pat. Nos. 5,413,923, 5,625,126, 5,633,425, 5,569,825, 5,661,016, 5,545,806, 5,814,318, and 5,939,598, which are incorporated by reference herein in their entirety. In addition, companies such as Abgenix, Inc. (Freemont, Calif.) and Medarex (Princeton, N.J.) can be engaged to provide human antibodies directed against a selected antigen using technology similar to that described above.

A chimeric antibody is a molecule in which different portions of the antibody are derived from different immunoglobulin molecules such as antibodies having a variable region derived from a non-human antibody and a human immunoglobulin constant region. Methods for producing chimeric antibodies are known in the art. See e.g., Morrison, 1985, *Science* 229:1202; Oi et al., 1986, *BioTechniques* 4:214; Gillies et al., 1989, *J. Immunol. Methods* 125:191-202; and U.S. Pat. Nos. 6,311,415, 5,807,715, 4,816,567, and 4,816,397, which are incorporated herein by reference in their entireties. Chimeric antibodies comprising one or more CDRs from a non-human species and framework regions from a human immunoglobulin molecule can be produced using a variety of techniques known in the art including, for example, CDR-grafting (EP 239,400; International Publication No. WO 91/09967; and U.S. Pat. Nos. 5,225,539, 5,530,101, and 5,585,089), veneering or resurfacing (EP 592,106; EP 519, 596; Padlan, 1991, *Molecular Immunology* 28(4/5):489-498; Studnicka et al., 1994, *Protein Engineering* 7:805; and Roguska et al., 1994, *PNAS* 91:969), and chain shuffling (U.S. Pat. No. 5,565,332). Each of the above-identified references is incorporated herein by reference in its entirety.

Often, framework residues in the framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions (See, e.g., U.S. Pat. No. 5,585,089; and Riechmann et al., 1988, *Nature* 332:323, which are incorporated herein by reference in their entireties).

A humanized antibody is an antibody, a variant or a fragment thereof which is capable of binding to a predetermined antigen and which comprises a framework region having substantially the amino acid sequence of a human immunoglobulin and a CDR having substantially the amino acid sequence of a non-human immunoglobulin. A humanized antibody comprises substantially all of at least one, and typically two, variable domains in which all or substantially all of the CDR regions correspond to those of a non-human immunoglobulin (i.e., donor antibody) and all or substantially all of the framework regions are those of a human immunoglobulin consensus sequence. Preferably, a humanized antibody also comprises at least a portion of an immunoglobulin constant region (Fc), typically that of a human immunoglobulin. Ordinarily, the antibody will contain both the light chain as well as at least the variable domain of a heavy chain. The antibody also may include the CH1, hinge, CH2, CH3, and CH4 regions of the heavy chain. The humanized antibody can be selected from any class of immunoglobulins, including IgM, IgG, IgD, IgA and IgE, and any isotype, including $IgG_1$, $IgG_2$, $IgG_3$ and $IgG_4$. Usually the constant domain is a complement fixing constant domain where it is desired that the humanized antibody exhibit cytotoxic activity, and the class is typically $IgG_1$. Where such cytotoxic activity is not desirable, the constant domain may be of the $IgG_2$ class. The humanized antibody may comprise sequences from more than one class or isotype, and selecting particular constant domains to optimize desired effector functions is within the ordinary skill in the art. The framework and CDR regions of a humanized antibody need not correspond precisely to the parental sequences, e.g., the donor CDR or the consensus framework may be mutagenized by substitution, insertion or deletion of at least one residue so that the CDR or framework residue at that site does not correspond to either the consensus or the import antibody. Such mutations, however, will not be extensive. Usually, at least 75% of the humanized antibody residues will correspond to those of the parental framework region (FR) and CDR sequences, more often 90%, and most preferably greater than 95%. Humanized antibodies can be produced using variety of techniques known in the art, including but not limited to, CDR-grafting (European Patent No. EP 239,400; International Publication No. WO 91/09967; and U.S. Pat. Nos. 5,225,539, 5,530,101, and 5,585,089), veneering or resurfacing (European Patent Nos. EP 592,106 and EP 519,596; Padlan, 1991, *Molecular Immunology* 28(4/5):489-498; Studnicka et al., 1994, *Protein Engineering* 7(6):805-814; and Roguska et al., 1994, *PNAS* 91:969-973), chain shuffling (U.S. Pat. No. 5,565,332), and techniques disclosed in, e.g., U.S. Pat. Nos. 6,407,213, 5,766,886, 5,585,089, International Publication No. WO 9317105, Tan et al., 2002, *J. Immunol.* 169:1119-25, Caldas et al., 2000, *Protein Eng.* 13:353-60, Morea et al., 2000, *Methods* 20:267-79, Baca et al., 1997, *J. Biol. Chem.* 272:10678-84, Roguska et al., 1996, *Protein Eng.* 9:895-904, Couto et al., 1995, *Cancer Res.* 55 (23 Supp):5973s-5977s, Couto et al., 1995, *Cancer Res.* 55:1717-22, Sandhu, 1994, *Gene* 150:409-10, Pedersen et al., 1994, *J. Mol. Biol.* 235:959-73, Jones et al., 1986, *Nature* 321:522-525, Riechmann et al., 1988, *Nature* 332:323, and Presta, 1992, *Curr. Op. Struct. Biol.* 2:593-596. Often, framework residues in the framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions (See, e.g., U.S. Pat. No. 5,585,089; and Riechmann et al., 1988, *Nature* 332:323, which are incorporated herein by reference in their entireties).

Further, the antibodies of the invention can, in turn, be utilized to generate anti-idiotype antibodies using techniques well known to those skilled in the art (See, e.g., Greenspan & Bona, 1989, *FASEB J.* 7:437-444; and Nissinoff, 1991, *J. Immunol.* 147:2429-2438). The invention provides methods employing the use of polynucleotides comprising a nucleotide sequence encoding an antibody of the invention or a fragment thereof.

The present invention encompasses single domain antibodies, including camelized single domain antibodies (See e.g., Muyldermans et al., 2001, *Trends Biochem. Sci.* 26:230; Nuttall et al., 2000, *Cur. Pharm. Biotech.* 1:253; Reichmann and Muyldermans, 1999, *J. Immunol. Meth.* 231:25; International Publication Nos. WO 94/04678 and WO 94/25591; U.S. Pat. No. 6,005,079; which are incorporated herein by reference in their entireties). In one embodiment, the present invention provides single domain antibodies comprising two VH domains with modifications such that single domain antibodies are formed.

The methods of the present invention also encompass the use of antibodies or fragments thereof that have half-lives (e.g., serum half-lives) in a mammal, preferably a human, of greater than 15 days, preferably greater than 20 days, greater than 25 days, greater than 30 days, greater than 35 days, greater than 40 days, greater than 45 days, greater than 2 months, greater than 3 months, greater than 4 months, or greater than 5 months. The increased half-lives of the antibodies of the present invention or fragments thereof in a mammal, preferably a human, results in a higher serum titer of said antibodies or antibody fragments in the mammal, and thus, reduces the frequency of the administration of said antibodies or antibody fragments and/or reduces the concentration of said antibodies or antibody fragments to be administered. Antibodies or fragments thereof having increased in vivo half-lives can be generated by techniques known to those of skill in the art. For example, antibodies or fragments thereof with increased in vivo half-lives can be generated by modifying (e.g., substituting, deleting or adding) amino acid residues identified as involved in the interaction between the Fc domain and the FcRn receptor. The antibodies of the invention may be engineered by methods described in Ward et al. to increase biological half-lives (See U.S. Pat. No. 6,277,375 B1, which is incorporated herein by reference in its entirety). For example, antibodies of the invention may be engineered in the Fc-hinge domain to have increased in vivo or serum half-lives.

Antibodies or fragments thereof with increased in vivo half-lives can be generated by attaching to said antibodies or antibody fragments polymer molecules such as high molecular weight polyethyleneglycol (PEG). PEG can be attached to said antibodies or antibody fragments with or without a multifunctional linker either through site-specific conjugation of the PEG to the N- or C-terminus of said antibodies or antibody fragments or via epsilon-amino groups present on lysine residues. Linear or branched polymer derivatization that results in minimal loss of biological activity will be used. The degree of conjugation will be closely monitored by SDS-PAGE and mass spectrometry to ensure proper conjugation of PEG molecules to the antibodies. Unreacted PEG can be separated from antibody-PEG conjugates by, e.g., size exclusion or ion-exchange chromatography.

The antibodies of the invention may also be modified by the methods and coupling agents described by Davis et al. (See U.S. Pat. No. 4,179,337, which is incorporated herein by reference in its entirety) in order to provide compositions that can be injected into the mammalian circulatory system with substantially no immunogenic response.

The present invention also encompasses the use of antibodies or antibody fragments comprising the amino acid sequence of any of the antibodies of the invention with mutations (e.g., one or more amino acid substitutions) in the framework or variable regions. Preferably, mutations in these antibodies maintain or enhance the avidity and/or affinity of the antibodies for the particular antigen(s) to which they immunospecifically bind. Standard techniques known to those skilled in the art (e.g., immunoassays) can be used to assay the affinity of an antibody for a particular antigen.

The present invention encompasses antibodies comprising modifications preferably, in the Fc region that modify the binding affinity of the antibody to one or more FcγR. Methods for modifying antibodies with modified binding to one or more FcγR are known in the art, see, e.g., PCT Publication Nos. WO 99/58572, WO 99/51642, WO 98/23289, WO 89/07142, WO 88/07089, and U.S. Pat. Nos. 5,843,597 and 5,642,821, each of which is incorporated herein by reference in its entirety. In some embodiments, the invention encompasses antibodies that have altered affinity for a protein in the complement cascade, e.g., C1q. Preferably such modifications also have an altered Fc-mediated effector function. Modifications that affect Fc-mediated effector function are well known in the art (See U.S. Pat. No. 6,194,551, which is incorporated herein by reference in its entirety). The amino acids that can be modified in accordance with the method of the invention include, but are not limited to, Proline 329, Proline 331, and Lysine 322. Proline 329, 331 and Lysine 322 are preferably replaced with alanine, however, substitution with any other amino acid is contemplated. See International Publication No.: WO 00/42072 and U.S. Pat. No. 6,194,551 which are incorporated herein by reference in their entireties. The invention encompasses any mutation known in the art for modified effector functions, including, but not limited to, C1q binding, complement dependent cytotoxicity activity such as those disclosed in U.S. Pat. No. 6,528,624 (Idusogie et al.); U.S. Pat. No. 6,535,124 (Idusogie et al.); and U.S. Pat. No. 6,242,195(Idusogie et al.); and International Publication No. WO 99/51642; each of which is incorporated herein by reference in its entirety.

In one particular embodiment, the modification of the Fc region comprises one or more mutations in the Fc region. The one or more mutations in the Fc region may result in an antibody with an altered antibody-mediated effector function, an altered binding to other Fc receptors (e.g., Fc activation receptors), an altered ADCC activity, or an altered C1q binding activity, or an altered complement dependent cytotoxicity activity, or any combination thereof.

The invention also provides antibodies with altered oligosaccharide content. Oligosaccharides as used herein refer to carbohydrates containing two or more simple sugars and the two terms may be used interchangeably herein. Carbohydrate moieties of the instant invention will be described with reference to commonly used nomenclature in the art. For a review of carbohydrate chemistry, see, e.g., Hubbard et al., 1981 Ann. Rev. Biochem., 50: 555-583, which is incorporated herein by reference in its entirety. This nomenclature includes, for example, Man which represents mannose; GlcNAc which represents 2-N-acetylglucosamine; Gal which represents galactose; Fuc for fucose and Glc for glucose. Sialic acids are described by the shorthand notation NeuNAc for 5-N-acetylneuraminic acid, and NeuNGc for 5-glycolneuraminic In general, antibodies contain carbohydrate moeities at conserved positions in the constant region of the heavy chain, and up to 30% of human IgGs have a glycosylated Fab region. IgG has a single N-linked biantennary carbohydrate structure at Asn 297 which resides in the CH2 domain (Jefferis et al., 1998, Immunol. Rev. 163: 59-76; Wright et al., 1997, Trends Biotech 15: 26-32). Human IgG typically has a carbohydrate of the following structure; GlcNAc(Fucose)-GlcNAc-Man-(ManGlcNAc)$_2$. However variations among IgGs in carbohydrate content does occur which leads to altered function, see, e.g., Jassal et al., 2001 Bichem. Biophys. Res. Commun. 288: 243-9; Groenink et al., 1996 J. Immunol. 26: 1404-7; Boyd et al., 1995 Mol. Immunol. 32: 1311-8; Kumpel et al., 1994, Human Antibody Hybridomas, 5: 143-51.

The invention encompasses antibodies comprising one or more modifications at position 297.

In some embodiments, the antibodies of the invention are substantially free of one or more selected sugar groups, e.g., one or more sialic acid residues, one or more galactose residues, one or more fucose residues. An antibody that is substantially free of one or more selected sugar groups may be prepared using common methods known to one skilled in the art, including, for example, recombinantly producing an antibody of the invention in a host cell that is defective in the addition of the selected sugar groups(s) to the carbohydrate moiety of the antibody, such that about 90-100% of the antibody in the composition lacks the selected sugar group(s) attached to the carbohydrate moiety. Alternative methods for preparing such antibodies include, for example, culturing cells under conditions which prevent or reduce the addition of one or more selected sugar groups, or post-translational removal of one or more selected sugar groups.

In a specific embodiment, the invention encompasses a method of producing a substantially homogenous antibody preparation, wherein about 80-100% of the antibody in the composition lacks a fucose on its carbohydrate moiety on its Fc region. The antibody may be prepared for example by (a) use of an engineered host cell that is deficient in fucose metabolism such that it has a reduced ability to fucosylate proteins expressed therein; (b) culturing cells under conditions which prevent or reduce fusocylation; (c) post-translational removal of fucose, e.g., with a fucosidase enzyme; or (d) purification of the antibody so as to select for the product which is not fucosylated. Most preferably, nucleic acid encoding the desired antibody is expressed in a host cell that has a reduced ability to fucosylate the antibody expressed therein. Preferably the host cell is a dihydrofolate reductase deficient chinese hamster ovary cell (CHO), e.g., a Lec 13 CHO cell (lectin resistant CHO mutant cell line; Ribka & Stanley, 1986, Somatic Cell & Molec. Gen. 12(1): 51-62; Ripka et al., 1986 Arch. Biochem. Biophys. 249(2): 533-45), CHO-K1, DUX-B11, CHO-DP12 or CHO-DG44, which has been modified so that the antibody is not substantially fucosylated. Thus, the cell may display altered expression and/or activity for the fucoysltransferase enzyme, or another enzyme or substrate involved in adding fucose to the N-linked oligosaccharide so that the enzyme has a diminished activity and/or reduced expression level in the cell. For methods to produce antibodies with altered fucose content, see, e.g., WO 03/035835 and Shields et al., 2002, J. Biol. Chem. 277(30): 26733-40; both of which are incorporated herein by reference in their entireties.

In some embodiments, the altered carbohydrate modifications modulate one or more of the following: solubilization of the antibody, facilitation of subcellular transport and secretion of the antibody, promotion of antibody assembly, conformational integrity, and antibody-mediated effector function. In a specific embodiment the altered carbohydrate modifications enhance antibody mediated effector function relative to the antibody lacking the carbohydrate modification. Carbohydrate modifications that lead to altered antibody mediated effector function are well known in the art (for e.g., see Shields R. L. et al., 2001, *J. Biol. Chem.* 277(30): 26733-40; Davies J. et al., 2001, *Biotechnology & Bioengineering,* 74(4): 288-294). Altering carbohydrate modifications in accordance with the methods of the invention includes, for example, increasing the carbohydrate content of the antibody or decreasing the carbohydrate content of the antibody. Methods of altering carbohydrate contents are known to those skilled in the art, see, e.g., Wallick et al., 1988, *Journal of Exp. Med.* 168(3): 1099-1109; Tao et al., 1989 *Journal of Immunology,* 143(8): 2595-2601; Routledge et al., 1995, *Transplantation,* 60(8): 847-53; Elliott et al. 2003; *Nature Biotechnology,* 21: 414-21; Shields et al., 2002, *Journal of Biological Chemistry,* 277(30): 26733-40; all of which are incorporated herein by reference in their entireties.

In some embodiments, the invention encompasses antibodies comprising one or more glycosylation sites, so that one or more carbohydrate moieties are covalently attached to the antibody. In other embodiments, the invention encompasses antibodies comprising one or more glycosylation sites and one or more modifications in the Fc region, such as those disclosed supra and those known to one skilled in the art. In preferred embodiments, the one or more modifications in the Fc region enhance the affinity of the antibody for an activating FcγR, e.g., FcγRIIIA, relative to the antibody comprising the wild type Fc regions. Antibodies of the invention with one or more glycosylation sites and/or one or more modifications in the Fc region have an enhanced antibody mediated effector function, e.g., enhanced complement activity. In some embodiments, the invention further comprises antibodies comprising one or more modifications of amino acids that are directly or indirectly known to interact with a carbohydrate moiety of the antibody, including, but not limited to, amino acids at positions 241, 243, 244, 245, 245, 249, 256, 258, 260, 262, 264, 265, 296, 299, and 301. Amino acids that directly or indirectly interact with a carbohydrate moiety of an antibody are known in the art, see, e.g., Jefferis et al., 1995, *Immunology Letters* 44: 111-7, which is incorporated herein by reference in its entirety.

The invention encompasses antibodies that have been modified by introducing one or more glycosylation sites into one or more sites of the antibodies, preferably without altering the functionality of the antibody, e.g., binding activity to a flaviviral antigen. Glycosylation sites may be introduced into the variable and/or constant region of the antibodies of the invention. As used herein, "glycosylation sites" include any specific amino acid sequence in an antibody to which an oligosaccharide (i.e., carbohydrates containing two or more simple sugars linked together) will specifically and covalently attach. Oligosaccharide side chains are typically linked to the backbone of an antibody via either N- or O-linkages. N-linked glycosylation refers to the attachment of an oligosaccharide moiety to the side chain of an asparagine residue. O-linked glycosylation refers to the attachment of an oligosaccharide moiety to a hydroxyamino acid, e.g., serine, threonine. The antibodies of the invention may comprise one or more glycosylation sites, including N-linked and O-linked glycosylation sites. Any glycosylation site for N-linked or O-linked glycosylation known in the art may be used in accordance with the instant invention. An exemplary N-linked glycosylation site that is useful in accordance with the methods of the present invention, is the amino acid sequence: Asn-X-Thr/Ser, wherein X may be any amino acid and Thr/Ser indicates a threonine or a serine. Such a site or sites may be introduced into an antibody of the invention using methods well known in the art to which this invention pertains. See, for example, "*In vitro Mutagenesis,*" *Recombinant DNA: A Short Course,* J. D. Watson, et al. W.H. Freeman and Company, New York, 1983, chapter 8, pp. 106-116, which is incorporated herein by reference in its entirety. An exemplary method for introducing a glycosylation site into an antibody of the invention may comprise: modifying or mutating an amino acid sequence of the antibody so that the desired Asn-X-Thr/Ser sequence is obtained.

Methods for modifying the carbohydrate content of antibodies are well known in the art and encompassed within the invention, see, e.g., U.S. Pat. No. 6,218,149; EP 0 359 096 B1; U.S. Patent Application Publication No. U.S. 2002/0028486; WO 03/035835; U.S. Patent Application Publication No. 2003/0115614; U.S. Pat. Nos. 6,218,149; 6,472,511; all of which are incorporated herein by reference in their entireties. In other embodiments, the invention encompasses methods of modifying the carbohydrate content of an antibody of the invention by deleting one or more endogenous carbohydrate moieties of the antibody.

The invention further encompasses methods of modifying an effector function of an antibody of the invention, wherein the method comprises modifying the carbohydrate content of the antibody using the methods disclosed herein or known in the art.

Standard techniques known to those skilled in the art can be used to introduce mutations in the nucleotide sequence encoding an antibody, or fragment thereof, including, e.g., site-directed mutagenesis and PCR-mediated mutagenesis, which results in amino acid substitutions. Preferably, the derivatives include less than 15 amino acid substitutions, less than 10 amino acid substitutions, less than 5 amino acid substitutions, less than 4 amino acid substitutions, less than 3 amino acid substitutions, or less than 2 amino acid substitutions relative to the original antibody or fragment thereof. In a preferred embodiment, the derivatives have conservative amino acid substitutions made at one or more predicted non-essential amino acid residues.

The present invention also encompasses antibodies or fragments thereof comprising an amino acid sequence of a variable heavy chain and/or variable light chain that is at least 45%, at least 50%, at least 55%, at least 60%, at least 65%, at least 70%, at least 75%, at least 80%, at least 85%, at least 90%, at least 95%, or at least 99% identical to the amino acid sequence of the variable heavy chain and/or light chain of a mouse monoclonal antibody produced by clones E16, E24, or E34, having ATCC Accession Nos. PTA-6050, PTA-6051, and PTA-6052, respectively. The present invention also encompasses antibodies or fragments thereof comprising an amino acid sequence of a variable heavy chain and/or variable light chain that is at least 45%, at least 50%, at least 55%, at least 60%, at least 65%, at least 70%, at least 75%, at least 80%, at least 85%, at least 90%, at least 95%, or at least 99% identical to the amino acid sequence of the variable heavy chain and/or light chain of the mouse monoclonal antibody having SEQ ID Nos. 2, 6, 10, 4, 8, or 12.

The present invention further encompasses antibodies or fragments thereof that specifically bind one or more flaviviral antigens, preferably one or more WNV antigens, said antibodies or antibody fragments comprising an amino acid sequence of one or more CDRs that is at least 45%, at least 50%, at least 55%, at least 60%, at least 65%, at least 70%, at least 75%, at least 80%, at least 85%, at least 90%, at least 95%, or at least 99% identical to the amino acid sequence of one or more CDRs of a mouse monoclonal antibody produced by clones E16, E24, or E34, having ATCC Accession Nos. PTA-6050, PTA-6051, and PTA-6052, respectively. The determination of percent identity of two amino acid sequences can be determined by any method known to one skilled in the art, including BLAST protein searches.

The present invention also encompasses the use of antibodies or antibody fragments that specifically bind one or more flaviviral antigens, preferably one or more WNV antigens, wherein said antibodies or antibody fragments are encoded by a nucleotide sequence that hybridizes to the nucleotide sequence of a mouse monoclonal antibody produced by clones E16, E24, or E34, having ATCC Accession Nos. PTA-6050, PTA-6051, and PTA-6052, respectively, under stringent conditions. In a preferred embodiment, the invention provides antibodies or fragments thereof that specifically bind one or more flaviviral antigens, preferably one or more WNV antigens, said antibodies or antibody fragments comprising a variable light and/or variable heavy chain encoded by a nucleotide sequence that hybridizes under stringent conditions to the nucleotide sequence of the variable light and/or variable heavy chain of a mouse monoclonal antibody produced by clones E16, E24, or E34, having ATCC Accession Nos. PTA-6050, PTA-6051, and PTA-6052, respectively, under stringent conditions. In another preferred embodiment, the invention provides antibodies or fragments thereof that specifically bind one or more flaviviral antigens, preferably one or more WNV antigens, said antibodies or antibody fragments comprising one or more CDRs encoded by a nucleotide sequence that hybridizes under stringent conditions to the nucleotide sequence of one or more CDRs of a mouse monoclonal antibody produced by clones E16, E24, or E34, having ATCC Accession Nos. PTA-6050, PTA-6051, and PTA-6052, respectively. Stringent hybridization conditions include, but are not limited to, hybridization to filter-bound DNA in 6X sodium chloride/sodium citrate (SSC) at about 45° C. followed by one or more washes in 0.2X SSC/0.1% SDS at about 50-65° C., highly stringent conditions such as hybridization to filter-bound DNA in 6X SSC at about 45° C. followed by one or more washes in 0.1X SSC/0.2% SDS at about 60° C., or any other stringent hybridization conditions known to those skilled in the art (see, for example, Ausubel, F. M. et al., eds. 1989 *Current Protocols in Molecular Biology*, vol. 1, Green Publishing Associates, Inc. and John Wiley and Sons, Inc., NY at pages 6.3.1 to 6.3.6 and 2.10.3), incorporated herein by reference.

5.1.1 Antibody Conjugates

The present invention encompasses antibodies or fragments thereof recombinantly fused or chemically conjugated (including both covalently and non-covalently conjugations) to a heterologous polypeptide (or portion thereof, preferably at least 10, at least 20, at least 30, at least 40, at least 50, at least 60, at least 70, at least 80, at least 90 or at least 100 amino acids of the polypeptide) to generate fusion proteins. The fusion does not necessarily need to be direct, but may occur through linker sequences. For example, antibodies may be used to target heterologous polypeptides to particular cell types (e.g., respiratory epithelial cells), either in vitro or in vivo, by fusing or conjugating the antibodies to antibodies specific for particular cell surface receptors. Antibodies fused or conjugated to heterologous polypeptides may also be used in in vitro immunoassays and purification methods using methods known in the art. See e.g., PCT Publication No. WO 93/21232; EP 439,095; Naramura et al., Immunol. Lett. 39:91-99 (1994); U.S. Pat. No. 5,474,981; Gillies et al., *Proc Natl Acad Sci USA* 89:1428-1432 (1992); and Fell et al., J. Immunol. 146:2446-2452(1991), which are incorporated by reference in their entireties.

In one embodiment, a fusion protein of the invention comprises an antibody comprising the amino acid sequence listed in SEQ ID Nos. 2, 6, 10, 4, 8, 12, or 13-43 and a heterologous polypeptide. In another embodiment, a fusion protein of the invention comprises an antigen-binding fragment of an antibody having the amino acid sequence listed in SEQ ID Nos. 2, 6, 10, 4, 8, 12 and a heterologous polypeptide. In another embodiment, a fusion protein of the invention comprises one or more VH domains having the amino acid sequence of any one of the VH domains listed in SEQ ID NOs. 4, 8 or 12 or one or more VL domains having the amino acid sequence of any one of the VL domains listed in SEQ ID NOs. 2, 6, or 10 and a heterologous polypeptide.

In another embodiment, a fusion protein of the present invention comprises one or more VH CDRs having the amino acid sequence of any one of the VH CDRs listed in SEQ ID NOs. 16-17, 20-22, or 26-28 and a heterologous polypeptide. In another embodiment, a fusion protein comprises one or more VL CDRs having the amino acid sequence of any one of the VL CDRs listed in SEQ ID NOs. 33, 37, or 40-41 and a heterologous polypeptide. In another embodiment, a fusion protein of the invention comprises at least one VH domain and at least one VL domain listed in SEQ ID NOs. 16-17, 20-22, 26-28, 33, 37, or 40-41 and a heterologous polypeptide. In yet another embodiment, a fusion protein of the invention comprises at least one VH CDR and at least one VL CDR domain listed in SEQ ID NOs. 16-17, 20-22, 26-28, 33, 37, or 40-41 and a heterologous polypeptide.

The present invention further includes compositions comprising heterologous polypeptides fused or conjugated to antibody fragments. For example, the heterologous polypeptides may be fused or conjugated to a Fab fragment, Fd fragment, Fv fragment, F(ab)$_2$ fragment, or portion thereof. Methods for fusing or conjugating polypeptides to antibody portions are known in the art. See, e.g., U.S. Pat. Nos. 5,336, 603, 5,622,929, 5,359,046, 5,349,053, 5,447,851, and 5,112, 946; EP 307,434; EP 367,166; PCT publication Nos. WO 96/04388 and WO 91/06570; Ashkenazi et al., Proc. Natl. Acad. Sci. USA 88: 10535-10539 (1991); Zheng et al., J. Immunol. 154:5590-5600 (1995); and Vil et al., Proc. Natl. Acad. Sci. USA 89:11337-11341(1992) (said references incorporated by reference in their entireties).

Additional fusion proteins of the invention may be generated through the techniques of gene-shuffling, motif-shuffling, exon-shuffling, and/or codon-shuffling (collectively referred to as "DNA shuffling"). DNA shuffling may be employed to alter the activities of antibodies of the invention or fragments thereof (e.g., antibodies or fragments thereof with higher affinities and lower dissociation rates). See, generally, U.S. Pat. Nos. 5,605,793; 5,811,238; 5,830,721; 5,834, 252; and 5,837,458, and Patten et al., Curr. Opinion Biotechnol. 8:724-33 (1997); Harayama, Trends Biotechnol. 16(2): 76-82 (1998); Hansson, et al., J. Mol. Biol. 287:265-76 (1999); and Lorenzo and Blasco, Biotechniques 24(2):308-13 (1998) (each of these patents and publications are hereby incorporated by reference in its entirety). In one embodiment, antibodies or fragments thereof, or the encoded antibodies or fragments thereof, may be altered by being subjected to random mutagenesis by error-prone PCR, random nucleotide insertion or other methods prior to recombination. In another embodiment, one or more portions of a polynucleotide encoding an antibody or antibody fragment, which portions immunospecifically bind to a flaviviral antigen may be recombined with one or more components, motifs, sections, parts, domains, fragments, etc. of one or more heterologous molecules.

Moreover, the antibodies of the present invention or fragments thereof can be fused to marker sequences, such as a peptide to facilitate purification. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., 1989, Proc. Natl. Acad. Sci. USA 86:821-824, for instance, hexa-histidine provides for convenient purification of the fusion protein. Other peptide tags useful for purification include, but are not limited to, the hemagglutinin "HA" tag, which corresponds to an epitope derived from the influenza hemagglutinin protein (Wilson et al., 1984, Cell 37:767) and the "flag" tag.

The present invention further encompasses antibodies or fragments thereof conjugated to a diagnostic or therapeutic agent. The antibodies can be used diagnostically to, for example, monitor the development or progression of a flaviviral infection as part of a clinical testing procedure to, e.g., determine the efficacy of a given treatment regimen. Detection can be facilitated by coupling the antibody or fragment thereof to a detectable substance. Examples of detectable substances include various enzymes, prosthetic groups, fluorescent materials, luminescent materials, bioluminescent materials, radioactive materials, positron emitting metals, and nonradioactive paramagnetic metal ions. The detectable substance may be coupled or conjugated either directly to the antibody (or fragment thereof) or indirectly, through an intermediate (such as, for example, a linker known in the art) using techniques known in the art. See, for example, U.S. Pat. No. 4,741,900 for metal ions which can be conjugated to antibodies for use as diagnostics according to the present invention. Examples of detectable substances include various enzymes, prosthetic groups, fluorescent materials, luminescent materials, bioluminescent materials, radioactive materials, positron emitting metals, and nonradioactive paramagnetic metal ions. The detectable substance may be coupled or conjugated either directly to the antibody or indirectly, through an intermediate (such as, for example, a linker known in the art) using techniques known in the art. See, for example, U.S. Pat. No. 4,741,900 for metal ions which can be conjugated to antibodies for use as diagnostics according to the present invention. Such diagnosis and detection can be accomplished by coupling the antibody to detectable substances including, but not limited to, various enzymes, enzymes including, but not limited to, horseradish peroxidase, alkaline phosphatase, beta-galactosidase, or acetylcholinesterase; prosthetic group complexes such as, but not limited to, streptavidin/biotin and avidin/biotin; fluorescent materials such as, but not limited to, umbelliferone, fluorescein, fluorescein isothiocyanate, rhodamine, dichlorotriazinylamine fluorescein, dansyl chloride or phycoerythrin; luminescent material such as, but not limited to, luminol; bioluminescent materials such as, but not limited to, luciferase, luciferin, and aequorin; radioactive material such as, but not limited to, bismuth ($^{213}$Bi), carbon ($^{14}$C), chromium ($^{51}$Cr), cobalt ($^{57}$Co), fluorine ($^{18}$F), gadolinium ($^{153}$Gd, $^{159}$Gd), gallium ($^{68}$Ga, $^{67}$Ga), germanium ($^{68}$Ge), holmium ($^{166}$Ho), indium ($^{115}$In, $^{113}$In, $^{112}$In, $^{111}$In), iodine ($^{131}$I, $^{125}$I, $^{123}$I, $^{121}$I), lanthanium ($^{140}$La), lutetium ($^{177}$Lu), manganese ($^{54}$Mn), molybdenum ($^{99}$Mo), palladium ($^{103}$Pd), phosphorous ($^{32}$P), praseodymium ($^{142}$Pr), promethium ($^{149}$Pm), rhenium ($^{186}$Re, $^{188}$Re), rhodium ($^{105}$Rh), ruthemium ($^{97}$Ru), samarium ($^{153}$Sm), scandium ($^{47}$Sc), selenium ($^{75}$Se), strontium ($^{85}$Sr), sulfur ($^{35}$S), technetium ($^{99}$Tc), thallium ($^{201}$Ti), tin ($^{113}$Sn, $^{117}$Sn), tritium ($^{3}$H), xenon ($^{133}$Xe), ytterbium ($^{169}$Yb, $^{175}$Yb), yttrium ($^{90}$Y), zinc ($^{65}$Zn); positron emitting metals using various positron emission tomographies, and nonradioactive paramagnetic metal ions.

An antibody or fragment thereof may be conjugated to a therapeutic moiety such as a cytotoxin, e.g., a cytostatic or cytocidal agent, a therapeutic agent or a radioactive metal ion, e.g., alpha-emitters. A cytotoxin or cytotoxic agent includes any agent that is detrimental to cells. Examples include paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cisdichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

Further, an antibody or fragment thereof may be conjugated to a therapeutic agent or drug moiety that modifies a given biological response. Therapeutic agents or drug moieties are not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, α-interferon, β-interferon, nerve growth factor, platelet derived growth factor, tissue plasminogen activator, an apoptotic agent, e.g., TNF-α, TNF-β, AIM I (see, International Publication No. WO 97/33899), AIM II (see, International Publication No. WO 97/34911), Fas Ligand (Takahashi et al., 1994, J. Immunol., 6:1567-1574), and VEGI (see, International Publication No. WO 99/23105), a thrombotic agent or an anti-angiogenic agent, e.g., angiostatin or endostatin; or, a biological response modifier such as, for example, a lymphokine (e.g., interleukin-1 ("IL-1"), interleukin-2 ("IL-2"), interleukin-6 ("IL-6"), granulocyte macrophage colony stimulating factor ("GM-CSF"), and granulocyte colony stimulating factor ("G-CSF")), or a growth factor (e.g., growth hormone ("GH")).

Techniques for conjugating such therapeutic moieties to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., 1982, Immunol. Rev. 62:119-58.

An antibody or fragment thereof, with or without a therapeutic moiety conjugated to it, administered alone or in combination with cytotoxic factor(s) and/or cytokine(s) can be used as a therapeutic. Alternatively, an antibody can be conjugated to a second antibody to form an antibody heteroconjugate as described by Segal in U.S. Pat. No. 4,676,980, which is incorporated herein by reference in its entirety.

Antibodies may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

5.2 Immunizing, Screening, Identification of Antibodies and Characterization

The present invention encompasses methods for generating antibodies preferably monoclonal antibodies against one or more flaviviral antigens, e.g., WNV antigens. Individual antibodies against specific determinants on the E and NS1 proteins inhibit WNV infection by multiple mechanisms. Some antibodies directly disrupt a critical step in viral lifecycle such as receptor attachment and entry whereas others inhibit indirectly by triggering immune-mediated clearance via complement-mediated opsonization and lysis of infected cells or antibody-dependent internalization by phagocytic cells. The present invention encompasses immunization of mice with WNV proteins, such as purified E and NS1 proteins, and whole virus to generate a panel of protective monoclonal antibodies with different binding specificities, avidities, isotypes, and effector functions. Functional and structural characterization of monoclonal antibodies against WNV will inform therapeutic algorithms as disclosed herein that utilize combinations of mAbs that recognize discrete structural epitopes and have distinct means for protecting against WNV infection.

The present inventors have discovered that treatment with human γ-globulin may be an effective prophylaxis and therapy against WNV infection, however, specialized testing would be required to distinguish protective from non-protective commercial batches, and a large outbreak of WNV might rapidly exhaust the supply of immune γ-globulin in a region. In addition, there may be significant lot-to-lot variability of the product due to heterogeneity of its source. Two other potential weaknesses of pooled human γ-globulin are the risk of untoward infectious agents (especially non-enveloped viruses or prions that are recalcitrant to current inactivation schemes) and the possibility of administering non-WNV antibodies that have autoreactivity or pathogenic effect. To create a more permanent, efficacious, and safe source of antibodies, the present invention provides a panel of monoclonal antibodies against the E and NS1 proteins of WNV with inhibitory activity. Although not intending to be bound by a particular mechanism of action, E and NS1 are particularly useful because mAbs against these proteins inhibit infection of related flaviviruses.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., *Antibodies: A Laboratory Manual*, (Cold Spring Harbor Laboratory Press, 2nd ed. 1988); Hammerling, et al., in: *Monoclonal Antibodies and T-Cell Hybridomas*, pp. 563-681 (Elsevier, N.Y., 1981) (both of which are incorporated by reference in their entireties). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Methods for producing and screening for specific antibodies using hybridoma technology are routine and well known in the art. In a non-limiting example, mice can be immunized with an antigen of interest or a cell expressing such an antigen. Once an immune response is detected, e.g., antibodies specific for the antigen are detected in the mouse serum, the mouse spleen is harvested and splenocytes isolated. The splenocytes are then fused by well known techniques to any suitable myeloma cells. Hybridomas are selected and cloned by limiting dilution. The hybridoma clones are then assayed by methods known in the art for cells that secrete antibodies capable of binding the antigen. Ascites fluid, which generally contains high levels of antibodies, can be generated by inoculating mice intraperitoneally with positive hybridoma clones.

The invention encompasses production of monoclonal antibodies against WNV after immunization with purified WNV proteins (E and NS1) and/or intact virus. The E protein is the virion-associated protein responsible for cell attachment and elicits the majority of neutralizing and non-neutralizing antibodies in vivo. Mice will also be immunized with NS1, a protein that is secreted from infected cells but is not present in the virion. Despite its absence from the virion, mAbs that recognize YF and DEN virus NS1 protect mice against lethal virus challenge (Henchal et al., 1988, J Gen Virol 69(Pt 8):2101-7; Schlesinger et al., 1986, J Virol 60:1153-5). Although the nature of this protection in incompletely understood, because soluble NS1 associates with the cell surface after secretion, complement-mediated cytolysis of infected cells has been proposed as the basis for protection by mAbs against NS1 (Falgout et al., 1990, J Virol 64:4356-63; Putnak et al., 1990, J Gen Virol 71(Pt 8): 1697-702; Schlesinger et al., 1990, J Gen Virol 71(Pt 3):593-9). Alternatively, mAbs to NS1 may directly block a critical immunomodulatory function (Diamond, 2003, Immunology and Cell Biology 81:196-206). NS1 is present in serum of patients infected with flaviviruses at extremely high concentrations (e.g.,1 to 50 μg/ml) (Alcon et al., 2002, J Clin Microbiol40: 376-81; Young et al., 2000, J Clin Microbiol 38:1053-7) and speculated to have a direct, yet unknown role in pathogenesis (Libraty et al., 2002, J Infect Dis 186:1165-8). By generating mAbs against both NS1 and E proteins, the invention provides a panel of reagents with inhibitory activity against WNV infection through independent mechanisms. Although not intending to be bound by a particular mechanism of action, because immunization with purified proteins could limit the antibody repertoire, resulting in the generation of fewer protective antibodies, mAbs will also be generated after immunizing with the intact virus. To insure a diversity of epitopes, the invention encompasses generation of at least 100 different mAbs against either protein.

In one specific embodiment, the invention encompasses the production of novel monoclonal antibodies with specificities for one or more WNV antigens. In particular, the invention provides a method for producing monoclonal antibodies that specifically bind one or more WNV antigens, said method comprising: (a) immunizing one or more BALB/c mice with purified WNV proteins, e.g., NS1, E protein, or an immunogenic fragment thereof, using a carbohydrate and lipid based adjuvant; (b) measuring the polyclonal antibody response using a solid phase ELISA based assay; (c) producing hybridoma cells lines from spleen cells of said one or more mice; (d) screening said hybridoma cell lines for one or more hybridoma cell lines that produce antibodies that specifically bind the particular WNV protein; (e) selecting candidate immune mice; (f) priming a single mouse with a high-titer polyclonal (e.g., 1/10,000) response intravenously with purified E or NS1 proteins (g) harvesting splenocytes and fusing then to the non-secreting P3X63Ag8.6.5.3 myeloma (or other cells such as SP2/0-Ag14, Sp2/0 and P3 myelomas) according to standard protocols (Harlow et al., 1988. Antibodies, A laboratory manual. Cold Spring Harbor Laboratory, Cold Spring Harbor). The invention encompasses any antibody produced by said method. In one embodiment of the invention, said mice are immunized with purified WNV antigens which has been mixed with any adjuvant known in the art to enhance immune response. Adjuvants that can be used in the methods of the invention include, but are not limited to, protein adjuvants; bacterial adjuvants, e.g., whole bacteria (BCG, *Corynebacterium parvum, Salmonella minnesota*) and bacterial components including cell wall skeleton, trehalose dimycolate, monophosphoryl lipid A, methanol extractable residue (MBR) of tubercle bacillus, complete or incomplete Freund's adjuvant; viral adjuvants; chemical adjuvants, e.g., aluminum hydroxide, iodoacetate and cholesteryl hemisuccinateor; naked DNA adjuvants. Other adjuvants that can be used in the methods of the invention include, Cholera toxin, paropox proteins, MF-59 (Chiron Corporation; See also Bieg et al., 1999, *Autoimmunity*, 31(1):15-24, which is incorporated herein by reference), MPL® (Corixa Corporation; See also Lodmell D. I. et al., 2000 *Vaccine*, 18: 1059-1066; Ulrich et al., 2000, *Methods in Molecular Medicine*, 273-282; Johnson et al., 1999, *Journal of Medicinal Chemistry*, 42: 4640-4649; Baldridge et al., 1999 *Methods*, 19: 103-107, all of which are incorporated herein by reference in their entireties), RC-529 adjuvant (Corixa Corporation; the lead compound from Corixa's aminoalkyl glucosaminide 4-phosphate (AGP) chemical library, see also www.corixa.com), and DETOX™ adjuvant (Corixa Corporation; DETOX™ adjuvant includes MPL® adjuvant (monophosphoryl lipid A) and mycobacterial cell wall skeleton; See also Eton et al., 1998, *Clin. Cancer Res*, 4(3):619-27; and Gubta et al., 1995, *Vaccine*, 13(14):1263-76, both of which are incorporated herein by reference in their entireties).

The invention encompasses methods for generation of MAbs against purified E and NS1 proteins. The invention encompasses use of glycosylated E and NS1 proteins from WNV which have been expressed recombinantly in insect cells using, for example, a baculovirus expression system such as those disclosed herein and previously described methods for related flaviviruses (Delenda et al., 1994, J Gen Virol 75:1569-78; Despres et al., 1991, J Gen Virol 72(Pt 11):2811-6). In an exemplary method, the E and NS1 proteins of WNV (New York 1999 strain) are amplified with a high-fidelity Taq polymerase from an infectious cDNA WNV clone. For E protein, the N-terminal 430 amino acids are utilized (nucleotides 967-2256) and the C-terminal 70 amino acids that encode the membrane-associated domains are deleted to facilitate secretion (Delenda et al., 1994, Arch Virol 139:197-207; Delenda et al., 1994, J Gen Virol 75:1569-78). For NS1, the full-length gene (nucleotides 2470-3525) is used. Both genes are inserted downstream of the polyhedrin promoter and their endogenous signal sequences (E: last 15 amino acids of prM, NS1: last 22 amino acids of E) and upstream of a C-terminal histidine repeat to facilitate expression in insect cells, secretion into the extracellular medium, and purification. Proteins are purified by Nickel affinity and size-exclusion chromatography, and analyzed by SDS-PAGE and Western blot with mAbs against E or NS1. Purified recombinant WNV E or NS1 protein (25 µg) will be complexed with adjuvant (RIBI Immunochemical, Hamilton, Mont.), and inoculated intraperitoneally into BALB/c mice. At 3 weeks after inoculation, animals will be boosted. Three weeks later, a serum sample will be obtained and tested for immunoreactivity against solid-phase purified E or NS1 protein. Mice with the highest titers will be boosted intravenously with a lower dose of E or NS1 and 3 days later, splenocytes will be harvested and fused to P3X63Ag8.653 myeloma cells to generate hybridomas according to published procedures (Diamond et al., 1993, J Cell Biol 120:1031-43; Springer et al., 1979, Eur J Immunol 9:301-306).

The invention encompasses methods for the generation of MAbs against intact virus to expand the repertoire and generate protective mAbs against additional epitopes on the E protein. Although not intending to be bound by a particular mechanism of action, immunization with intact virus will generate mAbs that recognize the membrane proximal stem-loop region of the E protein that block viral entry or fusion. This region is deleted from the recombinant E protein. Moreover, the intact virus may generate a distinct panel of anti-E mAbs that are protective. In an exemplary method, adult BALB/c mice will be infected with live WNV (~$10^4$ PFU); these animals will be boosted with intact virus three-weeks later; mice with high-titer anti-WNV responses (e.g., >1/10,000) will be boosted intravenously with UV-inactivated virus and utilized for fusion and mAb generation. Additionally, a hyper-immunization protocol will also be utilized: mice that resist multiple challenges may have qualitative differences in their antibody response that could contribute to protection.

Antibody fragments which recognize specific epitopes may be generated by known techniques. For example, Fab and F(ab')$_2$ fragments may be produced by proteolytic cleavage of immunoglobulin molecules, using enzymes such as papain (to produce Fab fragments) or pepsin (to produce F(ab')$_2$ fragments). F(ab')$_2$ fragments contain the complete light chain, and the variable region, the CH1 region and the hinge region of the heavy chain.

For example, antibodies can also be generated using various phage display methods known in the art. In phage display methods, functional antibody domains are displayed on the surface of phage particles which carry the polynucleotide sequences encoding them. In a particular embodiment, such phage can be utilized to display antigen binding domains, such as Fab and Fv or disulfide-bond stabilized Fv, expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage, including fd and M13. The antigen binding domains are expressed as a recombinantly fused protein to either the phage gene III or gene VIII protein. Examples of phage display methods that can be used to make the immunoglobulins, or fragments thereof, of the present invention include those disclosed in Brinkman et al., *J. Immunol. Methods*, 182:41-50, 1995; Ames et al., *J. Immunol. Methods*, 184:177-186, 1995; Kettleborough et al., *Eur. J. Immunol.*, 24:952-958, 1994; Persic et al., *Gene*, 187:9-18, 1997; Burton et al., *Advances in Immunology*, 57:191-280, 1994; PCT International Application No. PCT/GB91/01134; PCT International Publication Nos. WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

As described in the above references, after phage selection, the antibody coding regions from the phage can be isolated and used to generate whole antibodies, including human antibodies, or any other desired fragments, and expressed in any desired host, including mammalian cells, insect cells, plant cells, yeast, and bacteria, e.g., as described in detail below. For example, techniques to recombinantly produce Fab, Fab' and F(ab')$_2$ fragments can also be employed using methods known in the art such as those disclosed in PCT International Publication No. WO 92/22324; Mullinax et al., *BioTechniques*, 12(6):864-869, 1992; and Sawai et al., *AJRI*, 34:26-34, 1995; and Better et al., *Science*, 240:1041-1043, 1988 (each of which is incorporated by reference in its entirety). Examples of techniques which can be used to produce single-chain Fvs and antibodies include those described in U.S. Pat. Nos. 4,946,778 and 5,258,498; Huston et al., *Methods in Enzymology*, 203:46-88, 1991; Shu et al., *Proc Natl Acad Sci USA*, 90:7995-7999, 1993; and Skerra et al., *Science*, 240: 1038-1040, 1988.

Phage display technology can be used to increase the affinity of an antibody of the invention for its cognate antigen, e.g., flaviviral antigen. This technique would be useful in obtaining high affinity antibodies that could be used in the combinatorial methods of the invention. The technology, referred to as affinity maturation, employs mutagenesis or CDR walking and re-selection using a flaviviral antigen or an antigenic fragment thereof to identify antibodies that bind with higher affinity to the antigen when compared with the initial or parental antibody (See, e.g., Glaser et al., 1992, *J. Immunology* 149:3903). Mutagenizing entire codons rather than single nucleotides results in a semi-randomized repertoire of amino acid mutations. Libraries can be constructed consisting of a pool of variant clones each of which differs by a single amino acid alteration in a single CDR and which contain variants representing each possible amino acid substitution for each CDR residue. Mutants with increased binding affinity for the antigen can be screened by contacting the immobilized mutants with labeled antigen. Any screening method known in the art can be used to identify mutant antibodies with increased avidity to the antigen (e.g., ELISA) (See Wu et al., 1998, *Proc Natl. Acad Sci. USA* 95:6037; Yelton et al., 1995, *J. Immunology* 155:1994). CDR walking which randomizes the light chain is also possible (See Schier et al., 1996, *J. Mol. Bio.* 263:551).

Antibodies of the invention may be further characterized by epitope mapping, so that antibodies may be selected that have the greatest specificity for a WNV antigen, e.g., E protein, or NS1 protein. Epitope mapping methods of antibodies are well known in the art and encompassed within the methods of the invention. In certain embodiments fusion proteins comprising one or more regions of an WNV antigen may be used in mapping the epitope of an antibody of the invention.

To define distinct structural epitopes that are present on WNV protein, e.g., E proteins of WNV, the invention encompasses competition-binding studies using an ELISA and/or surface plasmon resonance based assays such as those disclosed in Lanciotti et al., 2000, J Clin Microbiol 38:4066-71; and Modis et al., 2003, Proc Natl Acad Sci USA 100:6986-91.

ELISA based assays are well known in the art and encompassed within the instant invention. Such assays are routine and well known in the art (see, e.g., Ausubel et al., eds, 1994, Current Protocols in Molecular Biology, Vol. 1, John Wiley & Sons, Inc., New York, which is incorporated by reference herein in its entirety). In an exemplary assay, in the ELISA format, small quantities of individual purified monoclonal antibodies will be labeled with biotin. Competing unlabeled monoclonal antibodies will be bound to recombinant E proteins in microtiter plates. Subsequently, biotinylated monoclonal antibodies will be added, and after washing, detected with peroxidase-conjugated streptavidin. Competition for an individual structural epitope will be defined as a >40% decrease in the mean OD$_{450}$ across multiple experiments after comparing binding of biotinylated monoclonal antibodies plus competing monoclonal antibodies with binding of biotinylated monoclonal antibodies alone.

Surface plasmon resonance based assays are known in the art and encompassed within the instant invention. For a review of SPR-based technology, see Mullet et al., 2000, *Methods* 22: 77-91; Dong et al., 2002, *Review in Mol. Biotech.*, 82: 303-23; Fivash et al., 1998, *Current Opinion in Biotechnology* 9: 97-101; Rich et al., 2000, *Current Opinion in Biotechnology* 11: 54-61; all of which are incorporated herein by reference in their entireties. Additionally, any of the SPR instruments and SPR based methods for measuring protein-protein interactions described in U.S. Pat. Nos. 6,373, 577; 6,289,286; 5,322,798; 5,341,215; 6,268,125 are contemplated in the methods of the invention, all of which are incorporated herein by reference in their entireties. In an exemplary assay, in the BIAcore format, monoclonal antibodies are reacted sequentially with a surface onto which the antigen WNV E protein has been coupled, leading to an increase in the SPR signal. After saturation of all of the available sites by a first antibody, the addition of a competing monoclonal antibody will not increase the SPR signal appreciably. A non-competing monoclonal antibody, on the other hand, will increase the overall signal independent of the first binding level achieved. Since the maximum signal obtained with different mAbs may vary, each assay will be repeated in the reverse order of monoclonal antibody addition. Preferably the invention encompasses characterizing the antibodies of the invention using both an ELISA and a BIAcore based assay to define a functional epitope map using the panel of mAbs obtained.

The invention encompasses epitope mapping using one or more of the following three strategies: (1) directed evolution of an WNV antigen, e.g., E protein on the surface of yeast; (2) synthetic peptides; and (3) WNV protein chimeras. An exemplary yeast display system for epitope mapping of a WNV specific antibody of the invention may comprise the following: expressing the entire ectodomain of WNV E protein or domain III alone on the surface of yeast; using the yeast displaying these proteins to identify monoclonal antibodies that are domain III-specific; and using a combinatorial library of E variants generated by error-prone PCR to map antibody epitopes at the amino acid level. The entire ectodomain or domain III of the WNV E protein will be mutagenized by error-prone PCR; importantly, an N-terminal Xpress™ peptide tag will be added to track E protein surface expression independently. Mutagenesis will be achieved by changing the Mg$^{2+}$:Mn$^{2+}$ ratio (to ~6.6:1) in the initial PCR reaction to obtain a nucleotide error rate of approximately 0.5% using a method such as that disclosed in Chothia et al. (1989, Nature 342:877-83), or on average 1 amino acid change per variant. These variants will be cloned into a yeast expression vector, e.g., pYD1 with the goal of generating ~10$^5$ independent transformants. Libraries will be constructed by cloning or homologous recombination of PCR-mutagenized segments with the parental vector in yeast cells, a technique that gives rise to libraries of high diversity (See, e.g., Chothia et al., 1989, Nature 342:877-83; Holgate et al., 2001, Curr Med Res Opin 17:233-40). To isolate variants that have lost a particular mAb epitope, an initial depletion step will be performed with protein G-coated magnetic beads using a method disclosed in Pogodina et al. (1983, Arch Virol 75:71-86). The remaining yeast cells will be sorted by two-color flow cytometry using a directly conjugated mAb to the Xpress$^{HI}$ tag and the individual antibody to the E protein that is being mapped. Yeast cells that are Express$^{HI}$ and anti-E low or null will be collected, cultivated and subjected to repeated rounds of sorting and then immunostained with other anti-E mAbs to confirm that large-scale structural changes have not occurred. Finally, the E protein variants from individual clones will be sequenced; plasmids can be recovered from yeast by *E. coli* rescue using a commercially available kit (e.g., Zymo Research, Orange, Calif.) and used to prepare DNA for sequencing. Under optimal screening conditions, flow cytometry sorting should allow fine discrimination between mutants with antibody specificity changes. In some instances, a single amino acid change may not be sufficient to abrogate mAb recognition. For mAbs that show decreased but detectable expression after the initial screen, serial mutagenesis will be undertaken.

In other embodiments, the invention encompasses methods whereby mAb binding sites may be mapped by analysis of binding to synthetic peptides or recombinant E protein fragments. Initially, about 30 overlapping peptides (e.g., 15-20 amino acids in length) will be synthesized; these peptides will be designed based on previous mapping studies with the related DEN (see, e.g., Kulkarni et al., 1991, Viral Immunol 4:73-82; Kurane et al., 1984, J Virol 52:223-30) and Murray Valley encephalitis viruses (see, e.g., Kurane et al., 1992, Semin Immunol 4:121-7) and the three-dimensional crystal structure of DEN (see, e.g., Kacani et al., 2001, Mol Immunol38:241-7), tick-borne encephalitis (see, e.g., Kramer et al., 2001, Ann NY Acad Sci 951:84-93), and WNV E proteins. mAbs will be mapped on the basis of their ability to bind peptides adsorbed to microtiter plates using a standard ELISA assay.

Because some of the mAbs may bind non-linear epitopes or epitopes not correctly displayed by the yeast cells, the invention further encompasses an alternate strategy using recombinantly derived fragments of the E protein. The extracellular domain of DEN and WNV E protein will each be expressed and secreted in mammalian cells (HEK-293) using a mammalian expression vector (e.g., pCDNA3.1). E protein chimera will be generated such that sub-domains of the WNV E protein are replaced by the equivalent regions of DEN (or vice versa). Finally, WNV and DEN E proteins chimera will be made in which specific segments or amino acid residues of domain III are substituted. Binding of the antibodies to this each of these proteins will be determined by ELISA and used for fine structural mapping.

The antibodies of the invention may be characterized for specific binding to a flaviral antigen using any immunological or biochemical based method known in the art for characterizing including quantitating the interaction of the antibody to a flaviral antigen. Specific binding of an antibody of the invention to a flaviral antigen may be determined, for example, using immunological or biochemical based methods including, but not limited to, an ELISA assay, surface plasmon resonance assays, immunoprecipitation assay, affinity chromatography, and equilibrium dialysis. Immunoassays which can be used to analyze immunospecific binding and cross-reactivity of the antibodies of the invention include, but are not limited to, competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see, e.g., Ausubel et al., eds, 1994, Current Protocols in Molecular Biology, Vol. 1, John Wiley & Sons, Inc., New York, which is incorporated by reference herein in its entirety).

Antibodies of the invention may also be assayed using any surface plasmon resonance based assays known in the art for characterizing the kinetic parameters of the interaction of the antibody with a flavivirus. Any SPR instrument commercially available including, but not limited to, BIAcore Instruments, available from Biacore AB (Uppsala, Sweden); IAsys instruments available from Affinity Sensors (Franklin, Mass.); IBIS system available from Windsor Scientific Limited (Berks, UK), SPR-CELLIA systems available from Nippon Laser and Electronics Lab (Hokkaido, Japan), and SPR Detector Spreeta available from Texas Instruments (Dallas, Tex.) can be used in the instant invention. For a review of SPR-based technology see Mullet et al., 2000, *Methods* 22: 77-91; Dong et al., 2002, *Review in Mol. Biotech.*, 82: 303-23; Fivash et al., 1998, *Current Opinion in Biotechnology* 9: 97-101; Rich et al., 2000, *Current Opinion in Biotechnology* 11: 54-61; all of which are incorporated herein by reference in their entirety. Additionally, any of the SPR instruments and SPR based methods for measuring protein-protein interactions described in U.S. Pat. Nos. 6,373,577; 6,289,286; 5,322,798; 5,341,215; 6,268,125 are contemplated in the methods of the invention, all of which are incorporated herein by reference in their entireties.

The invention encompasses characterization of the antibodies produced by the methods of the invention using certain characterization assays for identifying the function of the antibodies of the invention, particularly the activity to inhibit a flaviviral infection using in vitro and in vivo based assays. The invention encompasses cell based and cell free assays.

The invention encompasses characterizing the antibodies of the invention using qualitative based screens, e.g., an ELISA assay, preferably as a primary screen for characterizing the antibodies of the invention. The invention provides an ELISA that detects antibodies against adsorbed purified E or NS1 protein as the primary screen. An exemplary ELISA based assay for characterizing the antibodies of the invention comprises the following: when intact virus is used as an immunogen, lysates from WNV-infected BHK21 cells will be substituted to insure that additional E protein epitopes are present during the screen; positive clones will be confirmed for immunoreactivity with WNV-infected cells by flow cytometry. To obtain mAbs that recognize conserved WNV epitopes, immunoreactivity with other (lineage I and II) WNV strains will be confirmed. To avoid possible complications associated with flavivirus cross-reactive antibodies (e.g., ADE associated with heterologous flavivirus infection), candidate mAbs that positively react with WNV proteins will be tested for binding to Vero cells infected with DEN, yellow fever, or St. Louis encephalitis viruses; only WNV-specific mAbs will be used for further studies. Because different mAb isotypes may display different effector functions in vivo, isotypes will be determined using a commercially available ELISA kit.

In other embodiments, the invention encompasses quantitative functional screens to characterize the potential mechanisms of mAb-mediated inhibition of WNV infection. A scoring system will be generated from each assay to identify mAbs with the greatest inhibitory activity. The invention encompasses characterization of the anitbodies of the invention using virus neutralization assays using methods known in the art and encompassed herein. In an exemplary assay, the ability to neutralize WNV infection in cell culture will be determined using a plaque reduction neutralization assay (PRNT) with BHK21 cells. Although not intending to be bound by a particular mechanism of action, since NS1 is not present in the virion, mAbs against NS1 should not directly inhibit virus attachment or internalization. For the anti-E mAbs, a neutralizing index will be generated. Using a standard concentration (e.g., 100 µg/ml) of purified antibody, a point scale will be assigned from the $PRNT_{50}$ value: $<1/10=0$ points, $1/10-1/100=1$ point, $>1/100=2$ points. The invention encompasses characterization of the anitbodies of the invention using complement-mediated cytolysis assays using methods known in the art and encompassed herein. The ability of antibodies to trigger complement-mediated lysis of WNV-infected cells will be assessed by a standard target cell lysis assay (see, e.g., Stanley et al., 1986, J Virol 58:107-115). BHK21 cells will be infected with WNV for 24 hours and labeled with $^{51}Cr$. Washed cells will be incubated with purified mAbs and guinea pig complement (1 h at 37° C.). Supernatants will be harvested and antibody-dependent complement-mediated cell lysis will be measured by scintillation counting. A point scale will be assigned based on the percentage of cells that are specifically lysed by mAb and complement: $<10\%=0$ points, $10-40\%=1$ point, $>40\%=2$ points. In yet other embodiments, the invention encompasses characterization of the anitbodies of the invention using Complement-fixation on virus. The ability of mAbs to bind to virus and fix complement directly in solution will be evaluated by detecting cleavage products of C3 that occur after fixation using methods known in the art such as those disclosed in Manderson et al., 2001, J Exp Med 194:747-56. WNV or DEN virus (negative control) will be incubated with anti-WNV mAbs against E in the presence of serum from wild type mice at 37° C. to enable C3 binding. Samples will be denatured with detergent, immunoprecipitated with goat anti-mouse C3, and subjected to Western blot analysis with rabbit polyclonal antibodies against C3. If complement fixation occurs, the C3α chain ($M_r$ of 100) will be cleaved and increased levels of C3d ($M_r$ of 40) will be detected. As an additional control, mAbs and WNV will also be incubated with factor B $-/-$ and C1q $-/-$ serum. If complement fixation on virus requires antibodies (and uses the classical pathway of complement activation), a deficiency of C1q but not factor B will prevent conversion of C3 to C3d. The use of these complement-deficient sera will confirm that antibody binding triggers C3 activation directly and rule out C3 activation that occurs spontaneously in solution (Manderson et al., 2001, J Exp Med 194:747-56) or via the alternative pathway. A point scale will be assigned based on whether mAbs facilitate direct complement-fixation on WNV: no C3 fixation=0 points, C3 fixation=2 points.

In yet other embodiments, the invention encompasses characterization of the antibodies of the invention using Antibody-dependent cell-mediated cytotoxicity (ADCC) assays known in the art and encompassed herein. The ability of mAbs to promote ADCC of WNV-infected cells will be evaluated according to previously described assays (Kurane et al., 1984, J Virol 52:223-30; Meguro et al., 1979, J Immunol 122:2521-6; Zhang et al., 1992, Acta Virol 36:533-40). MC57GL mouse fibroblasts will be infected with WNV for 24 hours, labeled with $^{51}Cr$, incubated with purified anti-WNV or control mAbs, and mixed with different concentrations of washed syngeneic peripheral blood mononuclear cells (PBMC) isolated from WNV-naïve mice. After incubation (12 to 16 h at 37° C.), supernatants will be harvested and ADCC activity will be measured by scintillation counting. A point scale will be assigned based on the percentage of cells that are specifically lysed in the presence of mAb with an effector:target ratio of 50:1: $<10\%=0$ points, $10-40\%=1$ point, $>40\%=2$ points. (e) Avidity. Because passive administration of high-affinity non-neutralizing mAbs can prevent lethal encephalitis caused by Sindbis virus (Schmaljohn et al., 1982, Nature 297:70-2), mAbs will also be evaluated for their relative avidity. Avidity will be assessed by the constant antigen varying antibody method (Tyler et al., 1993, J Virol 67:3446-53; Virgin et al., 1991, J Virol 65:6772-81). A fixed quantity of recombinant E or NS1 protein will be adsorbed to a microtiter well, incubated with varying concentrations of $I^{125}$-labeled purified mAb, and evaluated for reactivity by scintillation counting. Competition studies will be performed with a 100-fold excess of unlabeled antibody so that a $K_D$ can be determined by Scatchard analysis. A point scale will be assigned based on the relative avidity of the bivalent mAbs for purified WNV proteins: $>10^{-6}M=0$ points, $10^{-6}-10^{-8}M=1$ point, $<10^{-8}M=2$ points.

As mentioned, the point system is designed to facilitate ranking and selection of the mAbs with the greatest potential inhibitory activity of three categories will be selected for further competition binding and in vivo studies.

5.3 Polynucleotides Encoding an Antibody

The present invention also includes polynucleotides that encode the antibodies of the invention (e.g., a mouse monoclonal antibody produced from clones E16, E24, or E34, having ATCC Accession Nos. PTA-6050, PTA-6051, and PTA-6052, respectively), or other monoclonal antibodies produced by immunization methods of the invention, and humanized versions thereof, and methods for producing same.

The present invention also encompasses the polynucleotide encoding the light chain of an antibody with ATCC accession numbers PTA-6050, PTA-6051, or PTA-6052, as disclosed in SEQ ID NOs. 1, 5, or 9, respectively. The present invention encompass the polynucleotide encoding the heavy chain of an antibody with ATCC accession numbers PTA-6050, PTA-6051, or PTA-6052, as disclosed in SEQ ID NOs. 3, 7, or 11, respectively.

The methods of the invention also encompass polynucleotides that hybridize under various stringency, e.g., high stringency, intermediate or lower stringency conditions, to polynucleotides that encode an antibody of the invention. The hybridization can be performed under various conditions of stringency. By way of example and not limitation, procedures using conditions of low stringency are as follows (see also Shilo and Weinberg, 1981, *Proc. Natl. Acad. Sci. U.S.A.* 78, 6789-6792). Filters containing DNA are pretreated for 6 h at 40° C. in a solution containing 35% formamide, 5X SSC, 50 mM Tris-HCl (pH 7.5), 5 mM EDTA, 0.1% PVP, 0.1% Ficoll, 1% BSA, and 500 µg/ml denatured salmon sperm DNA. Hybridizations are carried out in the same solution with the following modifications: 0.02% PVP, 0.02% Ficoll, 0.2% BSA, 100 µg/ml salmon sperm DNA, 10% (wt/vol) dextran sulfate, and 5-20×10$^6$ cpm $^{32}$P-labeled probe is used. Filters are incubated in hybridization mixture for 18-20 h at 40° C., and then washed for 1.5 h at 55° C. in a solution containing 2X SSC, 25 mM Tris-HCl (pH 7.4), 5 mM EDTA, and 0.1% SDS. The wash solution is replaced with fresh solution and incubated an additional 1.5 h at 60° C. Filters are blotted dry and exposed for autoradiography. If necessary, filters are washed for a third time at 65-68° C. and re-exposed to film. Other conditions of low stringency which may be used are well known in the art (e.g., as employed for cross-species hybridizations). By way of example and not limitation, procedures using conditions of high stringency are as follows. Prehybridization of filters containing DNA is carried out for 8 h to overnight at 65° C. in buffer composed of 6X SSC, 50 mM Tris-HCl (pH 7.5), 1 mM EDTA, 0.02% PVP, 0.02% Ficoll, 0.02% BSA, and 500 µg/ml denatured salmon sperm DNA. Filters are hybridized for 48 h at 65° C. in prehybridization mixture containing 100 µg/ml denatured salmon sperm DNA and 5-20×10$^6$ cpm of $^{32}$P-labeled probe. Washing of filters is done at 37° C. for 1 h in a solution containing 2X SSC, 0.01% PVP, 0.01% Ficoll, and 0.01% BSA. This is followed by a wash in 0.1X SSC at 50° C. for 45 min before autoradiography. Other conditions of high stringency which may be used are well known in the art. Selection of appropriate conditions for such stringencies is well known in the art (see e.g., Sambrook et al., 1989, Molecular Cloning, A Laboratory Manual, 2d Ed., Cold Spring Harbor Laboratory Press, Cold Spring Harbor, N.Y.; see also, Ausubel et al., eds., in the Current Protocols in Molecular Biology series of laboratory technique manuals, © 1987-1997, Current Protocols, © 1994-1997 John Wiley and Sons, Inc.; see especially, Dyson, 1991, "Immobilization of nucleic acids and hybridization analysis," In: Essential Molecular Biology: A Practical Approach, Vol. 2, T. A. Brown, ed., pp. 111-156, IRL Press at Oxford University Press, Oxford, UK).

The polynucleotides may be obtained, and the nucleotide sequence of the polynucleotides determined, by any method known in the art.

A polynucleotide encoding an antibody may be generated from nucleic acid from a suitable source (e.g., a cDNA library generated from, or nucleic acid, preferably poly A+ RNA, isolated from, any tissue or cells expressing the antibody, such as hybridoma cells selected to express an antibody of the invention) by hybridization with Ig specific probes and/or PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method well known in the art.

Once the nucleotide sequence of the antibody is determined, the nucleotide sequence of the antibody may be manipulated using methods well known in the art for the manipulation of nucleotide sequences, e.g., recombinant DNA techniques, site directed mutagenesis, PCR, etc. (see, for example, the techniques described in Sambrook et al., 1990, *Molecular Cloning, A Laboratory Manual*, 2d Ed., Cold Spring Harbor Laboratory, Cold Spring Harbor, N.Y. and Ausubel et al., eds., 1998, Current Protocols in Molecular Biology, John Wiley & Sons, NY, which are both incorporated by reference herein in their entireties), to generate antibodies having a different amino acid sequence, for example to create amino acid substitutions, deletions, and/or insertions.

In a specific embodiment, one or more of the CDRs are inserted within framework regions using routine recombinant DNA techniques. The framework regions may be naturally occurring or consensus framework regions, and preferably human framework regions (see, e.g., Chothia et al., 1998, *J. Mol. Biol.* 278: 457-479 for a listing of human framework regions). Preferably, the polynucleotide generated by the combination of the framework regions and CDRs encodes an antibody that specifically binds to a flaviviral antigen. Preferably, as discussed supra, one or more amino acid substitutions may be made within the framework regions, and, preferably, the amino acid substitutions improve binding of the antibodies of the invention to a flaviviral antigen. In another embodiment, human libraries or any other libraries available in the art, can be screened by standard techniques known in the art, to clone the nucleic acids encoding the antibodies of the invention.

5.4 Recombinant Expression of Antibodies

Once a nucleic acid sequence encoding an antibody of the invention has been obtained, the vector for the production of the antibody may be produced by recombinant DNA technology using techniques well known in the art. Methods which are well known to those skilled in the art can be used to construct expression vectors containing the antibody coding sequences and appropriate transcriptional and translational control signals. These methods include, for example, in vitro recombinant DNA techniques, synthetic techniques, and in vivo genetic recombination (See, for example, the techniques described in Sambrook et al., 1990, *Molecular Cloning, A Laboratory Manual*, 2d Ed., Cold Spring Harbor Laboratory, Cold Spring Harbor, N.Y. and Ausubel et al. eds., 1998, *Current Protocols in Molecular Biology*, John Wiley & Sons, NY).

An expression vector comprising the nucleotide sequence of an antibody can be transferred to a host cell by conventional techniques (e.g., electroporation, liposomal transfection, and calcium phosphate precipitation) and the transfected cells are then cultured by conventional techniques to produce the antibody of the invention. In specific embodiments, the expression of the antibody is regulated by a constitutive, an inducible or a tissue-specific promoter.

The host cells used to express the recombinant antibodies of the invention may be either bacterial cells such as *Escherichia coli*, or, preferably, eukaryotic cells, especially for the expression of whole recombinant immunoglobulin molecule. In particular, mammalian cells such as Chinese hamster ovary cells (CHO), in conjunction with a vector such as the major intermediate early gene promoter element from human cytomegalovirus is an effective expression system for immunoglobulins (Foecking et al., 1998, *Gene* 45: 101; Cockett et al., 1990, *Bio/Technology* 8:2).

A variety of host-expression vector systems may be utilized to express the antibodies of the invention. Such host-expression systems represent vehicles by which the coding sequences of the antibodies may be produced and subsequently purified, but also represent cells which may, when transformed or transfected with the appropriate nucleotide coding sequences, express the antibodies of the invention in situ. These include, but are not limited to, microorganisms such as bacteria (e.g., *E. coli* and *B. subtilis*) transformed with recombinant bacteriophage DNA, plasmid DNA or cosmid DNA expression vectors containing immunoglobulin coding sequences; yeast (e.g., *Saccharomyces Pichia*) transformed with recombinant yeast expression vectors containing immunoglobulin coding sequences; insect cell systems infected with recombinant virus expression vectors (e.g., baculovirus) containing the immunoglobulin coding sequences; plant cell systems infected with recombinant virus expression vectors (e.g., cauliflower mosaic virus (CaMV) and tobacco mosaic virus (TMV)) or transformed with recombinant plasmid expression vectors (e.g., Ti plasmid) containing immunoglobulin coding sequences; or mammalian cell systems (e.g., COS, CHO, BHK, 293, 293T, 3T3 cells, lymphotic cells (see U.S. Pat. No. 5,807,715), Per C.6 cells (rat retinal cells developed by Crucell)) harboring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems, a number of expression vectors may be advantageously selected depending upon the use intended for the antibody being expressed. For example, when a large quantity of such a protein is to be produced, for the generation of pharmaceutical compositions of an antibody, vectors which direct the expression of high levels of fusion protein products that are readily purified may be desirable. Such vectors include, but are not limited, to the *E. coli* expression vector pUR278 (Ruther et al., 1983, *EMBO J.* 2:1791), in which the antibody coding sequence may be ligated individually into the vector in frame with the lac Z coding region so that a fusion protein is produced; pIN vectors (Inouye & Inouye, 1985, *Nucleic Acids Res.* 13:3101-3109; Van Heeke & Schuster, 1989, *J. Biol. Chem.* 24:5503-5509); and the like. pGEX vectors may also be used to express foreign polypeptides as fusion proteins with glutathione S-transferase (GST). In general, such fusion proteins are soluble and can easily be purified from lysed cells by adsorption and binding to a matrix glutathione-agarose beads followed by elution in the presence of free gluta-thione. The pGEX vectors are designed to include thrombin or factor Xa protease cleavage sites so that the cloned target gene product can be released from the GST moiety.

In an insect system, *Autographa californica* nuclear polyhedrosis virus (AcNPV) is used as a vector to express foreign genes. The virus grows in *Spodoptera frugiperda* cells. The antibody coding sequence may be cloned individually into non-essential regions (e.g., the polyhedrin gene) of the virus and placed under control of an AcNPV promoter (e.g., the polyhedrin promoter).

In mammalian host cells, a number of viral-based expression systems may be utilized. In cases where an adenovirus is used as an expression vector, the antibody coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the immunoglobulin molecule in infected hosts (see, e.g., Logan & Shenk, 1984, *Proc. Natl. Acad. Sci. USA* 81:355-359). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., 1987, *Methods in Enzymol.* 153:51-544).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include, but are not limited to, CHO, VERY, BHK, Hela, COS, MDCK, 293, 293T, 3T3, WI38, BT483, Hs578T, HTB2, BT20 and T47D, CRL7030 and Hs578Bst.

For long-term, high-yield production of recombinant proteins, stable expression is preferred. For example, cell lines which stably express an antibody of the invention may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the antibodies of the invention. Such engineered cell lines may be particularly useful in screening and evaluation of compounds that interact directly or indirectly with the antibodies of the invention.

A number of selection systems may be used, including but not limited to the herpes simplex virus thymidine kinase (Wigler et al., 1977, *Cell* 11:223), hypoxanthine-guanine phosphoribosyltransferase (Szybalska & Szybalski, 1992, *Proc. Natl. Acad. Sci. USA* 48:202), and adenine phosphoribosyltransferase (Lowy et al., 1980, *Cell* 22:817) genes can be employed in tk-, hgprt- or aprt-cells, respectively. Also, antimetabolite resistance can be used as the basis of selection for the following genes: dhfr, which confers resistance to methotrexate (Wigler et al., 1980, *Proc. Natl. Acad. Sci. USA* 77:357; O'Hare et al., 1981, *Proc. Natl. Acad. Sci. USA* 78:1527); gpt, which confers resistance to mycophenolic acid (Mulligan & Berg, 1981, *Proc. Natl. Acad Sci. USA* 78:2072); neo, which confers resistance to the aminoglycoside G-418 *Clinical Pharmacy* 12:488-505; Wu and Wu, 1991, 3:87-95; Tolstoshev, 1993, *Ann. Rev. Pharmacol. Toxicol.* 32:573-596; Mulligan, 1993, *Science* 260:926-932; and Morgan and Anderson, 1993, *Ann. Rev. Biochem.* 62:191-217; May, 1993, *TIB TECH* 11(5):155-215); and hygro, which confers resistance to hygromycin (Santerre et al., 1984, *Gene* 30:147). Methods commonly known in the art of recombinant DNA technology which can be used are described in Ausubel et al. (eds.), 1993, *Current Protocols in Molecular Biology,* John Wiley & Sons, NY; Kriegler, 1990, *Gene Transfer and Expression, A Laboratory Manual,* Stockton Press, NY; and in Chapters 12 and 13, Dracopoli et al. (eds), 1994, *Current Protocols in Human Genetics,* John Wiley & Sons, NY.; and Colberre-Garapin et al., 1981, *J. Mol. Biol.* 150:1.

The expression levels of an antibody of the invention can be increased by vector amplification (for a review, see Bebbington and Hentschel, *The use of vectors based on gene amplification for the expression of cloned zenes in mammalian cells in DNA cloning,* Vol. 3. (Academic Press, New York, 1987)). When a marker in the vector system expressing an antibody is amplifiable, increase in the level of inhibitor present in culture of host cell will increase the number of copies of the marker gene. Since the amplified region is associated with the nucleotide sequence of the antibody, production of the antibody will also increase (Crouse et al., 1983, *Mol. Cell. Biol.* 3:257).

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes both heavy and light chain polypeptides. In such situations, the light chain should be placed before the heavy chain to avoid an excess of toxic free heavy chain (Proudfoot, 1986, *Nature* 322:52; Kohler, 1980,

*Proc. Natl. Acad. Sci. USA* 77:2197). The coding sequences for the heavy and light chains may comprise cDNA or genomic DNA.

Once the antibody of the invention has been recombinantly expressed, it may be purified by any method known in the art for purification of an antibody, for example, by chromatography (e.g., ion exchange, affinity, particularly by affinity for the specific antigen after Protein A, and sizing column chromatography), centrifugation, differential solubility, or by any other standard technique for the purification of proteins.

5.5 Prophylactic and Therapeutic Uses of Antibodies

The present invention is directed to antibody-based therapies which involve administering antibodies of the invention or fragments thereof to a mammal, preferably a human, for preventing, treating, or ameliorating one or more symptoms associated with a flaviviral infection, particularly an WNV infection. Prophylactic and therapeutic compounds of the invention include, but are not limited to, antibodies of the invention (including fragments, analogs and derivatives thereof as described herein) and nucleic acids encoding antibodies of the invention (including fragments, analogs and derivatives thereof and anti-idiotypic antibodies as described herein). Antibodies of the invention or fragments thereof may be provided in pharmaceutically acceptable compositions as known in the art or as described herein.

Antibodies of the present invention or fragments thereof that function as antagonists of a flaviviral infection can be administered to a mammal, preferably a human, to treat, prevent or ameliorate one or more symptoms associated with a flaviviral infection. For example, antibodies or fragments thereof which disrupt or prevent the interaction between a flaviviral antigen and its host cell receptor may be administered to a mammal, preferably a human, to treat, prevent or ameliorate one or more symptoms associated with a flaviviral infection.

The present invention provides methods for treating, preventing, or ameliorating a flaviviral infection by administration of one or more antibodies of the invention. In a specific embodiment, the invention encompasses methods for treating, preventing, or ameliorating a WNV infection comprising administering a first antibody that immunospecifically binds a structural protein of WNV, e.g., E protein, and a second antibody that binds a non-structural protein of WNV, e.g., NS1 protein. Although not intending to be bound by a particular mechanism of action such combination regimens are more effective than single antibody treatment regimens because the RNA-dependent RNA polymerase of WNV has a high error rate and thus a potential to rapidly alter immunodominant residues. In other specific embodiments, the invention encompasses methods for treating, preventing, or ameliorating a WNV infection comprising administering a first antibody that immunospecifically binds an epitope of a structural protein of WNV, e.g., E protein, and a second antibody that binds the same structural protein of WNV but binds a different epitope.

In a specific embodiment, an antibody or fragment thereof prevents flavivirus, e.g. WNV, from binding to its host cell receptor by at least 99%, at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10% relative to flaviviral binding to its host cell receptor in the absence of said antibodies or antibody fragments. In another embodiment, a combination of antibodies, a combination of antibody fragments, or a combination of antibodies and antibody fragments prevent flaviviral from binding to its host cell receptor by at least 99%, at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10% relative to WNV binding to its host cell receptor in the absence of said antibodies and/or antibody fragments.

One or more antibodies of the present invention or fragments thereof that immunospecifically bind to one or more flaviviral antigens, particularly WNV antigen, may be used locally or systemically in the body as a therapeutic. The antibodies of this invention or fragments thereof may also be advantageously utilized in combination with other monoclonal or chimeric antibodies, or with lymphokines or hematopoietic growth factors (such as, e.g., IL-2, IL-3 and IL-7), which, for example, serve to increase the number or activity of effector cells which interact with the antibodies. The antibodies of this invention or fragments thereof may also be advantageously utilized in combination with other monoclonal or chimeric antibodies, or with lymphokines or hematopoietic growth factors (such as, e.g., IL-2, IL-3 and IL-7), which, for example, serve to increase the immune response. The antibodies of this invention or fragments thereof may also be advantageously utilized in combination with one or more drugs used to treat flaviviral infections, particularly WNV infections, such as, for example anti-viral agents. Examples of anti-viral agents include, but are not limited to, protease inhibitors, nucleoside reverse transcriptase inhibitors, non-nucleoside reverse transcriptase inhibitors and nucleoside analogs, zidovudine, acyclovir, gangcyclovir, vidarabine, idoxuridine, trifluridine, and ribavirin, as well as foscamet, amantadine, rimantadine, saquinavir, indinavir, amprenavir, lopinavir, ritonavir, the alpha-interferons; adefovir, clevadine, entecavir, and pleconaril. The invention encompasses any other anti-viral agent being developed and known to those skilled in the art.

The antibodies of the invention may be administered alone or in combination with other types of treatments (e.g., hormonal therapy, immunotherapy, and anti-inflammatory agents). Generally, administration of products of a species origin or species reactivity (in the case of antibodies) that is the same species as that of the patient is preferred. Thus, in a preferred embodiment, human or humanized antibodies, fragments derivatives, analogs, or nucleic acids, are administered to a human patient for therapy or prophylaxis.

It is preferred to use high affinity and/or potent in vivo inhibiting antibodies and/or neutralizing antibodies that immunospecifically bind to a flaviviral antigen, particularly WNV antigen, for prevention of flaviviral infection, particularly WNV infection and therapy for flaviviral infection, particularly WNV infection. It is also preferred to use polynucleotides encoding high affinity and/or potent in vivo inhibiting antibodies and/or neutralizing antibodies that immunospecifically bind to a a flaviviral antigen, particularly WNV antigen, for both immunoassays directed to WNV and therapy for WNV infection. Such antibodies or fragments thereof will preferably have an affinity for the WNV E protein and NS1 protein. In a specific embodiment, a mammal, preferably a human, is administered a therapeutic or pharmaceutical composition comprising one or more antibodies of the present invention or fragments thereof for the treatment, prevention or amelioration of one or more symptoms associated with a flavirial infection, particularly WNF infection.

Prophylactic and therapeutic compounds that may be used in combination with the antibodies of the invention include, but are not limited to, proteinaceous molecules, including, but not limited to, peptides, polypeptides, proteins, including post-translationally modified proteins, antibodies, etc.; small molecules (less than 1000 daltons), inorganic or organic compounds; nucleic acid molecules including, but not limited to, double-stranded or single-stranded DNA, double-stranded or single-stranded RNA, as well as triple helix nucleic acid molecules. Prophylactic and therapeutic compounds can be derived from any known organism (including, but not limited to, animals, plants, bacteria, fungi, and protista, or viruses) or from a library of synthetic molecules.

In certain embodiments, one or more antibodies of the invention are administered to a mammal, preferably a human, concurrently with one or more other therapeutic agents, e.g., anti-viral agents, useful for the treatment or prevention of a flaviviral infection, particularly WNV infection. The term "concurrently" is not limited to the administration of prophylactic or therapeutic agents at exactly the same time, but rather it is meant that antibodies of the invention and the other agent are administered to a subject in a sequence and within a time interval such that the antibodies of the invention can act together with the other agent to provide an increased benefit than if they were administered otherwise. For example, each prophylactic or therapeutic agent may be administered at the same time or sequentially in any order at different points in time; however, if not administered at the same time, they should be administered sufficiently close in time so as to provide the desired therapeutic or prophylactic effect. Each therapeutic agent can be administered separately, in any appropriate form and by any suitable route.

In various embodiments, the prophylactic or therapeutic agents are administered less than 1 hour apart, at about 1 hour apart, at about 1 hour to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, no more than 24 hours apart or no more than 48 hours apart. In preferred embodiments, two or more components are administered within the same patient visit.

The dosage amounts and frequencies of administration provided herein are encompassed by the terms therapeutically effective and prophylactically effective. The dosage and frequency further will typically vary according to factors specific for each patient depending on the specific therapeutic or prophylactic agents administered, the severity and type of cancer, the route of administration, as well as age, body weight, response, and the past medical history of the patient. Suitable regimens can be selected by one skilled in the art by considering such factors and by following, for example, dosages reported in the literature and recommended in the *Physician's Desk Reference* (56$^{th}$ ed., 2002).

5.6 Methods of Administration of Antibodies

The invention provides methods of treatment, prophylaxis, and amelioration of one or more symptoms associated with flaviviral infection, particularly WNV infection, by administrating to a subject of an effective amount of an antibody of the invention or fragment thereof, or pharmaceutical composition comprising an antibody of the invention or fragment thereof. In a preferred aspect, an antibody or fragment thereof is substantially purified (i.e., substantially free from substances that limit its effect or produce undesired side-effects). The subject is preferably a mammal such as non-primate (e.g., cows, pigs, horses, cats, dogs, rats etc.) and a primate (e.g., monkey such as a cynomolgous monkey and a human). In a preferred embodiment, the subject is a human, particularly a human who is at an increased risk of flaviviral infection, particularly WNV infection. In another preferred embodiment, the subject is a human infant, an elderly human, or a human with an impaired immune system.

The invention provides methods and pharmaceutical compositions comprising antibodies of the invention. The invention also provides methods of treatment, prophylaxis, and amelioration of one or more symptoms associated with flaviviral infection by administering to a subject an effective amount of a fusion protein or a conjugated molecule of the invention, or a pharmaceutical composition comprising a fusion protein or conjugated molecules of the invention. In a preferred aspect, an antibody or fusion protein or conjugated molecule, is substantially purified (i.e., substantially free from substances that limit its effect or produce undesired side-effects). In a specific embodiment, the subject is an animal, preferably a mammal such as non-primate (e.g., cows, pigs, horses, cats, dogs, rats etc.) and a primate (e.g., monkey such as, a cynomolgous monkey and a human). In a preferred embodiment, the subject is a human.

Various delivery systems are known and can be used to administer a composition comprising antibodies of the invention, e.g., encapsulation in liposomes, microparticles, microcapsules, recombinant cells capable of expressing the antibody or fusion protein, receptor-mediated endocytosis (See, e.g., Wu and Wu, 1987, *J. Biol. Chem.* 262:4429-4432), construction of a nucleic acid as part of a retroviral or other vector, etc.

In some embodiments, the antibodies of the invention are formulated in liposomes for targeted delivery of the antibodies of the invention. Liposomes are vesicles comprised of concentrically ordered phospholipid bilayers which encapsulate an aqueous phase. Liposomes typically comprise various types of lipids, phospholipids, and/or surfactants. The components of liposomes are arranged in a bilayer configuration, similar to the lipid arrangement of biological membranes. Liposomes are particularly preferred delivery vehicles due, in part, to their biocompatibility, low immunogenicity, and low toxicity. Methods for preparation of liposomes are known in the art and are encompassed within the invention, see, e.g., Epstein et al., 1985, *Proc. Natl. Acad. Sci. USA*, 82: 3688; Hwang et al., 1980 *Proc. Natl. Acad. Sci. USA*, 77: 4030-4; U.S. Pat. Nos. 4,485,045 and 4,544,545; all of which are incorporated herein by reference in their entireties.

The invention also encompasses methods of preparing liposomes with a prolonged serum half-life, i.e., enhanced circulation time, such as those disclosed in U.S. Pat. No. 5,013,556. Preferred liposomes used in the methods of the invention are not rapidly cleared from circulation, i.e., are not taken up into the mononuclear phagocyte system (MPS). The invention encompasses sterically stabilized liposomes which are prepared using common methods known to one skilled in the art. Although not intending to be bound by a particular mechanism of action, sterically stabilized liposomes contain lipid components with bulky and highly flexible hydrophilic moieties, which reduces the unwanted reaction of liposomes with serum proteins, reduces oposonization with serum components and reduces recognition by MPS. Sterically stabilized liposomes are preferably prepared using polyethylene glycol. For preparation of liposomes and sterically stabilized liposome, see, e.g., Bendas et al., 2001 *BioDrugs*, 15(4): 215-224; Allen et al., 1987 *FEBS Lett.* 223: 42-6; Klibanov et al., 1990 *FEBS Lett.*, 268: 235-7; Blum et al., 1990, *Biochim. Biophys. Acta.*, 1029: 91-7; Torchilin et al., 1996, *J. Liposome Res.* 6: 99-116; Litzinger et al., 1994, *Biochim. Biophys. Acta*, 1190: 99-107; Maruyama et al., 1991, *Chem. Pharm. Bull.*, 39: 1620-2; Klibanov et al., 1991, *Biochim Biophys Acta*, 1062; 142-8; Allen et al., 1994, *Adv. Drug Deliv. Rev*, 13: 285-309; all of which are incorporated herein by reference in their entireties. The invention also encompasses liposomes that are adapted for specific organ targeting, see, e.g., U.S. Pat. No. 4,544,545. Particularly useful liposomes for use in the compositions and methods of the invention can be generated by reverse phase evaporation method with a lipid composition comprising phosphatidylcholine, cholesterol, and PEG derivatized phosphatidylethanolamine (PEG-PE). Liposomes are extruded through filters of defined pore size to yield liposomes with the desired diameter. In some embodiments, a fragment of an antibody of the invention, e.g., F(ab'), may be conjugated to the liposomes using previously described methods, see, e.g., Martin et al., 1982, *J. Biol. Chem.* 257: 286-288, which is incorporated herein by reference in its entirety.

The antibodies of the invention may also be formulated as immunoliposomes. Immunoliposomes refer to a liposomal composition, wherein an antibody of the invention or a fragment thereof is linked, covalently or non-covalently to the liposomal surface. The chemistry of linking an antibody to the liposomal surface is known in the art and encompassed within the invention, see, e.g., Allen et al., 1995, *Stealth Liposomes, Boca Rotan: CRC Press*, 233-44; Hansen et al., 1995, *Biochim. Biophys. Acta*, 1239: 133-44; which are incorporated herein by reference in their entirety. In most preferred embodiments, immunoliposomes for use in the methods and compositions of the invention are further sterically stabilized. Preferably, the antibodies of the invention are linked covalently or non-covalently to a hydrophobic anchor, which is stably rooted in the lipid bilayer of the liposome. Examples of hydrophobic anchors include but are not limited to phospholipids, e.g., phosoatidylethanolamine (PE), phosphatidylinositol (PI). To achieve a covalent linkage between an antibody and a hydrophobic anchor, any of the known biochemical strategies in the art may be used, see, e.g., J. Thomas August, ed., 1997, *Gene Therapy: Advances in Pharmacology*, Volume 40, Academic Press, San Diego, Calif., p. 399-435, which is incorporated herein by reference in its entirety. For example, a functional group on an antibody molecule may react with an active group on a liposome associated hydrophobic anchor, e.g., an amino group of a lysine side chain on an antibody may be coupled to liposome associated N-glutaryl-phosphatidylethanolamine activated with water-soluble carbodiimide; or a thiol group of a reduced antibody can be coupled to liposomes via thiol reactive anchors such as pyridylthiopropionyl-phosphatidylethanolamine. See, e.g., Dietrich et al., 1996, *Biochemistry*, 35: 1100-1105; Loughrey et al., 1987, *Biochim. Biophys. Acta*, 901: 157-160; Martin et al., 1982, *J. Biol. Chem.* 257: 286-288; Martin et al., 1981, *Biochemistry*, 20: 4429-38; all of which are incorporated herein by reference in their entireties.

The invention encompasses immunoliposomes comprising an antibody of the invention or a fragment thereof. In some embodiments, the immunoliposomes further comprise one or more additional therapeutic agents, such as those disclosed herein.

The immunoliposomal compositions of the invention comprise one or more vesicle forming lipids, an antibody of the invention or a fragment or derivative thereof, and optionally a hydrophilic polymer. A vesicle forming lipid is preferably a lipid with two hydrocarbon chains, such as acyl chains and a polar head group. Examples of vesicle forming lipids include phospholipids, e.g., phosphatidylcholine, phosphatidylethanolamine, phosphatidic acid, phosphatidylinositol, sphingomyelin, and glycolipids, e.g., cerebrosides, gangliosides. Additional lipids useful in the formulations of the invention are known to one skilled in the art and encompassed within the invention. In some embodiments, the immunoliposomal compositions further comprise a hydrophilic polymer, e.g., polyethylene glycol, and gnaglioside GM1, which increases the serum half life of the liposome. Methods of conjugating hydrophilic polymers to liposomes are well known in the art and encompassed within the invention. For a review of immunoliposomes and methods of preparing them, see, e.g., PCT International Publication No. WO 97/38731, Vingerhoeads et al., 1994, *Immunomethods*, 4: 259-72; Maruyama, 2000, *Biol. Pharm. Bull.* 23(7): 791-799; Abra et al., 2002, *Journal of Liposome Research*, 12(1&2): 1-3; Park, 2002, *Bioscience Reports*, 22(2): 267-281; Bendas et al., 2001 *BioDrugs*, 14(4): 215-224, J. Thomas August, ed., 1997, *Gene Therapy: Advances in Pharmacology*, Volume 40, Academic Press, San Diego, Calif., p. 399-435, all of which are incorporated herein by reference in their entireties.

Methods of administering an antibody of the invention include, but are not limited to, parenteral administration (e.g., intradermal, intramuscular, intraperitoneal, intravenous and subcutaneous), epidural, and mucosal (e.g., intranasal and oral routes). In a specific embodiment, the antibodies of the invention are administered intramuscularly, intravenously, or subcutaneously. The compositions may be administered by any convenient route, for example, by infusion or bolus injection, by absorption through epithelial or mucocutaneous linings (e.g., oral mucosa, rectal and intestinal mucosa, etc.) and may be administered together with other biologically active agents. Administration can be systemic or local. In addition, pulmonary administration can also be employed, e.g., by use of an inhaler or nebulizer, and formulation with an aerosolizing agent. See, e.g., U.S. Pat. Nos. 6,019,968; 5,985, 20; 5,985,309; 5,934,272; 5,874,064; 5,855,913; 5,290,540; and 4,880,078; and PCT Publication Nos. WO 92/19244; WO 97/32572; WO 97/44013; WO 98/31346; and WO 99/66903, each of which is incorporated herein by reference in its entirety.

The invention also provides that the antibodies of the invention are packaged in a hermetically sealed container such as an ampoule or sachette indicating the quantity of antibody. In one embodiment, the antibodies of the invention are supplied as a dry sterilized lyophilized powder or water free concentrate in a hermetically sealed container and can be reconstituted, e.g., with water or saline to the appropriate concentration for administration to a subject. Preferably, the antibodies of the invention are supplied as a dry sterile lyophilized powder in a hermetically sealed container at a unit dosage of at least 5 mg, more preferably at least 10 mg, at least 15 mg, at least 25 mg, at least 35 mg, at least 45 mg, at least 50 mg, or at least 75 mg. The lyophilized antibodies of the invention should be stored at between 2 and 8° C. in their original container and the antibodies should be administered within 12 hours, preferably within 6 hours, within 5 hours, within 3 hours, or within 1 hour after being reconstituted. In an alternative embodiment, antibodies of the invention are supplied in liquid form in a hermetically sealed container indicating the quantity and concentration of the antibody, fusion protein, or conjugated molecule. Preferably, the liquid form of the antibodies are supplied in a hermetically sealed container at least 1 mg/ml, more preferably at least 2.5 mg/ml, at least 5 mg/ml, at least 8 mg/ml, at least 10 mg/ml, at least 15 mg/kg, at least 25 mg/ml, at least 50 mg/ml, at least 100 mg/ml, at least 150 mg/ml, at least 200 mg/ml of the antibodies.

The amount of the composition of the invention which will be effective in the treatment, prevention or amelioration of one or more symptoms associated with a a flaviviral infection, particularly WNV infection, can be determined by standard clinical techniques. The precise dose to be employed in the formulation will also depend on the route of administration, and the seriousness of the condition, and should be decided according to the judgment of the practitioner and each patient's circumstances. Effective doses may be extrapolated from dose-response curves derived from in vitro or animal model test systems.

For antibodies encompassed by the invention, the dosage administered to a patient is typically 5 mg/kg to 25 mg/kg of the patient's body weight. Preferably, the dosage administered to a patient is between 5 mg/kg and 25 mg/kg of the patient's body weight. Generally, human antibodies have a longer half-life within the human body than antibodies from other species due to the immune response to the foreign polypeptides. Thus, lower dosages of human antibodies and less frequent administration is often possible. Further, the dosage and frequency of administration of antibodies of the invention or fragments thereof may be reduced by enhancing uptake and tissue penetration of the antibodies by modifications such as, for example, lipidation.

In one embodiment, the dosage of the antibodies of the invention administered to a patient are 0.01 mg to 1000 mg, when used as single agent therapy. In another embodiment the antibodies of the invention are used in combination with other therapeutic compositions and the dosage administered to a patient are lower than when said antibodies are used as a single agent therapy.

In a specific embodiment, it may be desirable to administer the pharmaceutical compositions of the invention locally to the area in need of treatment; this may be achieved by, for example, and not by way of limitation, local infusion, by injection, or by means of an implant, said implant being of a porous, non-porous, or gelatinous material, including membranes, such as sialastic membranes, or fibers. Preferably, when administering an antibody of the invention, care must be taken to use materials to which the antibody or the fusion protein does not absorb.

In another embodiment, the compositions can be delivered in a vesicle, in particular a liposome (See Langer, *Science* 249:1527-1533 (1990); Treat et al., in *Liposomes in the Therapy of Infectious Disease and Cancer,* Lopez-Berestein and Fidler (eds.), Liss, N. Y., pp. 353-365 (1989); Lopez-Berestein, ibid., pp. 3 17-327; see generally ibid.).

In yet another embodiment, the compositions can be delivered in a controlled release or sustained release system. Any technique known to one of skill in the art can be used to produce sustained release formulations comprising one or more antibodies of the invention. See, e.g., U.S. Pat. No. 4,526,938; PCT publication WO 91/05548; PCT publication WO 96/20698; Ning et al., 1996, "Intratumoral Radioimmunotheraphy of a Human Colon Cancer Xenograft Using a Sustained-Release Gel," *Radiotherapy & Oncology* 39:179-189, Song et al., 1995, "Antibody Mediated Lung Targeting of Long-Circulating Emulsions," *PDA Journal of Pharmaceutical Science & Technology* 50:372-397; Cleek et al., 1997, "Biodegradable Polymeric Carriers for a bFGF Antibody for Cardiovascular Application," *Pro. Int'l. Symp. Control. Rel. Bioact. Mater.* 24:853-854; and Lam et al., 1997, "Microencapsulation of Recombinant Humanized Monoclonal Antibody for Local Delivery," *Proc. Int'l. Symp. Control Rel. Bioact. Mater.* 24:759-760, each of which is incorporated herein by reference in its entirety. In one embodiment, a pump may be used in a controlled release system (See Langer, supra; Sefton, 1987, *CRC Crit. Ref Biomed. Eng.* 14:20; Buchwald et al., 1980, Surgery 88:507; and Saudek et al., 1989, *N. Engl. J. Med.* 321:574). In another embodiment, polymeric materials can be used to achieve controlled release of antibodies (see e.g., *Medical Applications of Controlled Release,* Langer and Wise (eds.), CRC Pres., Boca Raton, Fla. (1974); Controlled Drug Bioavailability, Drug Product Design and Performance, Smolen and Ball (eds.), Wiley, N.Y. (1984); Ranger and Peppas, 1983, *J., Macromol. Sci. Rev. Macromol. Chem.* 23:61; See also Levy et al., 1985, *Science* 228:190; During et al., 1989, Ann. Neurol. 25:351; Howard et al., 1989, *J. Neurosurg.* 7 1:105); U.S. Pat. No. 5,679,377; 5,916,597; 5,912,015; 5,989,463; 5,128,326; PCT Publication No. WO 99/15154; and PCT Publication No. WO 99/20253). Examples of polymers used in sustained release formulations include, but are not limited to, poly(2-hydroxy ethyl methacrylate), poly(methyl methacrylate), poly(acrylic acid), poly(ethylene-co-vinyl acetate), poly(methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters. In yet another embodiment, a controlled release system can be placed in proximity of the therapeutic target thus requiring only a fraction of the systemic dose (see, e.g., Goodson, in Medical Applications of Controlled Release, supra, vol. 2, pp. 115-138 (1984)). In another embodiment, polymeric compositions useful as controlled release implants are used according to Dunn et al. (See U.S. Pat. No. 5,945,155). This particular method is based upon the therapeutic effect of the in situ controlled release of the bioactive material from the polymer system. The implantation can generally occur anywhere within the body of the patient in need of therapeutic treatment. In another embodiment, a non-polymeric sustained delivery system is used, whereby a non-polymeric implant in the body of the subject is used as a drug delivery system. Upon implantation in the body, the organic solvent of the implant will dissipate, disperse, or leach from the composition into surrounding tissue fluid, and the non-polymeric material will gradually coagulate or precipitate to form a solid, microporous matrix (See U.S. Pat. No. 5,888,533).

Controlled release systems are discussed in the review by Langer (1990, *Science* 249:1527-1533). Any technique known to one of skill in the art can be used to produce sustained release formulations comprising one or more therapeutic agents of the invention. See, e.g., U.S. Pat. No. 4,526,938; International Publication Nos. WO 91/05548 and WO 96/20698; Ning et al., 1996, *Radiotherapy & Oncology* 39:179-189; Song et al., 1995, *PDA Journal of Pharmaceutical Science & Technology* 50:372-397; Cleek et al., 1997, *Pro. Int'l. Symp. Control. Rel. Bioact. Mater.* 24:853-854; and Lam et al., 1997, *Proc. Int'l. Symp. Control Rel. Bioact. Mater.* 24:759-760, each of which is incorporated herein by reference in its entirety.

In a specific embodiment where the composition of the invention is a nucleic acid encoding an antibody, the nucleic acid can be administered in vivo to promote expression of its encoded antibody, by constructing it as part of an appropriate nucleic acid expression vector and administering it so that it becomes intracellular, e.g., by use of a retroviral vector (See U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (See e.g., Joliot et al., 1991, *Proc. Natl. Acad. Sci. USA* 88:1864-1868), etc. Alternatively, a nucleic acid can be introduced intracellularly and incorporated within host cell DNA for expression by homologous recombination.

For antibodies, the therapeutically or prophylactically effective dosage administered to a subject is typically 0.1 mg/kg to 200 mg/kg of the subject's body weight. Preferably, the dosage administered to a subject is between 0.1 mg/kg and 20 mg/kg of the subject's body weight and more preferably the dosage administered to a subject is between 1 mg/kg to 10 mg/kg of the subject's body weight, most preferably between 5 mg/kg to 25 mg/kg of the subject's body weight. The dosage and frequency of administration of antibodies of the invention may be reduced also by enhancing uptake and tissue penetration of the antibodies or fusion proteins by modifications such as, for example, lipidation.

Treatment of a subject with a therapeutically or prophylactically effective amount of antibodies of the invention can include a single treatment or, preferably, can include a series of treatments. In a preferred example, a subject is treated with antibodies of the invention in the range of between about 0.1 to 30 mg/kg body weight, one time per week for between about 1 to 10 weeks, preferably between 2 to 8 weeks, more preferably between about 3 to 7 weeks, and even more preferably for about 4, 5, or 6 weeks. In other embodiments, the pharmaceutical compositions of the invention are administered once a day, twice a day, or three times a day. In specific preferred embodiments, a subject is treated with antibodies of the invention in the range of between about 5 to 25 mg/kg body weight for 7 days. In other embodiments, the pharmaceutical compositions are administered once a week, twice a week, once every two weeks, once a month, once every six weeks, once every two months, twice a year or once per year. It will also be appreciated that the effective dosage of the antibodies used for treatment may increase or decrease over the course of a particular treatment.

5.6.1 Pharmaceutical Compositions

The compositions of the invention include bulk drug compositions useful in the manufacture of pharmaceutical compositions (e.g., impure or non-sterile compositions) and pharmaceutical compositions (i.e., compositions that are suitable for administration to a subject or patient) which can be used in the preparation of unit dosage forms. Such compositions comprise a prophylactically or therapeutically effective amount of a prophylactic and/or therapeutic agent disclosed herein or a combination of those agents and a pharmaceutically acceptable carrier. Preferably, compositions of the invention comprise a prophylactically or therapeutically effective amount of antibodies of the invention and a pharmaceutically acceptable carrier.

In one particular embodiment, the pharmaceutical composition comprises of a therapeutically effective amount of an antibody or a fragment thereof that binds one or more flaviviral antigens, particularly WNV antigens, and a pharmaceutically acceptable carrier. In another embodiment, said pharmaceutical composition further comprises one or more additional prophylactic or therapeutic agents.

In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant (e.g., Freund's adjuvant (complete and incomplete), excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like.

Generally, the ingredients of compositions of the invention are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compositions of the invention can be formulated as neutral or salt forms. Pharmaceutically acceptable salts include, but are not limited to those formed with anions such as those derived from hydrochloric, phosphoric, acetic, oxalic, tartaric acids, etc., and those formed with captions such as those derived from sodium, potassium, ammonium, calcium, ferric hydroxides, isopropylamine, triethylamine, 2-ethylamino ethanol, histidine, procaine, etc.

5.7 Antibody Characterization and Demonstration of Therapeutic or Prophylactic Utility Antibodies of the present invention or fragments thereof may be characterized in a variety of ways. In particular, antibodies of the invention or fragments thereof may be assayed for the ability to immunospecifically bind to a WNV antigen. Such an assay may be performed in solution (e.g., Houghten, 1992, Bio/Techniques 13:412-421), on beads (Lam, 1991, Nature 354:82-84), on chips (Fodor, 1993, Nature 364:555-556), on bacteria (U.S. Pat. No. 5,223,409), on spores (U.S. Pat. Nos. 5,571,698; 5,403,484; and 5,223,409), on plasmids (Cull et al., 1992, Proc. Natl. Acad. Sci. USA 89:1865-1869) or on phage (Scott and Smith, 1990, Science 249:386-390; Devlin, 1990, Science 249:404-406; Cwirla et al., 1990, Proc. Natl. Acad. Sci. USA 87:6378-6382; and Felici, 1991, J. Mol. Biol. 222:301-310) (each of these references is incorporated herein by reference in its entirety). Antibodies or fragments thereof that have been identified to immunospecifically bind to a flaviviral antigen or a fragment thereof can then be assayed for their specificity and affinity for a flaviviral antigen.

The antibodies of the invention or fragments thereof may be assayed for immunospecific binding to a flaviviral antigen, particularly WNV antigen, and cross-reactivity with other antigens by any method known in the art. Immunoassays which can be used to analyze immunospecific binding and cross-reactivity include, but are not limited to, competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see, e.g., Ausubel et al, eds, 1994, Current Protocols in Molecular Biology, Vol. 1, John Wiley & Sons, Inc., New York, which is incorporated by reference herein in its entirety). Exemplary immunoassays are described briefly below (but are not intended by way of limitation).

Immunoprecipitation protocols generally comprise lysing a population of cells in a lysis buffer such as RIPA buffer (1% NP-40 or Triton X-100, 1% sodium deoxycholate, 0.1% SDS, 0.15 M NaCl, 0.01 M sodium phosphate at pH 7.2, 1% Trasylol) supplemented with protein phosphatase and/or protease inhibitors (e.g., EDTA, PMSF, aprotinin, sodium vanadate), adding the antibody of interest to the cell lysate, incubating for a period of time (e.g, 1 to 4 hours) at 40° C., adding protein A and/or protein G sepharose beads to the cell lysate, incubating for about an hour or more at 40° C., washing the beads in lysis buffer and resuspending the beads in SDS/sample buffer. The ability of the antibody of interest to immunoprecipitate a particular antigen can be assessed by, e.g., western blot analysis. One of skill in the art would be knowledgeable as to the parameters that can be modified to increase the binding of the antibody to an antigen and decrease the background (e.g., pre-clearing the cell lysate with sepharose beads). For further discussion regarding immunoprecipitation protocols see, e.g., Ausubel et al, eds, 1994, Current Protocols in Molecular Biology, Vol. 1, John Wiley & Sons, Inc., New York at 10.16.1.

Western blot analysis generally comprises preparing protein samples, electrophoresis of the protein samples in a polyacrylamide gel (e.g., 8%-20% SDS-PAGE depending on the molecular weight of the antigen), transferring the protein sample from the polyacrylamide gel to a membrane such as nitrocellulose, PVDF or nylon, blocking the membrane in blocking solution (e.g., PBS with 3% BSA or non-fat milk), washing the membrane in washing buffer (e.g., PBS-Tween 20), blocking the membrane with primary antibody (the antibody of interest) diluted in blocking buffer, washing the membrane in washing buffer, blocking the membrane with a secondary antibody (which recognizes the primary antibody, e.g., an anti-human antibody) conjugated to an enzymatic substrate (e.g., horseradish peroxidase or alkaline phosphatase) or radioactive molecule (e.g., $^{32}$P or $^{125}$I) diluted in blocking buffer, washing the membrane in wash buffer, and detecting the presence of the antigen. One of skill in the art would be knowledgeable as to the parameters that can be modified to increase the signal detected and to reduce the background noise. For further discussion regarding western blot protocols see, e.g., Ausubel et al, eds, 1994, Current Protocols in Molecular Biology, Vol. 1, John Wiley & Sons, Inc., New York at 10.8.1.

ELISAs comprise preparing antigen, coating the well of a 96 well microtiter plate with the antigen, adding the antibody of interest conjugated to a detectable compound such as an enzymatic substrate (e.g., horseradish peroxidase or alkaline phosphatase) to the well and incubating for a period of time, and detecting the presence of the antigen. In ELISAs, the antibody of interest does not have to be conjugated to a detectable compound; instead, a second antibody (which recognizes the antibody of interest) conjugated to a detectable compound may be added to the well. Further, instead of coating the well with the antigen, the antibody may be coated to the well. In this case, a second antibody conjugated to a detectable compound may be added following the addition of the antigen of interest to the coated well. One of skill in the art would be knowledgeable as to the parameters that can be modified to increase the signal detected as well as other variations of ELISAs known in the art. For further discussion regarding ELISAs see, e.g., Ausubel et al, eds, 1994, Current Protocols in Molecular Biology, Vol. 1, John Wiley & Sons, Inc., New York at 11.2.1.

The binding affinity of an antibody to an antigen and the off-rate of an antibody-antigen interaction can be determined by competitive binding assays. One example of a competitive binding assay is a radioimmunoassay comprising the incubation of labeled antigen (e.g., $^3$H or $^{125}$I) with the antibody of interest in the presence of increasing amounts of unlabeled antigen, and the detection of the antibody bound to the labeled antigen. The affinity of the antibody of the present invention or a fragment thereof for a WNV antigen and the binding off-rates can be determined from the data by scatchard plot analysis. Competition with a second antibody can also be determined using radioimmunoassays. In this case, a WNV antigen is incubated with an antibody of the present invention or a fragment thereof conjugated to a labeled compound (e.g., $^3$H or $^{125}$I) in the presence of increasing amounts of an unlabeled second antibody.

In a preferred embodiment, BIAcore kinetic analysis is used to determine the binding on and off rates of antibodies or fragments thereof to a WNV antigen. BIAcore kinetic analysis comprises analyzing the binding and dissociation of a WNV antigen from chips with immobilized antibodies or fragments thereof on their surface.

The antibodies of the invention or fragments thereof can also be assayed for their ability to inhibit the binding of a flaviviral antigen to its host cell receptor using techniques known to those of skill in the art and exemplified herein. For example, cells expressing the receptor for WNV can be contacted with WNV in the presence or absence of an antibody or fragment thereof and the ability of the antibody or fragment thereof to inhibit WNV's binding can measured by, for example, flow cytometry or a scintillation assay. WNV (e.g., WNV antigen such as E protein) or the antibody or antibody fragment can be labeled with a detectable compound such as a radioactive label (e.g., 32P, 35S, and 125I) or a fluorescent label (e.g., fluorescein isothiocyanate, rhodamine, phycoerythrin, phycocyanin, allophycocyanin, o-phthaldehyde and fluorescamine) to enable detection of an interaction between WNV and its host cell receptor. Alternatively, the ability of antibodies or fragments thereof to inhibit WNV from binding to its receptor can be determined in cell-free assays. For example, WNV or a WNV antigen can be contacted with an antibody or fragment thereof and the ability of the antibody or antibody fragment to inhibit WNV or the WNV antigen from binding to its host cell receptor can be determined. Preferably, the antibody or the antibody fragment is immobilized on a solid support and WNV or a WNV antigen is labeled with a detectable compound. Alternatively, WNV or a WNV antigen is immobilized on a solid support and the antibody or fragment thereof is labeled with a detectable compound. WNV or a WNV antigen may be partially or completely purified (e.g., partially or completely free of other polypeptides) or part of a cell lysate. Further, an WNV antigen may be a fusion protein comprising the WNV antigen and a domain such as glutathionine-S-transferase. Alternatively, an WNV antigen can be biotinylated using techniques well known to those of skill in the art (e.g., biotinylation kit, Pierce Chemicals; Rockford, Ill.).

The antibodies of the invention or fragments thereof are preferably tested in vitro, and then in vivo for the desired therapeutic or prophylactic activity, prior to use in humans. For example, in vitro assays which can be used to determine whether administration of a specific antibody or composition of the present invention is indicated, include in vitro cell culture assays in which a subject tissue sample is grown in culture, and exposed to or otherwise administered an antibody or composition of the present invention, and the effect of such an antibody or composition of the present invention upon the tissue sample is observed. In various specific embodiments, in vitro assays can be carried out with representative cells of cell types involved in a WNV infection to determine if an antibody or composition of the present invention has a desired effect upon such cell types. Preferably, the antibodies or compositions of the invention are also tested in in vitro assays and animal model systems prior to administration to humans. In a specific embodiment, mice are administered an antibody the invention or fragment thereof, or a composition of the invention, challenged with 100 to 1000 pfu of WNV, and four or more days later the mice are sacrificed and WNV titer and anti-WNV antibody serum titer is determined.

In accordance with the invention, clinical trials with human subjects need not be performed in order to demonstrate the prophylactic and/or therapeutic efficacy of antibodies of the invention or fragments thereof. In vitro and animal model studies using the antibodies or fragments thereof can be extrapolated to humans and are sufficient for demonstrating the prophylactic and/or therapeutic utility of said antibodies or antibody fragments.

Antibodies or compositions of the present invention for use in therapy can be tested for their toxicity in suitable animal model systems, including, but not limited to, rats, mice, cows, monkeys, and rabbits. For in vivo testing of an antibody or composition's toxicity, any animal model system known in the art may be used.

Efficacy in treating or preventing viral infection may be demonstrated by detecting the ability of an antibody or composition of the invention to inhibit the replication of the virus, to inhibit transmission or prevent the virus from establishing itself in its host, to reduce the incidence of WNV nfection, or to prevent, ameliorate or alleviate one or more symptoms associated with WNV infection. The treatment is considered therapeutic if there is, for example, a reduction is viral load, amelioration of one or more symptoms, a reduction in the duration of a WNV infection, or a decrease in mortality and/or morbidity following administration of an antibody or composition of the invention. Further, the treatment is considered therapeutic if there is an increase in the immune response following the administration of one or more antibodies or fragments thereof which immunospecifically bind to one or more WNV antigens.

Antibodies or compositions of the invention can be tested in vitro and in vivo for the ability to induce the expression of cytokines such as IFN-α, IFN-β, IFN-γ, IL-2, IL-3, IL-4, IL-5, IL-6, IL-7, IL-8, IL-9, IL-10, IL-12 and IL-15. Techniques known to those of skill in the art can be used to measure the level of expression of cytokines. For example, the level of expression of cytokines can be measured by analyzing the level of RNA of cytokines by, for example, RT-PCR and Northern blot analysis, and by analyzing the level of cytokines by, for example, immunoprecipitation followed by western blot analysis and ELISA.

Antibodies or compositions of the invention can be tested in vitro and in vivo for their ability to modulate the biological activity of immune cells, preferably human immune cells (e.g., T-cells, B-cells, and Natural Killer cells). The ability of an antibody or composition of the invention to modulate the biological activity of immune cells can be assessed by detecting the expression of antigens, detecting the proliferation of immune cells, detecting the activation of signaling molecules, detecting the effector function of immune cells, or detecting the differentiation of immune cells. Techniques known to those of skill in the art can be used for measuring these activities. For example, cellular proliferation can be assayed by $^3$H-thymidine incorporation assays and trypan blue cell counts. Antigen expression can be assayed, for example, by immunoassays including, but are not limited to, competitive and non-competitive assay systems using techniques such as western blots, immunohistochemistry radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays and FACS analysis. The activation of signaling molecules can be assayed, for example, by kinase assays and electrophoretic shift assays (EMSAs).

Antibodies or compositions of the invention can also be tested for their ability to inhibit viral replication or reduce viral load in in vitro, ex vivo and in vivo assays. Antibodies or compositions of the invention can also be tested for their ability to decrease the time course of WNV infection. Antibodies or compositions of the invention can also be tested for their ability to increase the survival period of humans suffering from WNV infection by at least 25%, preferably at least 50%, at least 60%, at least 75%, at least 85%, at least 95%, or at least 99%. Further, antibodies or compositions of the invention can be tested for their ability reduce the hospitalization period of humans suffering from WNV infection by at least 60%, preferably at least 75%, at least 85%, at least 95%, or at least 99%. Techniques known to those of skill in the art can be used to analyze the function of the antibodies or compositions of the invention in vivo.

5.8 Diagnostic Uses of Antibodies

Labeled antibodies, fragments and derivatives and analogs thereof, which immunospecifically bind to a WNV antigen can be used for diagnostic purposes to detect, diagnose, or monitor a WNV infection. The invention provides for the detection of a WNV infection, comprising: (a) assaying the expression of a WNV antigen in cells or a tissue sample of a subject using one or more antibodies or fragments thereof that immunospecifically bind to the WNV antigen; and (b) comparing the level of the WNV antigen with a control level, e.g., levels in normal tissue samples not infected with WNV, whereby an increase in the assayed level of WNV antigen compared to the control level of the WNV antigen is indicative of a WNV infection.

The invention provides a diagnostic assay for diagnosing a WNV infection, comprising: (a) assaying for the level of a WINV antigen in cells or a tissue sample of an individual using one or more antibodies or fragments thereof that immunospecifically bind to a WNV antigen; and (b) comparing the level of the WNV antigen with a control level, e.g., levels in normal tissue samples not infected with WNV, whereby an increase in the assayed WNV antigen level compared to the control level of the WNV antigen is indicative of a WNV infection. A more definitive diagnosis of WNV infection may allow health professionals to employ preventative measures or aggressive treatment earlier thereby preventing the development or further progression of WINV infection.

Antibodies of the invention or fragments thereof can be used to assay WNV antigen levels in a biological sample using classical immunohistological methods as described herein or as known to those of skill in the art (e.g., see Jalkanen et al., 1985, J. Cell. Biol. 101:976-985; and Jalkanen et al., 1987, J. Cell. Biol. 105:3087-3096). Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase; radioisotopes, such as iodine ($^{125}$I, $^{121}$I), carbon ($^{14}$C), sulfur ($^{35}$S), tritium ($^3$H), indium ($^{121}$In), and technetium ($^{99}$Tc); luminescent labels, such as luminol; and fluorescent labels, such as fluorescein and rhodamine, and biotin.

One aspect of the invention is the detection and diagnosis of a WNV infection in a human. In one embodiment, diagnosis comprises: a) administering (for example, parenterally, subcutaneously, or intraperitoneally) to a subject an effective amount of a labeled antibody or fragment thereof that immunospecifically binds to a WNV antigen; b) waiting for a time interval following the administering for permitting the labeled antibody or fragment thereof to preferentially concentrate at sites in the subject where the WNV antigen is expressed (and for unbound labeled molecule to be cleared to background level); c) determining background level; and d) detecting the labeled antibody or fragment thereof in the subject, such that detection of labeled antibody or fragment thereof above the background level indicates that the subject has a WNV infection. Background level can be determined by various methods including, comparing the amount of labeled molecule detected to a standard value previously determined for a particular system.

It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of $^{99}$Tc. The labeled antibody or antibody fragment will then preferentially accumulate at the location of cells which contain the specific protein. In vivo tumor imaging is described in S. W. Burchiel et al., "Immunopharmacokinetics of Radiolabeled Antibodies and Their Fragments." (Chapter 13 in Tumor Imaging: The Radiochemical Detection of Cancer, S. W. Burchiel and B. A. Rhodes, eds., Masson Publishing Inc. (1982).

Depending on several variables, including the type of label used and the mode of administration, the time interval following the administration for permitting the labeled molecule to preferentially concentrate at sites in the subject and for unbound labeled molecule to be cleared to background level is 6 to 48 hours or 6 to 24 hours or 6 to 12 hours. In another embodiment the time interval following administration is 5 to 20 days or 5 to 10 days.

In one embodiment, monitoring of a WVNV infection is carried out by repeating the method for diagnosing the WNV infection, for example, one month after initial diagnosis, six months after initial diagnosis, one year after initial diagnosis, etc.

Presence of the labeled molecule can be detected in the subject using methods known in the art for in vivo scanning. These methods depend upon the type of label used. Skilled artisans will be able to determine the appropriate method for detecting a particular label. Methods and devices that may be used in the diagnostic methods of the invention include, but are not limited to, computed tomography (CT), whole body scan such as position emission tomography (PET), magnetic resonance imaging (MRI), and sonography.

In a specific embodiment, the molecule is labeled with a radioisotope and is detected in the patient using a radiation responsive surgical instrument (Thurston et al., U.S. Pat. No. 5,441,050). In another embodiment, the molecule is labeled with a fluorescent compound and is detected in the patient using a fluorescence responsive scanning instrument. In another embodiment, the molecule is labeled with a positron emitting metal and is detected in the patient using positron emission-tomography. In yet another embodiment, the molecule is labeled with a paramagnetic label and is detected in a patient using magnetic resonance imaging (MRI).

5.8. Kits

The invention also provides a kit comprising one or more containers filled with one or more of the ingredients of the compositions of the invention.

The present invention provides kits that can be used in the above methods. In one embodiment, a kit comprises an antibody of the invention, preferably a purified antibody, in one or more containers. In an alterative embodiment, a kit comprises an antibody fragment that immunospecifically binds to a WNV antigen. In a specific embodiment, the kits of the present invention contain a substantially isolated WNV antigen as a control. Preferably, the kits of the present invention further comprise a control antibody which does not react with the WNV antigen. In another specific embodiment, the kits of the present invention contain a means for detecting the binding of an antibody to a WNV antigen (e.g., the antibody may be conjugated to a detectable substrate such as a fluorescent compound, an enzymatic substrate, a radioactive compound or a luminescent compound, or a second antibody which recognizes the first antibody may be conjugated to a detectable substrate). In specific embodiments, the kit may include a recombinantly produced or chemically synthesized WNV antigen. The WNV antigen provided in the kit may also be attached to a solid support. In a more specific embodiment the detecting means of the above-described kit includes a solid support to which WNV antigen is attached. Such a kit may also include a non-attached reporter-labeled anti-human antibody. In this embodiment, binding of the antibody to the WNV antigen can be detected by binding of the said reporter-labeled antibody.

In an additional embodiment, the invention includes a diagnostic kit for use in screening serum containing WNV antigens. The diagnostic kit includes a substantially isolated antibody specifically immunoreactive with a WNV antigen, and means for detecting the binding of the WNV antigen to the antibody. In one embodiment, the antibody is attached to a solid support. In a specific embodiment, the antibody may be a monoclonal antibody. The detecting means of the kit may include a second, labeled monoclonal antibody. Alternatively, or in addition, the detecting means may include a labeled, competing antigen.

In one diagnostic configuration, test serum is reacted with a solid phase reagent having a surface-bound WNV antigen obtained by the methods of the present invention. After the WNV antigen binds to a specific antibody, the unbound serum components are removed by washing, reporter-labeled anti-human antibody is added, unbound anti-human antibody is removed by washing, and a reagent is reacted with reporter-labeled anti-human antibody to bind reporter to the reagent in proportion to the amount of bound anti-WNV antigen antibody on the solid support. Typically, the reporter is an enzyme which is detected by incubating the solid phase in the presence of a suitable fluorometric, luminescent or colorimetric substrate (Sigma, St. Louis, Mo.).

The solid surface reagent in the above assay is prepared by known techniques for attaching protein material to solid support material, such as polymeric beads, dip sticks, 96-well plate or filter material. These attachment methods generally include non-specific adsorption of the protein to the support or covalent attachment of the protein, typically through a free amine group, to a chemically reactive group on the solid support, such as an activated carboxyl, hydroxyl, or aldehyde group. Alternatively, streptavidin coated plates can be used in conjunction with biotinylated antigen(s).

Thus, the invention provides an assay system or kit for carrying out this diagnostic method. The kit generally includes a support with surface-bound recombinant WNV antigen, and a reporter-labeled anti-human antibody for detecting surface-bound anti-WNV antigen antibody.

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

Various references are cited herein, including scientific publications, patent applications, and patents, the disclosures of which are incorporated by reference in their entireties.

6. EXAMPLES 6.1 Expression of Recombinant WNV E and NS1 Proteins.

An experimental plan was devised to express recombinant E and NS1 proteins from the 1999 New York strain of WNV (FIGS. 1A and B). The first 1290 nucleotides of WNV E protein and the complete gene (1056 nucleotides) of WNV NS1 were fused in-frame to their endogenous secretion signal sequences by PCR and cloned downstream of the polyhedrin promoter and upstream of a histidine repeat in a baculovirus shuttle vector (pFastBac). After expression, the truncated E protein lacks the C-terminal 71 amino acids that are associated with the membrane domain (Delenda et al., 1994, J Gen Virol 75:1569-78).

Recombinant baculoviruses that contain WNV E or NS1 genes were generated and used to infect insect SF9 or Hi-5 cells. SF9 supernatants were harvested and used to purify E or NS1 proteins by nickel-affinity chromatography, size exclusion and ion exchange (FIGS. 1A and B).

6.2 Generation of mAbs Against WNV Proteins.

BALB/c mice were immunized thrice at three-week intervals with purified WNV proteins using a carbohydrate and lipid-based adjuvant (RIBI). By measuring the polyclonal antibody response using a solid-phase E or NS1 protein-based ELISA, candidate immune mice were identified. Mice with a high-titer polyclonal (1/10,000) response were primed intravenously with purified E or NS1 proteins. Splenocytes were harvested and fused to the non-secreting P3X63Ag8.6.5.3 myeloma according to standard protocols (Harlow et al., 1988. Antibodies, A laboratory manual. Cold Spring Harbor Laboratory, Cold Spring Harbor). Approximately 1200 hybridomas were screened for binding to purified E or NS1 proteins and for immunoreactivity with WNV-infected BHK21 cells. From these studies, 34 antibodies against the WNV E protein and 21 antibodies against WNV NS1 (WNV NS1/1, IgG1k) were obtained.

The properties of a subset of these that have undergone further characterization (isotyping, mapping to domain III, neutralizing activity, complement-mediated lysis of infected cells) are shown in Tables 1A and 1B.

TABLE 1A

Summary of mAbs to WNV E protein

| number of hybridomas analyzed | positive for WNV infected cells | positive for E ectodomain on yeast cells | positive for domain III alone on yeast cells | moderate neutralization $PRNT_{50}$ 1 to 50 µg | strong neutralization $PRNT_{50} < 1$ µg | strong neutralizing and domain III positive |
|---|---|---|---|---|---|---|
| 1200 | 32 | 25 | 13 | 2 | 4 | 4 |
| 4G2 (anti-FV) | + | + | + | + | − | − |

TABLE 1B

Summary of neutralizing mAbs against WNV E protein

| Antibody | Isotype | Recognizes Infected Cells | Yeast Domain III only | Yeast Ectodomain E | Neutralizing | Ab-dep Complement Lysis of Cells | Ab-dependent complement neutralization |
|---|---|---|---|---|---|---|---|
| 4G2 | IgG2a | Yes | Yes | Yes | Weak | ND | ND |
| WNV E1 | IgG2a | Yes | Yes | Yes | Weak | Strong | Strong |
| WNV E5 | IgG2a | Yes | No | No | Weak | ND | ND |
| WNV E7 | IgG2b | Yes | Yes | Yes | Strong | ND | ND |
| WNV E8 | IgG1 | Yes | No | Yes | None | ND | No activity |
| WNV E16 | IgG2b | Yes | Yes | Yes | Strong | Strong | ND |
| WNV E24 | IgG2a | Yes | Yes | Yes | Strong | ND | ND |
| WNV E34 | IgG1 | Yes | Yes | Yes | Strong | ND | ND |

6.3 Domain Mapping of Antibodies:

An antibody mapping assay was developed using yeast surface display of the entire ectodomain of WNV E protein or just domain III alone. Expression of proteins on the outer surface of the yeast cell wall is a useful strategy for the construction of protein libraries and allowing for directed evolution of proteins (Gessner et al., 1998, Ann Hematol 76:231-48; Gollins et al., 1984, J. Gen. Virol. 65:1261-1272). In contrast to bacterial expression systems, complex extracellular eukaryotic proteins can be expressed on the yeast surface with efficient disulfide bonding and post-translational modification. Using this strategy, the ectodomain (E1-E415) or domain III (E296-E415) of the New York 1999 strain of WNV were cloned into the yeast display vector pYD1 (Invitrogen), expressed and preliminary antibody mapping studies were initiated (FIG. 13). Initial studies revealed high-level expression of both the E ectodomain and domain III on the surface of yeast within 24 hours of placement into selection media. Using this assay, 14 of the mAbs, including all of the strongly neutralizing mAbs, have been preliminarily mapped to sites within domain III.

Figure 14:
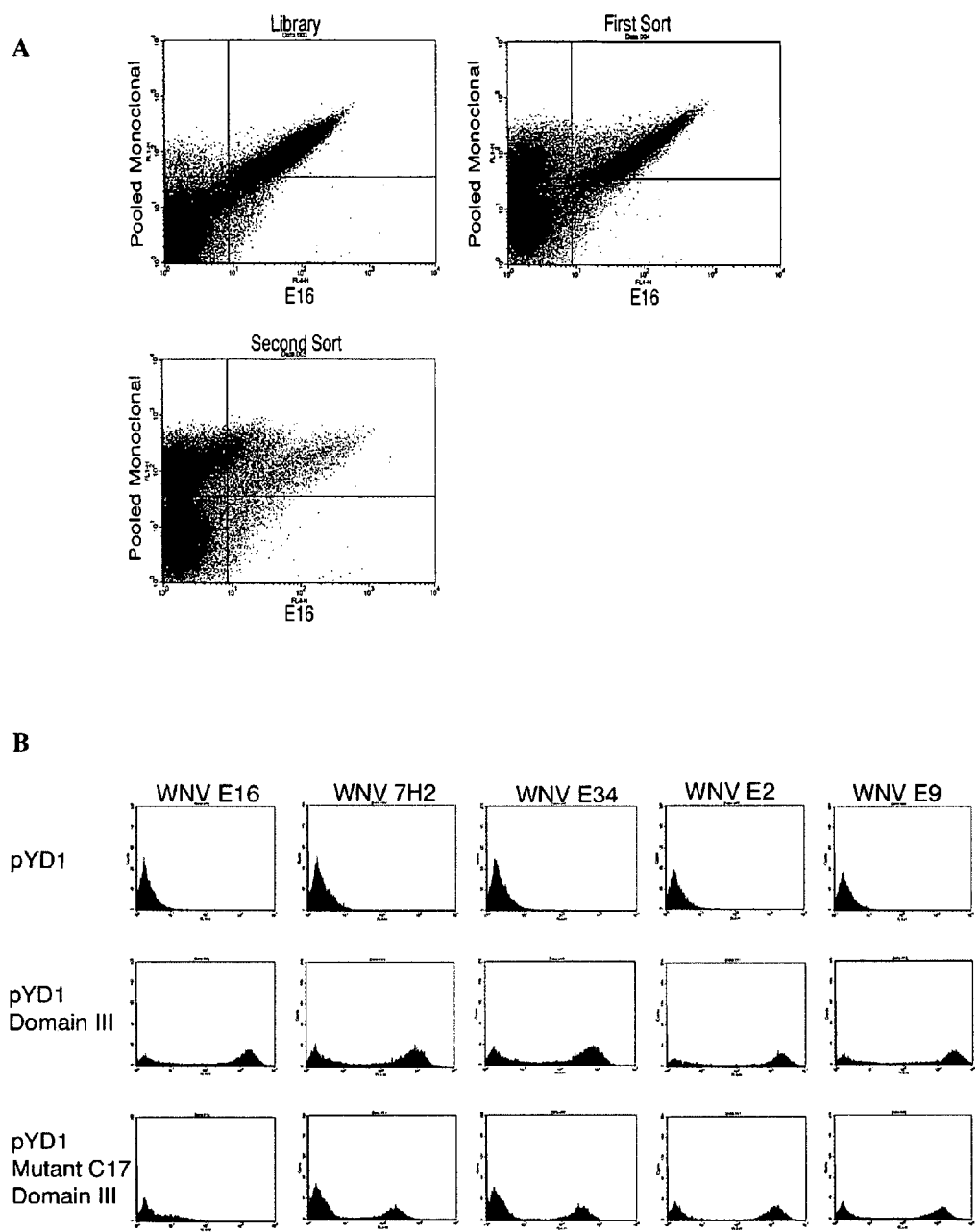
Figure 19:
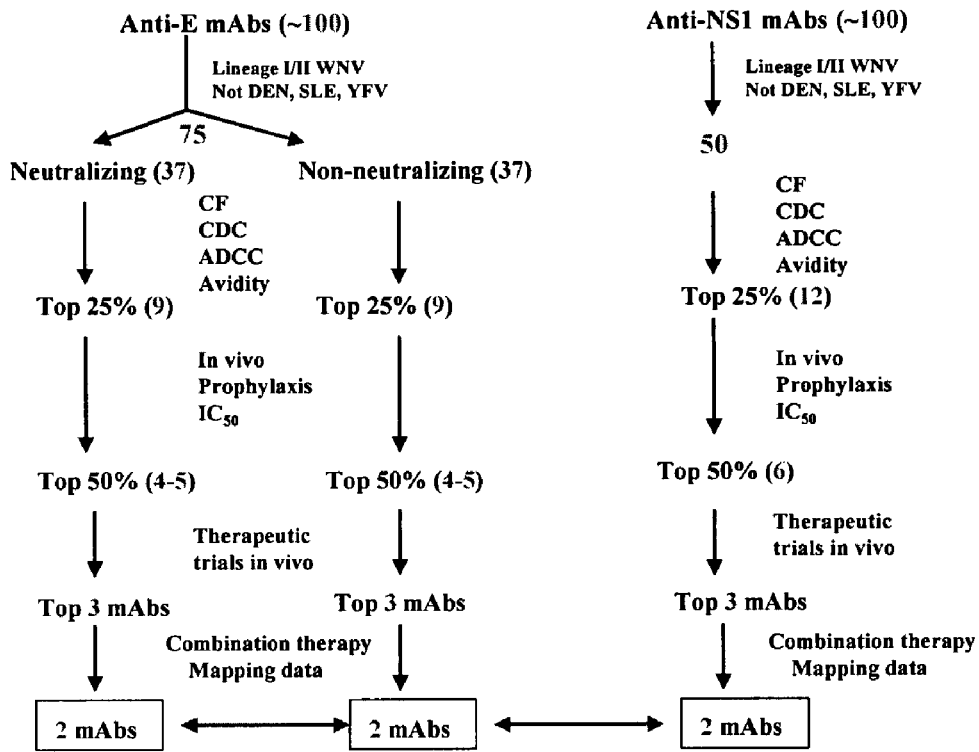

FIGS. 14A and B show yeast mapping of E16 contact residues as measured by flow cytometry. Serial flow cytometric sorts were performed with a mutagenized cDNA library of domain III. Prior to the fisrt sort <1% of the domain III positive yeast were WNV E16 negative. After the second sort >85% of the domain III positive yeast were recognized by a polyclonal antibody but not by WNV E16. Yeast mapping of E16 contact residues with clone 17 is shown in FIG. 14B. A single domain III expressing yeast clone was isolated that lacked binding to WNV E16 but retained binding to 14 other domain III antibodies. Binding profiles to WNV E16 and 4 other ecample antibodies are shown. This clone has a T332M mutation, thus one of the contact residues for WNV E16 is at position 332.

6.4 Neutralization of WNV Infection by Monoclonal Antibodies.

MAbs were evaluated for their relative ability to neutralize WNV infection using a plaque reduction neutralization titer (PRNT) assay in BHK21 cells. Serial dilutions of monoclonal antibodies were incubated with 100 PFU of WNV New York strain. After 1 hour, virus+antibody was added to BHK cells. After an agarose overlay was added, cells were incubated for three days, and plaques were stained with a crystal violet solution and scored visually. Of note, four mAbs (WNV E7, WNV E16, WNV E24, and WNV E34) strongly inhibited virus infection as reflected with plaque reduction neutralization titers ($PRNT_{50}$) values of approximately 1/10,000 (FIG. 15, and data not shown). A previous study had indicated that certain mAbs that neutralized lineage I WNV did not efficiently neutralize lineage II WNV strains (Beasley et al., 2001, Virology 279:447-58). To assess whether the newly isolated neutralizing mAbs had a broader specificity, we tested their ability to neutralize WN 956 D1173B (Peiris et al., 1981, Nature 289:189-191; Petersen et al., 2003, Jama 290:524-8), a lineage II WNV strain. WNV E7 and WNV E16 potently neutralization WNV strains from both lineages, with $PRNT_{50}$ values in the range of 0.1 μg/ml (0.7 nM).

6.5 Antibody-Dependent Complement Mediated Neutralization of Virions and Lysis of Infected Cells.

6.5.1 Neutralization.

Since complement fixation may augment neutralization and enhance protection in vivo, the ability of anti-WNV mAbs to fix complement and neutralize virus or lyse infected cells was investigated. To determine whether complement fixation directly neutralized WNV virions, an existing plaque-reduction assay was modified. Rabbit complement was pre-incubated with WNV virions in the presence or absence of mAbs against the WNV E prior to addition to a monolayer of hamster kidney (BHK21-15) epithelial cells. In the absence of antibodies, a dose-dependent reduction in viral plaques was observed; approximately 60% of infectious virus was neutralized after incubation with a 25% (v/v) solution of complement. In the presence of a 10% (v/v) solution of complement and a poorly neutralizing complement-fixing mAb (WNV E1, IgG2a) against the WNV E protein, infectivity of the virus was abolished completely (FIG. 16A). Control antibodies that either lacked binding to WNV (2E11, anti-ORF7a of SARS-COV) or the ability to efficiently fix complement (WNV E8, IgG1) demonstrated no additional complement-mediated neutralization.

6.5.2 Lysis of WNV-Infected Cells.

In addition to evaluating the degree by which complement directly neutralized WNV, we also assessed its capacity to trigger lysis of infected cells using a flow cytometric target cell assay (Harinasuta et al., 1985, Southeast Asian J Trop Med Public Health 16:332-6). Cells that are infected with WNV express E protein on their cell surface (data not shown), and thus, could be targets for classical, lectin, or alternate pathway activation of complement. MC57GL mouse fibroblasts were mock-infected or infected with WNV and incubated with rabbit complement in the presence or absence of complement-fixing mAbs against WNV. After two hours, cells were incubated with propidium iodide and the percentage of dead cells was determined by flow cytometry. In the absence of antibodies, no specific cell lysis of WNV-infected cells was observed (FIG. 16B) even at high (25% solution) concentrations of complement. In contrast, the addition of complement-fixing anti-WNV E mAbs (WNV E1 and WNV E16, IgG2a and IgG2b, respectively) resulted in the rapid killing of WNV-infected but not uninfected targets at low concentrations (5% solution) of complement. Importantly, addition of a complement-fixing antibody against an irrelevant viral antigen (2E11, ORF7a of SARS CoV) did not trigger lysis of infected cells.

6.6 Prophylaxis Studies of WNV Antibodies

The mAbs WNV E1 and WNV E2, from the initial fusion were evaluated for their ability to protect mice from lethal WNV infection. WNV E1 exhibited weak neutralizing activity and WNV E2 had no detectable neutralizing activity in vitro. To determine the inhibitory capacity of these mAbs in vivo, wild type (5 week-old) C57BL/6 mice were pre-treated with one mg of WNV E1, WNV E2, or WNV NS1 mAbs prior to infection and then inoculated with $10^2$ PFU of WNV. As a negative control, mice were also pre-treated with 1 mg of a mAb against DEN type 3 E protein. WNV E1 and NS1 showed 90% and 50% protection against infection (FIGS. 2A and B) whereas WNV E2 or the anti-DEN mAb provided no protection. These studies demonstrate some but not all individual mAbs against WNV can provide protection when administered prior to infection.

6.6.1 Dose Response Studies

Dose Response of protection of WNV E16 and E24 monoclonal antibodies are see in FIG. 20. 5 week pld C576BL/6 mice were infected with $10^2$ PFU of WNV. 48 hours later (hour), mice were inoculated with a single indicated does of monoclonal antibody or PBS and then followed for survival. N=20 for each mice condition.

6.7 Therapeutic Studies with WNV E16 MAB in sIgM-/- and Wild Type Mice.

It has been previously demonstrated that post-exposure therapy of mice with immune human γ-globulin that had neutralizing activity against WNV resulted in significant protection of mice against death (Diamond, 2003, Immunology and Cell Biology 81:196-206). In addition, mice that lacked the ability to secrete IgM (sIgM-/- mice) were completely susceptible (100% mortality rate after inoculation with 100 PFU of virus) to WNV infection, and that this was prevented by passive transfer of serum that contained neutralizing antibodies against WNV (Delenda et al., 1994, J Gen Virol 75:1569-78). Based on the PRNT assay, WNV E16 was the most potent neutralizing mAb in the panel: this mAb is ~1000 times more potent than the human γ-globulin preparation previously utilized. To evaluate the efficiency by which WNV E16 could treat an ongoing WNV infection, its ability to abort an infection in sIgM-/- mice was tested. When a single dose was administered 48 hours after the initial infection, WNV E16 protected all animals from death whereas those treated with a non-binding isotype control mAb (anti-SARS mAb) all succumbed to infection by day 12 (FIG. 17, left panel). In wild type mice, WNV E16 provided significant protection against lethality when administered either 2 or 4 days after infection (FIG. 17, right panel). The level of protection was superior to that observed in an identical model with the Israeli human immune γ-globulin.

Therapeutic studies of WNV E16 and E24 mAbs are shown in FIG. 21. 5 week old C57BL/6 mice were infected with $10^2$ PFU of WNV. At two or four days after infection, mice received a single dose of PBS, anti-SARS 7a (0.5 mg), anti WNV E16 or E24 (0.5 mg), or a combination of anti-WNV E16+E24 (0.25 mg of each). Subsequently, mice were followed for survival. N=20 mice for each condition. The bracket indicates significant (P<0.001) differences from the saline or negative mAb control.

6.8 Model of West Nile Encephalitis in Wild Type C57BL/6 Mice.

The WNV infection model in C57BL/6 mice parallels human disease. One week after subcutaneous inoculation, mice develop systemic and CNS infection with a subset progressing to paralysis and death. Similar to humans, infected mice develop high virus burdens in the CNS. Mice that succumb to infection show similar clinical signs several days prior to death including fur ruffling, weight loss, hunchback posture, and limb paralysis. The age of the animal and maturity of the immune response influences susceptibility to WNV infection. Younger mice had increased mortality after WNV infection: mice that were less than four weeks old uniformly succumbed to infection whereas those at 5 and 8 weeks old mice had mortality rate of 85 and 35%, respectively (data not shown).

Figure 4:
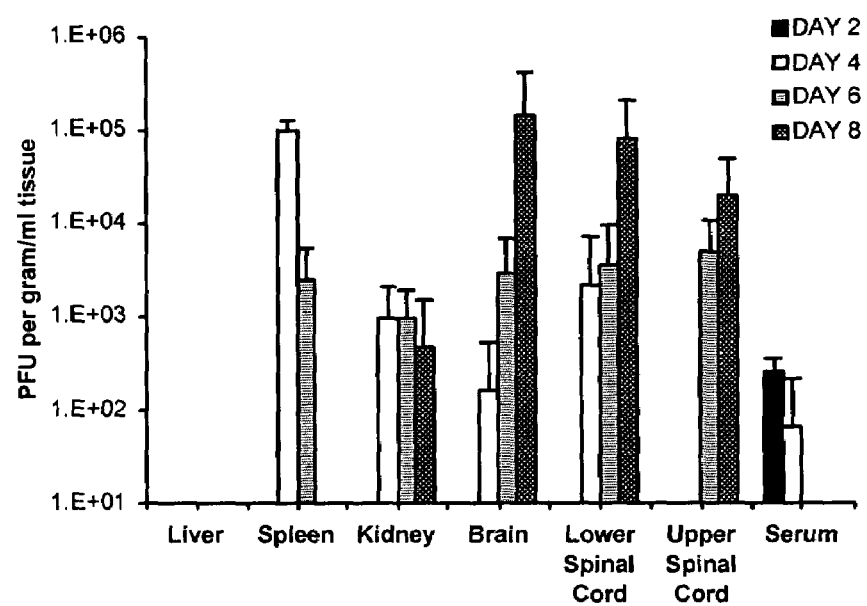

To elucidate the pathogenesis of WNV, the route that WNV takes after inoculation was characterized. Real-time fluorogenic RT-PCR and viral plaque assays on tissue homogenates were used to measure viral RNA and infectious virus. Experiments were initiated with a WNV that expresses a GFP marker protein (unpublished observations) to determine viral tropism in vivo. After footpad inoculation of wild type C57BL/6 mice, viral replication was observed first in the popliteal and inguinal lymph nodes. Within 2 to 4 days of infection, viral RNA and infectious virus were detected in the serum, spleen and kidney. By 6 days after infection, virus was found at several sites in the CNS including the brain, inferior and superior spinal cord. Later (day 8 and after), the overwhelming abundance of viral RNA was detected in the brain and spinal cord (FIG. 4).

6.9 West Nile Infection in Immunodeficient Mice 6.9.1 RAG1 Mice.

To understand how the immune system protects against WNV infection, congenic immunodeficient mice were infected, initial experiments were performed in RAG1 mice that lack both B and T cells. Even at the lowest dose ($10^2$ PFU) tested, 100% of adult RAG1 mice rapidly succumbed to infection (FIG. 5A). Virologic analysis revealed extremely high titers of WNV ($>10^8$ PFU/g of tissue) in the brains of infected animals (data not shown). Adoptive transfer of immune, but not naive splenocytes protected RAG1 mice against disseminated infection, morbidity and mortality. Interestingly, B cells ($4 \times 10^6$ cells, >95% purity), obtained from immune wild type mice that produced specific antibody against WNV, rescued some RAG1 from lethal WNV infection after adoptive transfer (data not shown).

6.9.2 B Cell-Deficient (μMT) Mice.

Figure 6:
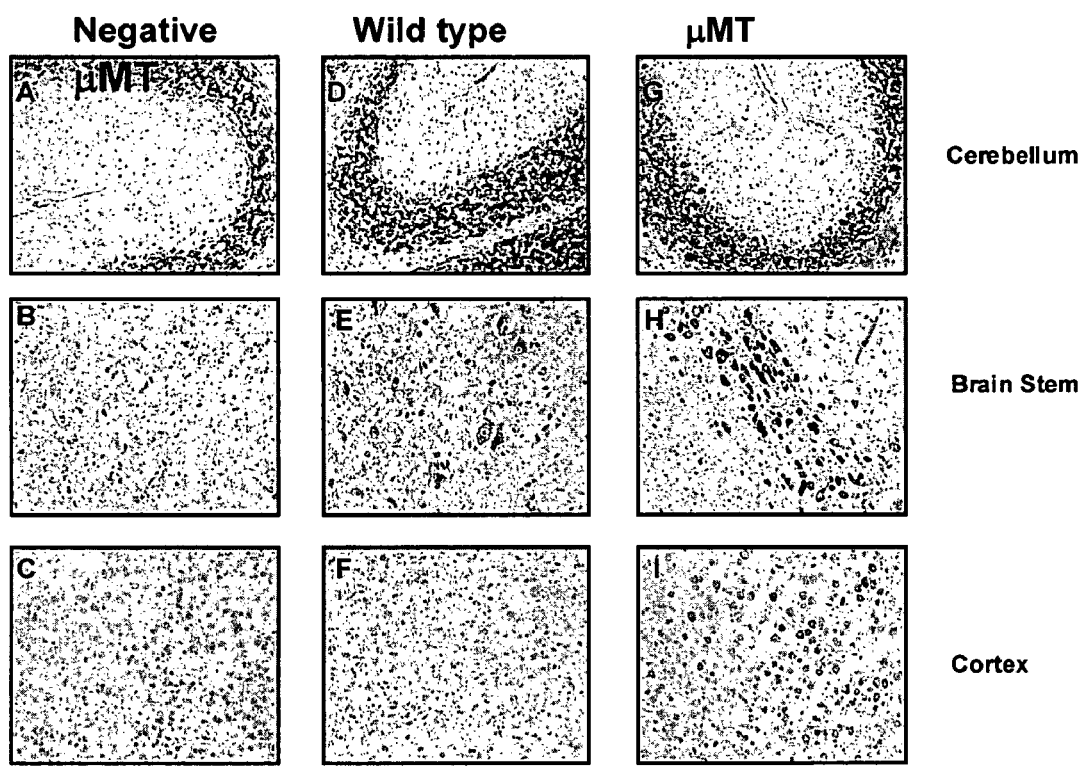

Because RAG1 mice were susceptible to infection, experiments were performed to determine the role of B cells in controlling WNV infection. C57BL/6 mice that lacked B cells (strain μMT) were vulnerable to lethal infection: all animals succumbed to infection at either $10^2$ PFU or $10^6$ PFU (FIG. 5B). The vulnerability to infection was reflected by 50% of the animals dying ($LD_{50}$) after inoculation with a dose of 1 PFU (data not shown). The levels of infectious virus and viral RNA were determined from serum, peripheral organs, and CNS tissue from μMT infected mice and compared to wild type mice (data not shown). Several observations were noted: (a) In wild type mice, viremia was detected at day 2 after subcutaneous infection but rapidly decreased to a level below detection by day 6. In μMT mice, a comparable level of infectious virus ($\sim 10^2$ PFU/ml) was measured at day 2 in serum but this was followed by a sustained increase in viremia through day 8 until levels exceeded $10^4$ PFU/ml. (b) In wild type mice, infectious virus levels peaked in the spleen at day 4 after infection, and disappeared by day 8. In contrast, in the spleens of μMT mice there was no clearance phase later in infection as virus ($10^4$ PFU/g) persisted in the spleen at days 8 and 9 after infection. (c) In the CNS of μMT mice, increased amounts of infectious virus were detected in the brain, lower spinal cord, and upper spinal cord after day 4 of infection: by day 8, there was 500-fold higher viral titers in the brain (FIG. 6) and greater than 100-fold levels in the spinal cord (and data not shown).

6.9.3 Viremia and Antibody Response.

When compared to wild type mice, the levels of viral RNA and infectious virus in the serum of μMT mice were roughly equivalent at 2 days after infection but ~500-fold higher at 4 days after infection. It was speculated that specific anti-WNV immunoglobulin played a critical role in preventing the dissemination of WNV. The kinetics of neutralizing antibody formation were examined by a viral plaque reduction assay using the method described above (FIG. 7A). As expected, no neutralizing antibodies were detected in μMT mice. In contrast, low levels (inhibitory titer of 1/10 to 1/40) of neutralizing antibodies were detected at day 4 after infection in wild type mice. After day 4, as the humoral response matured, inhibitory titers increased. Neutralizing antibodies were never detected in sera obtained from naive animals or from wild type animals within 2 days of the initial infection.

To distinguish whether IgM or IgG was responsible for neutralization, an ELISA was performed to characterize the isotype of specific antibody against WNV. Briefly, purfied E protein or viral lysates were adsorbed to plastic. After blocking of non-specific sites with BSA, Tween 20, and horse serum, serial dilutions of serum obtained from infected mice at various days after infection was added. Subsequently, after washing, HRP-conjugated goat anti-mouse IgG or IgM. After washing, TMB susbtrate was added and the signal was measured using a 96 well plate ELISA reader Specific IgM was detected as early as day 4 after infection whereas specific anti-WNV IgG was not detected until 8 days after infection (FIG. 7B). Chemical and immunologic depletion of IgM confirmed this. Treatment with 0.05 M β-mercaptoethanol (which destroys IgM but not IgG (Scott et al., 1970, Clin Exp Immunol 6:313-6)) or preclearing with anti-IgM-agarose completely abolished neutralizing activity of serum obtained at day 4 after infection but not at day 10 (data not shown). Thus, day 10 serum contained primarily IgG-specific antibodies against WNV but day 4 serum contained exclusively IgM-specific antibodies against WNV.

6.10 Serum Reconstitution Experiments.

To directly assess the protective nature of antibody, naïve mice were passively administered heat-inactivated serum (FIG. 8) collected from naïve or immune wild type mice, or from wild type mice that were infected with WNV for 4 days and produced neutralizing IgM but not IgG. Passive transfer of naïve serum to μMT mice had no significant effect on mortality or average survival time. In contrast, immune serum protected μMT mice against infection. Transfer of sera from wild type mice that were 4 days post-infection had an intermediate phenotype; although there with an increase in average survival time, all μMT mice ultimately succumbed to infection. In contrast, passive transfer of serum from wild type mice that were 4 days post-infection to naïve wild type mice resulted in complete protection from morbidity and mortality.

6.11 Prophylaxis Studies with Immune Human γ-Globulin and WNV.

To confirm that antibodies mediated this protection and explore the possibility for antibody therapy against WNV, we evaluated the efficacy of purified immune human γ-globulin against WNV infection in mice. Human γ-globulin with immunoreactivity against WNV was obtained from pooled donors in Israel. Over the past several years, a series of epidemics have occurred in Israel such that 10-20% of the population has antibodies against WNV (Shimoni et al., 2001, Emerg Infect Dis 7:759). Human γ-globulin lots that had significant in vitro immunoreactivity (ELISA titers of $1/900$ against WNV antigen) and neutralizing (PRNT$_{50}$ of $1/50$-$1/100$) potential were utilized. Non-immune human γ-globulin was obtained from a non-endemic region, and lacked neutralizing activity or immunoreactivity. In vivo studies with human γ-globulin were performed in 8 week-old wild type and μMT B cell-deficient C57BL/6J mice (FIG. 9). Administration of a single dose of 0.2 mg (10 mg/kg) or greater of immune γ-globulin completely protected wild type mice against infection with $10^2$ PFU of WNV (FIG. 9A). Doses of 0.02 mg (1 mg/kg) and 0.002 mg (0.1 mg/kg) were less effective. In contrast, administration of non-immune γ-globulin did not protect against WNV infection. Because sub-neutralizing concentrations of antibodies can facilitate enhanced WNV infection in myeloid cells (Cardosa et al., 1986, J Virol 57:952-9; Gollins et al., 1984, J. Gen. Virol. 65:1261-1272; Gollins et al., 1985, J Gen Virol 66:1969-1982), we investigated the effect of very low doses of immune γ-globulin on WNV infection in mice. Notably, pretreatment of wild type mice with the lowest dose (0.0002 mg or less) did not induce excess mortality. In general, passive transfer of immune γ-globulin to μMT mice provided significant yet lower levels of protection compared to wild type mice (FIG. 9B). Although doses greater than 0.2 mg increased average survival time of μMT mice after infection, only those that received 10 mg (500 mg/kg) survived beyond 30 days.

6.12 Post-Exposure Therapeutic Studies with γ-Globulin.

Figure 10:
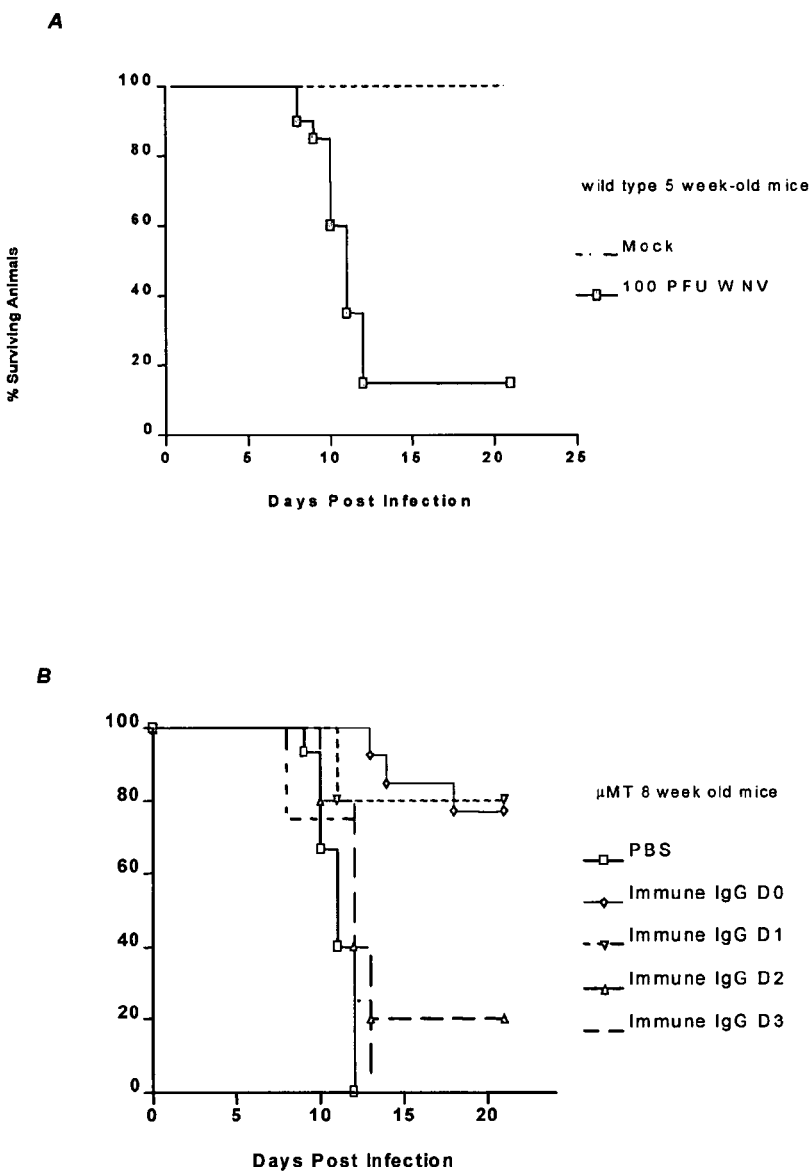

Because of the lack of specific treatment against WNV infection, the post-exposure therapeutic potential of immune γ-globulin was evaluated. Mice were inoculated with $10^2$ PFU of WNV at day 0 and then administered a single dose (15 mg; 750 mg/kg) of immune or non-immune γ-globulin at a particular day after infection and followed clinically. Initial studies were performed with the immunodeficient μMT mice. As expected, non-immune γ-globulin demonstrated no clinical improvement compared to the mice succumbed to infection (FIG. 10A). Immune γ-globulin, by contrast, had a modest therapeutic effect. μMT mice treated at day 1 or 2 after infection had an 80 and 20% survival rate. Treatment of μMT mice with immune γ-globulin after day 2 had no significant effect on survival (FIG. 10B).

Therapeutic trials with γ-globulin were conducted with 5 week-old wild type mice; because only 13% of these mice survived infection with WNV in the absence of therapy (FIG. 11A), the possibility for mortality benefit was greater. Treatment of 5 week-old mice with PBS or non-immune γ-globulin had no significant effect on average survival time or mortality (FIG. 11B). In contrast, treatment with immune γ-globulin 1, 2, 3, 4, or 5 days after infection increased the average survival time and decreased mortality rates (FIG. 11C and Table 3).

Because therapy with immune γ-globulin provided a beneficial effect even 5 days after initial infection, we hypothesized that antibody limited disease even after WNV had spread to the CNS. To confirm this, the levels of infectious virus were measured in the brain of 5 week-old mice after infection with $10^2$ PFU of WNV (FIG. 11D). When non-immune γ-globulin was administered, 33 and 100% of 5 week-old mice respectively developed measurable viral burdens in the brain at day 4 and 5 post-infection. In contrast, if mice were pre-treated with immune γ-globulin, no virus was detected in the brain at day 4 and 5 after infection. These data suggest that passive transfer of immune antibody improves clinical outcome even after WNV had disseminated into the CNS.

TABLE 3

Results of Therapeutic Trials with Human γ-globulin

| Human IgG treatment | Average Survival Time (P value) (days) | Survival (P value) (%) | Mice (n) |
|---|---|---|---|
| None | 12.1 ± 0.7 | 15.1 | 33 |
| Non-immune - D0 | 11.4 ± 0.7 (0.8) | 10.0 (0.7) | 20 |
| Immune - D0 | 19.3 ± 0.9 (0.0001**) | 83.3 (0.0001**) | 18 |
| Non-immune - D1 | 11.6 ± 0.8 (0.9) | 14.2 (0.7) | 19 |
| Immune- D1 | 19.6 ± 0.8 (0.0001**) | 84.2 (0.0001**) | 19 |
| Non-immune - D2 | 11.4 ± 1.0 (0.13) | 20.0 (0.5) | 20 |
| Immune- D2 | 18.8 ± 0.9 (0.0001**) | 73.7 (0.0001**) | 20 |
| Non-immune - D3 | 11.1 ± 0.8 (0.15) | 5.0 (0.06) | 20 |
| Immune- D3 | 17.2 ± 1.2 (0.008**) | 60.0 (0.002**) | 20 |
| Non-immune - D4 | 10.9 ± 0.7 (0.2) | 6.0 (0.2) | 18 |
| Immune- D4 | 15.1 ± 1.0 (0.01**) | 34.6 (0.02**) | 19 |
| Non-immune - D5 | 11.9 ± 0.9 (0.6) | 15.0 (0.7) | 20 |
| Immune- D5 | 15.5 + 1.3 (0.08) | 50.0 (0.04**) | 20 |

The endpoint of the study was 21 days after initial infection. For average survival times, P values were calculated using a two-tailed Mann-Whitney test. For survival analyses, P values were calculated using a log-rank test. P values were compared to the PBS saline control. Asterisks indicate statistical significance.

6.13 Experiments with C3-Deficient Mice.

A critical role for IgM in controlling infection was recently demonstrated (Diamond et al., 2003, J Exp Med. 198:1853-62). That IgM could protect by directly by neutralizing virus or by fixing complement and opsonizing virus was speculated. To assess the role of complement in WNV infection, mice that were deficient in C3 (C3 −/− in C57BL/6×129 F1 hybrid background (Kapadia et al., 2002, Immunity 17:1-20)) were infected with WNV. A deficiency of C3 caused 100% lethality with a survival curve that was similar to that of mice that lacked B cells and antibody (FIGS. 12A and B, compare A and B). Similar results have been observed with C4 −/− mice (E. Mehlhop and M. Diamond, unpublished observations). To determine whether antibodies to WNV that inhibit infection in vivo do so by a complement-dependent mechanism, prophylaxis studies were performed. Whereas 0.5 μl of immune serum provided complete protection of wild type mice, 50 μl of immune serum was required to prevent mortality in congenic C3 −/− mice. The presence of C3 in vivo augmented the inhibitory function of antibodies against WNV; thus, some of the antibody-mediated protection provided by serum appears to be mediated by a complement-dependent pathway.

6.14 NS1 Antibodies

NS1 antibodies were generated after immunizing mice with purified NS1 protein. After cloning by limiting dilution, antibodies were assayed for the ability to recognize lineage I and lineage II WNV strains, to detect NS1 on the surface of infected cells or by Western blot, to facilitate complement mediated lysis of WNV-infected cells, and for their efficacy at protecting mice from WNV infection.

TABLE 4

SUMMARY OF RESULTS

| Antibody | Isotype | WNV Lineage | Recognizes cellular NS1 | Western blot | Complement Lysis | In Vivo Protection |
|---|---|---|---|---|---|---|
| 1NS1 | G1 | I | + | + | ND | ND |
| 2NS1 | G1 | I | + | + | ND | ND |
| 3NS1 | G2b | I, II | + | + | ND | ND |
| 4NS1 | G1 | I, II | + | ND | None | None |
| 5NS1 | G1 | I, II | + | ND | ND | ND |
| 6NS1 | G1 | I | + | ND | No activity | ND |
| 7NS1 | G1 | I, II | + | ND | ND | ND |
| 8NS1 | G2a | I, II | + | ND | Weak | None |
| 9NS1 | G1 | I, II | + | ND | No activity | ND |
| 10NS1 | G2a | I, II | + | ND | Strong | Moderate |
| 11NS1 | G2b | I, II | + | ND | ND | ND |
| 12NS1 | G2a | I, II | + | ND | ND | ND |
| 13NS1 | G1 | I | + | ND | No activity | ND |
| 14NS1 | G2a | I, II | + | ND | ND | ND |
| 15NS1 | G2a | I, II | + | ND | ND | ND |
| 16NS1 | G2a | I, II | + | ND | ND | ND |
| 17NS1 | G2a | I, II | + | ND | Strong | Strong |
| 18NS1 | G2b | I | + | ND | ND | ND |
| 19NS1 | G1 | I | + | ND | No activity | ND |
| 21NS1 | G1 | I, II | + | ND | ND | ND |
| 22NS1 | G2a | I, II | + | ND | Strong | ND |
| 23NS1 | G1 | I | + | ND | ND | ND |

What is claimed is:

1. A monoclonal antibody or an antigen binding fragment thereof that specifically binds amino acids 306, 307, 330, and 332 of a West Nile virus E protein (WNE).

2. The monoclonal antibody of claim 1 which is produced by clone E16 having ATCC Accession No. PTA-6050.

3. The monoclonal antibody of claim 1 that competes for binding with a monoclonal antibody produced by clone E16, having ATCC Accession No. PTA-6050.

4. The monoclonal antibody of claim 1, wherein the antibody is human, humanized or chimeric.

5. The monoclonal antibody of claim 1 which is a humanized or chimeric version of the monoclonal antibody produced by clone E16 having ATCC Accession No. PTA-6050.

6. A hybridoma cell line E16, E24, or E34, having ATCC Accession No. PTA-6050, PTA-6051, or PTA-6052, respectively.

7. An isolated nucleic acid comprising a nucleotide sequence encoding a heavy chain or a light chain of the antibody or antigen binding fragment thereof of claim 1 operably linked to a heterologous promoter.

8. A vector comprising the nucleic acid molecule of claim 1.

9. A vector comprising a first nucleotide sequence encoding a heavy chain and a second nucleotide sequence encoding a light chain, said heavy chain and light chain being of the antibody or antigen binding fragment thereof of claim 1.

10. The vector of claim 9 which is an expression vector.

11. A host cell containing the vector of claim 9.

12. A host cell containing a first nucleic acid comprising a first nucleotide sequence operably linked to a heterologous promoter and a second nucleic acid comprising a second nucleotide sequence operably linked to the same or a different heterologous promoter, said first nucleotide sequence and second nucleotide sequence encoding a heavy chain and a light chain, respectively, of the antibody of claim 1, wherein said host cell expresses said antibody under appropriate conditions.

13. A method for recombinantly producing a West Nile virus specific monoclonal antibody, said method comprising: (i) culturing in a medium the host cell of claim 12, under conditions suitable for the expression of said antibody; and (ii) recovering said antibody from said medium.

14. A monoclonal antibody or an antigen binding fragment thereof that specifically binds a West Nile virus antigen, said antibody comprising a VH chain having the amino acid sequence of SEQ ID NO: 4, 8, or 12.

15. A monoclonal antibody or an antigen binding fragment thereof that specifically binds a West Nile virus antigen, said antibody comprising a VL chain having the amino acid sequence of SEQ ID NO: 2, 6, or 10.

16. A method of treating, preventing, or ameliorating the symptoms of a West Nile virus infection in a patient said method comprising administering to said patient a therapeutically effective amount of the monoclonal antibody of claim 1.

17. The method of claim 16, wherein the antibody is produced by clone E16, E24, or E34, having ATCC Accession No. PTA-6050, PTA-6051, or PTA-6052, respectively.

18. The method of claim 16, further comprising administering to said patient a therapeutically effective amount of a monoclonal antibody or antigen binding fragment thereof that specifically binds a West Nile virus antigen which is a non-structural protein.

19. The method of claim 16, further comprising administering to said patient an anti-viral agent.

20. The method of claim 19, wherein the anti-viral agent is selected from the group consisting of protease inhibitors, nucleoside reverse transcriptase inhibitors, non-nucleoside reverse transcriptase inhibitors, and nucleoside analogs.

21. The method of claim 19, wherein the anti-viral agent is selected from the group consisting of zidovudine, acyclovir, gangcyclovir, vidarabine, idoxuridine, trifluridine, ribavirin, foscarnet, amantadine, rimantadine, saquinavir, indinavir, amprenavir, lopinavir, ritonavir, alpha-interferon, adefovir, clevadine, entecavir, and pleconaril.

22. The method of claim 16, wherein said patient is human.

23. The method of claim 16, wherein the antibody is human, humanized or chimeric.

24. The method of claim 16, wherein the antibody is a humanized or chimeric version of the monoclonal antibody produced by clone E16, E24, or E34, having ATCC Accession No. PTA-6050, PTA-6051, or PTA-6052, respectively.

25. A method of diagnosis of a West Nile virus infection in a subject comprising:

(a) contacting a biological sample from said subject with an effective amount of the antibody or an antigen binding fragment thereof of claim 1; and (b) detecting binding of said antibody or antigen binding fragment thereof, wherein detection of binding of said antibody or antigen binding fragment thereof above a background or standard level indicates that said subject has an a West Nile virus infection.

26. A pharmaceutical composition comprising (i) a therapeutically effective amount of the antibody of claim 1; and (ii) a pharmaceutically acceptable carrier.

27. The pharmaceutical composition of claim 26, wherein the antibody is produced by clone E16, E24, or E34, having ATCC Accession No. PTA-6050, PTA-6051, or PTA-6052, respectively.

28. The pharmaceutical composition of claim 26, wherein the antibody is human, humanized or chimeric.

29. The pharmaceutical composition of claim 26, wherein said antibody is a humanized or chimeric version of the antibody produced by clone E16, E24, or E34, having ATCC Accession No. PTA-6050, PTA-6051, or PTA-6052, respectively.

30. The pharmaceutical composition of claim 26, further comprising a therapeutically effective amount of a monoclonal antibody that specifically binds a West Nile virus antigen which is a non-structural protein.

31. The antibody or an antigen binding fragment thereof of claim 1 that binds one to 12 additional amino acids of WNE selected from WNE residues 302-309, 330-333, 365-368, or 389-391.

32. A monoclonal antibody produced by clone E24 or E34, having ATCC Accession No. PTA-6051 or PTA-6052, respectively.

33. The monoclonal antibody of claim 32 which is a human, humanized, or chimeric version of the monoclonal antibody produced by clone E24 or E34, having ATCC Accession No. PTA-6051 or PTA-6052, respectively.

34. A pharmaceutical composition comprising (i) a therapeutically effective amount of the antibody of claim 32; and (ii) a pharmaceutically acceptable carrier.

35. A pharmaceutical composition comprising (i) a therapeutically effective amount of the antibody of claim 14; and (ii) a pharmaceutically acceptable carrier.

36. A pharmaceutical composition comprising (i) a therapeutically effective amount of the antibody of claim 15; and (ii) a pharmaceutically acceptable carrier.

37. A method of treating, preventing, or ameliorating the symptoms of a West Nile virus infection in a patient said method comprising administering to said patient a therapeutically effective amount of the monoclonal antibody of claim 32.

38. A method of treating, preventing, or ameliorating the symptoms of a West Nile virus infection in a patient said method comprising administering to said patient a therapeutically effective amount of the monoclonal antibody of claim 14.

39. A method of treating, preventing, or ameliorating the symptoms of a West Nile virus infection in a patient said method comprising administering to said patient a therapeutically effective amount of the monoclonal antibody of claim 15.

\* \* \* \* \*

```
                       SEQUENCE LISTING

<160> NUMBER OF SEQ ID NOS: 43

<210> SEQ ID NO 1
<211> LENGTH: 321
<212> TYPE: DNA
<213> ORGANISM: mouse
<220> FEATURE:
<223> OTHER INFORMATION: E16 VL

<400> SEQUENCE: 1
gacattgtga tgacccagtc tcacaaattc atgtccacat cagtaggaga cagggtcagc      60
atcacctgca aggccagtca ggatgtgagt actgctgtag cctggtatca acaaaaacca     120
gggcaatctc ctaaactact catttcctgg gcatccaccc ggcacactgg agtccctgat     180
cgcttcacag gcagtggatc tgggacagat tatactctca ccatcagcag tgtgcaggct     240
gaagacctgg cactttatta ctgtcagcaa cattatacca ctcccctcac gttcggtgct     300
gggaccaagc tggagctgaa a                                               321

<210> SEQ ID NO 2
<211> LENGTH: 107
<212> TYPE: PRT
<213> ORGANISM: mouse
<220> FEATURE:
<223> OTHER INFORMATION: E16 VL

<400> SEQUENCE: 2

Asp Ile Val Met Thr Gln Ser His Lys Phe Met Ser Thr Ser Val Gly
 1               5                  10                  15

Asp Arg Val Ser Ile Thr Cys Lys Ala Ser Gln Asp Val Ser Thr Ala
            20                  25                  30
```

Val Ala Trp Tyr Gln Gln Lys Pro Gly Gln Ser Pro Lys Leu Leu Ile
            35                  40                  45

Ser Trp Ala Ser Thr Arg His Thr Gly Val Pro Asp Arg Phe Thr Gly
        50                  55                  60

Ser Gly Ser Gly Thr Asp Tyr Thr Leu Thr Ile Ser Ser Val Gln Ala
65                  70                  75                  80

Glu Asp Leu Ala Leu Tyr Tyr Cys Gln Gln His Tyr Thr Thr Pro Leu
                85                  90                  95

Thr Phe Gly Ala Gly Thr Lys Leu Glu Leu Lys
            100                 105

<210> SEQ ID NO 3
<211> LENGTH: 357
<212> TYPE: DNA
<213> ORGANISM: mouse
<220> FEATURE:
<223> OTHER INFORMATION: E16 VH

<400> SEQUENCE: 3
caggttcagc tgcagcagtc tggatctgag ctgatgaagc ctggggcctc agtgcagata      60
tcctgcaagg ctactggcta cacattcagt gactactgga ttgagtgggt aaagcagagg     120
cctggacatg gccttgagtg gattggagat attttatgtg gaactggtag aactagatac     180
aatgagaagt taaaggccat ggccacattc actgcagata catcctccaa cacagccttc     240
atgcaactca gcagcctgac atctgaggac tctgccgtct attactgtgc aagatcggcg     300
tcatatggtg attacgctga ctactggggc catggcacca ctctcacagt ctcctca        357

<210> SEQ ID NO 4
<211> LENGTH: 119
<212> TYPE: PRT
<213> ORGANISM: mouse
<220> FEATURE:
<223> OTHER INFORMATION: E16 VH

<400> SEQUENCE: 4

Gln Val Gln Leu Gln Gln Ser Gly Ser Glu Leu Met Lys Pro Gly Ala
 1               5                  10                  15

Ser Val Gln Ile Ser Cys Lys Ala Thr Gly Tyr Thr Phe Ser Asp Tyr
            20                  25                  30

Trp Ile Glu Trp Val Lys Gln Arg Pro Gly His Gly Leu Glu Trp Ile
        35                  40                  45

Gly Asp Ile Leu Cys Gly Thr Gly Arg Thr Arg Tyr Asn Glu Lys Leu
    50                  55                  60

Lys Ala Met Ala Thr Phe Thr Ala Asp Thr Ser Ser Asn Thr Ala Phe
65                  70                  75                  80

Met Gln Leu Ser Ser Leu Thr Ser Glu Asp Ser Ala Val Tyr Tyr Cys
                85                  90                  95

Ala Arg Ser Ala Ser Tyr Gly Asp Tyr Ala Asp Tyr Trp Gly His Gly
            100                 105                 110

Thr Thr Leu Thr Val Ser Ser
        115

<210> SEQ ID NO 5
<211> LENGTH: 321
<212> TYPE: DNA
<213> ORGANISM: mouse
<220> FEATURE:
<223> OTHER INFORMATION: E24 VL

<400> SEQUENCE: 5

```
gacattgtga tgacccagtc tcacaaattc atgtccacat cagtaggaga cagggtcagt      60
atcacctgca aggccagtca ggatgtgagt actgctgtag cctggtatca acaaaaacca     120
gggcaatctc ctaaagtact gatttactgg gcatcaaccc ggcacactgg agtccctgat     180
cgcttcacag gcagtggatc tgggacagat tatactctta ccatcagcag tgtacaggct     240
gaagacctgg cactttatta ctgtcagcaa cattatagta atcctccgac gttcggtgga     300
ggcaccaagc tggaaatcaa a                                               321
```

<210> SEQ ID NO 6
<211> LENGTH: 107
<212> TYPE: PRT
<213> ORGANISM: mouse
<220> FEATURE:
<223> OTHER INFORMATION: E24 VL

<400> SEQUENCE: 6

```
Asp Ile Val Met Thr Gln Ser His Lys Phe Met Ser Thr Ser Val Gly
  1               5                  10                  15
Asp Arg Val Ser Ile Thr Cys Lys Ala Ser Gln Asp Val Ser Thr Ala
             20                  25                  30
Val Ala Trp Tyr Gln Gln Lys Pro Gly Gln Ser Pro Lys Val Leu Ile
         35                  40                  45
Tyr Trp Ala Ser Thr Arg His Thr Gly Val Pro Asp Arg Phe Thr Gly
     50                  55                  60
Ser Gly Ser Gly Thr Asp Tyr Thr Leu Thr Ile Ser Ser Val Gln Ala
 65                  70                  75                  80
Glu Asp Leu Ala Leu Tyr Tyr Cys Gln Gln His Tyr Ser Asn Pro Pro
                 85                  90                  95
Thr Phe Gly Gly Gly Thr Lys Leu Glu Ile Lys
            100                 105
```

<210> SEQ ID NO 7
<211> LENGTH: 357
<212> TYPE: DNA
<213> ORGANISM: mouse
<220> FEATURE:
<223> OTHER INFORMATION: E24 VH

<400> SEQUENCE: 7

```
caggttcagc tgcagcagtc tggacctgag ctggtgaagc ctggggcttt agtgaagata      60
tcctgcaagg cttctggtca caccttcaca agttacgata taaactgggt gaagcagagg     120
cctggacagg gacttgagtg gattggatgg atttatcctg agatggtag gattaagtac      180
aatgagaaat tcaagggcaa ggccatactg actgcagaca atcctccag cacagcctac      240
atgcagctca gcagcctgac ttctgagaac tctgcagtct atttctgtgc aagaggaggc     300
agctcgggca catactttga ctactggggc caaggcacca ctctcacagt ctcctca       357
```

<210> SEQ ID NO 8
<211> LENGTH: 119
<212> TYPE: PRT
<213> ORGANISM: mouse
<220> FEATURE:
<223> OTHER INFORMATION: E24 VH

<400> SEQUENCE: 8

```
Gln Val Gln Leu Gln Gln Ser Gly Pro Glu Leu Val Lys Pro Gly Ala
  1               5                  10                  15
```

-continued

```
                1               5              10              15
        Leu Val Lys Ile Ser Cys Lys Ala Ser Gly His Thr Phe Thr Ser Tyr
                       20                  25                  30

Asp Ile Asn Trp Val Lys Gln Arg Pro Gly Gln Gly Leu Glu Trp Ile
                       35                  40              45

Gly Trp Ile Tyr Pro Gly Asp Gly Arg Ile Lys Tyr Asn Glu Lys Phe
                       50                  55                  60

Lys Gly Lys Ala Ile Leu Thr Ala Asp Lys Ser Ser Ser Thr Ala Tyr
         65                 70                  75                  80

Met Gln Leu Ser Ser Leu Thr Ser Glu Asn Ser Ala Val Tyr Phe Cys
                           85                  90                  95

Ala Arg Gly Gly Ser Ser Gly Thr Tyr Phe Asp Tyr Trp Gly Gln Gly
                          100                 105                 110

Thr Thr Leu Thr Val Ser Ser
                          115
```

<210> SEQ ID NO 9
<211> LENGTH: 321
<212> TYPE: DNA
<213> ORGANISM: mouse
<220> FEATURE:
<223> OTHER INFORMATION: E34 VL

<400> SEQUENCE: 9

| gacattgtga | tgacccagtc | tcacaaattc | atgtccacat | cagtaggaga | cagggtcaac |  60 |
| atcacctgca | aggccagtca | ggatgtgagt | actgctgtag | cctggtatca | acaaaaacca | 120 |
| gggcaatctc | ctaaactact | gatttactgg | gcatccaccc | ggcacactgg | agtccctgat | 180 |
| cgcttcacag | gcagtggatc | ggggacacat | tatactctca | ccatcagcag | tgtgcaggct | 240 |
| gaagacctgg | cactttatta | ctgtcagcaa | cattatacca | ctcctctcac | gttcggtgct | 300 |
| gggaccaagc | tggagctgaa | a          |            |            |            | 321 |

<210> SEQ ID NO 10
<211> LENGTH: 107
<212> TYPE: PRT
<213> ORGANISM: mouse
<220> FEATURE:
<223> OTHER INFORMATION: E34 VL

<400> SEQUENCE: 10

```
        Asp Ile Val Met Thr Gln Ser His Lys Phe Met Ser Thr Ser Val Gly
         1               5                  10                  15

Asp Arg Val Asn Ile Thr Cys Lys Ala Ser Gln Asp Val Ser Thr Ala
                       20                  25                  30

Val Ala Trp Tyr Gln Gln Lys Pro Gly Gln Ser Pro Lys Leu Leu Ile
                       35                  40                  45

Tyr Trp Ala Ser Thr Arg His Thr Gly Val Pro Asp Arg Phe Thr Gly
                       50                  55                  60

Ser Gly Ser Gly Thr His Tyr Thr Leu Thr Ile Ser Ser Val Gln Ala
         65                 70                  75                  80

Glu Asp Leu Ala Leu Tyr Tyr Cys Gln Gln His Tyr Thr Thr Pro Leu
                           85                  90                  95

Thr Phe Gly Ala Gly Thr Lys Leu Glu Leu Lys
                          100                 105
```

<210> SEQ ID NO 11
<211> LENGTH: 357

```
<212> TYPE: DNA
<213> ORGANISM: mouse
<220> FEATURE:
<223> OTHER INFORMATION: E34 VH

<400> SEQUENCE: 11
caggttcagc tgcagcagtc tggacctgag ctggtgaagc ctgggacttt ggtgaagata      60
tcctgcaaga cttctggtta caccttcaca agctacgata taaactgggt gaagcagagg     120
cctggacagg gacttgagtg gattggatgg attttcctg gagatggtcg tattaagtac      180
aatgagcaaa tcaaggacaa ggccacactg actgcagaca atcctccag cacagcctac      240 atggagctca gcagcctgac ttctgagaac tccgcagtct atttctgtgc aagggcctcc     300
tactatggta gtatctttga ctactgggc caaggcacca ctctcacagt ctcctca         357

<210> SEQ ID NO 12
<211> LENGTH: 119
<212> TYPE: PRT
<213> ORGANISM: mouse
<220> FEATURE:
<223> OTHER INFORMATION: E34 VH

<400> SEQUENCE: 12

Gln Val Gln Leu Gln Gln Ser Gly Pro Glu Leu Val Lys Pro Gly Thr
 1               5                   10                  15

Leu Val Lys Ile Ser Cys Lys Thr Ser Gly Tyr Thr Phe Thr Ser Tyr
                20                  25                  30

Asp Ile Asn Trp Val Lys Gln Arg Pro Gly Gln Gly Leu Glu Trp Ile
            35                  40                  45

Gly Trp Ile Phe Pro Gly Asp Gly Arg Ile Lys Tyr Asn Glu Gln Ile
        50                  55                  60

Lys Asp Lys Ala Thr Leu Thr Ala Asp Lys Ser Ser Ser Thr Ala Tyr
 65                 70                  75                  80

Met Glu Leu Ser Ser Leu Thr Ser Glu Asn Ser Ala Val Tyr Phe Cys
                85                  90                  95

Ala Arg Ala Ser Tyr Tyr Gly Ser Ile Phe Asp Tyr Trp Gly Gln Gly
            100                 105                 110

Thr Thr Leu Thr Val Ser Ser
        115

<210> SEQ ID NO 13
<211> LENGTH: 30
<212> TYPE: PRT
<213> ORGANISM: Mouse
<220> FEATURE:
<223> OTHER INFORMATION: E16 VH FR1

<400> SEQUENCE: 13

Gln Val Gln Leu Gln Gln Ser Gly Ser Glu Leu Met Lys Pro Gly Ala
 1               5                   10                  15

Ser Val Gln Ile Ser Cys Lys Ala Thr Gly Tyr Thr Phe Ser
                20                  25                  30

<210> SEQ ID NO 14
<211> LENGTH: 30
<212> TYPE: PRT
<213> ORGANISM: Mouse
<220> FEATURE:
<223> OTHER INFORMATION: E24 VH FR1

<400> SEQUENCE: 14
```

Gln Val Gln Leu Gln Gln Ser Gly Pro Glu Leu Val Lys Pro Gly Ala
1               5                   10                  15

Leu Val Lys Ile Ser Cys Lys Ala Ser Gly His Thr Phe Thr
                20                  25                  30

<210> SEQ ID NO 15
<211> LENGTH: 30
<212> TYPE: PRT
<213> ORGANISM: Mouse
<220> FEATURE:
<223> OTHER INFORMATION: E34 VH FR1

<400> SEQUENCE: 15

Gln Val Gln Leu Gln Gln Ser Gly Pro Glu Leu Val Lys Pro Gly Thr
1               5                   10                  15

Leu Val Lys Ile Ser Cys Lys Thr Ser Gly Tyr Thr Phe Thr
                20                  25                  30

<210> SEQ ID NO 16
<211> LENGTH: 5
<212> TYPE: PRT
<213> ORGANISM: Mouse
<220> FEATURE:
<223> OTHER INFORMATION: E16 CDR H1

<400> SEQUENCE: 16

Asp Tyr Trp Ile Glu
1               5

<210> SEQ ID NO 17
<211> LENGTH: 5
<212> TYPE: PRT
<213> ORGANISM: Mouse
<220> FEATURE:
<223> OTHER INFORMATION: CDR H1 of E24 and E34

<400> SEQUENCE: 17

Ser Tyr Asp Ile Asn
1               5

<210> SEQ ID NO 18
<211> LENGTH: 14
<212> TYPE: PRT
<213> ORGANISM: Mouse
<220> FEATURE:
<223> OTHER INFORMATION: E16 FR2

<400> SEQUENCE: 18

Trp Val Lys Gln Arg Pro Gly His Gly Leu Glu Trp Ile Gly
1               5                   10

<210> SEQ ID NO 19
<211> LENGTH: 14
<212> TYPE: PRT
<213> ORGANISM: Mouse
<220> FEATURE:
<223> OTHER INFORMATION: E24 and E34 FR2

<400> SEQUENCE: 19

Trp Val Lys Gln Arg Pro Gly Gln Gly Leu Glu Trp Ile Gly
1               5                   10

<210> SEQ ID NO 20
<211> LENGTH: 15
<212> TYPE: PRT
<213> ORGANISM: Mouse

```
<220> FEATURE:
<223> OTHER INFORMATION: E16 CDR H2

<400> SEQUENCE: 20

Asp Ile Leu Cys Gly Thr Gly Arg Thr Arg Tyr Asn Glu Lys Leu
1               5                   10                  15

<210> SEQ ID NO 21
<211> LENGTH: 17
<212> TYPE: PRT
<213> ORGANISM: Mouse
<220> FEATURE:
<223> OTHER INFORMATION: E24 CDR H2

<400> SEQUENCE: 21

Trp Ile Tyr Pro Gly Asp Gly Arg Ile Lys Tyr Asn Glu Lys Phe Lys
1               5                   10                  15

Gly

<210> SEQ ID NO 22
<211> LENGTH: 17
<212> TYPE: PRT
<213> ORGANISM: Mouse
<220> FEATURE:
<223> OTHER INFORMATION: E34 CDR H2

<400> SEQUENCE: 22

Trp Ile Phe Pro Gly Asp Gly Arg Ile Lys Tyr Asn Glu Gln Ile Lys
1               5                   10                  15

Asp

<210> SEQ ID NO 23
<211> LENGTH: 34
<212> TYPE: PRT
<213> ORGANISM: Mouse
<220> FEATURE:
<223> OTHER INFORMATION: E16 FR3

<400> SEQUENCE: 23

Lys Ala Met Ala Thr Phe Thr Ala Asp Thr Ser Ser Asn Thr Ala Phe
1               5                   10                  15

Met Gln Leu Ser Ser Leu Thr Ser Glu Asp Ser Ala Val Tyr Tyr Cys
            20                  25                  30

Ala Arg

<210> SEQ ID NO 24
<211> LENGTH: 32
<212> TYPE: PRT
<213> ORGANISM: Mouse
<220> FEATURE:
<223> OTHER INFORMATION: E24 FR3

<400> SEQUENCE: 24

Lys Ala Ile Leu Thr Ala Asp Lys Ser Ser Thr Ala Tyr Met Gln
1               5                   10                  15

Leu Ser Ser Leu Thr Ser Glu Asn Ser Ala Val Tyr Phe Cys Ala Arg
            20                  25                  30

<210> SEQ ID NO 25
<211> LENGTH: 32
<212> TYPE: PRT
<213> ORGANISM: Mouse
<220> FEATURE:
<223> OTHER INFORMATION: E34 FR3
```

```
<400> SEQUENCE: 25

Lys Ala Thr Leu Thr Ala Asp Lys Ser Ser Thr Ala Tyr Met Glu
 1               5                  10                  15

Leu Ser Ser Leu Thr Ser Glu Asn Ser Ala Val Tyr Phe Cys Ala Arg
            20                  25                  30

<210> SEQ ID NO 26
<211> LENGTH: 10
<212> TYPE: PRT
<213> ORGANISM: Mouse
<220> FEATURE:
<223> OTHER INFORMATION: E16 CDR H3

<400> SEQUENCE: 26

Ser Ala Ser Tyr Gly Asp Tyr Ala Asp Tyr
 1               5                  10

<210> SEQ ID NO 27
<211> LENGTH: 10
<212> TYPE: PRT
<213> ORGANISM: Mouse
<220> FEATURE:
<223> OTHER INFORMATION: E24 CDR H3

<400> SEQUENCE: 27

Gly Gly Ser Ser Gly Thr Tyr Phe Asp Tyr
 1               5                  10

<210> SEQ ID NO 28
<211> LENGTH: 10
<212> TYPE: PRT
<213> ORGANISM: Mouse
<220> FEATURE:
<223> OTHER INFORMATION: E34 CDR H3

<400> SEQUENCE: 28

Ala Ser Tyr Tyr Gly Ser Ile Phe Asp Tyr
 1               5                  10

<210> SEQ ID NO 29
<211> LENGTH: 11
<212> TYPE: PRT
<213> ORGANISM: Mouse
<220> FEATURE:
<223> OTHER INFORMATION: E16 FR4

<400> SEQUENCE: 29

Trp Gly His Gly Thr Thr Leu Thr Val Ser Ser
 1               5                  10

<210> SEQ ID NO 30
<211> LENGTH: 11
<212> TYPE: PRT
<213> ORGANISM: Mouse
<220> FEATURE:
<223> OTHER INFORMATION: E24 and E34 FR4

<400> SEQUENCE: 30

Trp Gly Gln Gly Thr Thr Leu Thr Val Ser Ser
 1               5                  10

<210> SEQ ID NO 31
<211> LENGTH: 23
<212> TYPE: PRT
<213> ORGANISM: Mouse
```

```
<220> FEATURE:
<223> OTHER INFORMATION: E16 and E24 VL FR1

<400> SEQUENCE: 31

Asp Ile Val Met Thr Gln Ser His Lys Phe Met Ser Thr Ser Val Gly
 1               5                  10                  15

Asp Arg Val Ser Ile Thr Cys
            20

<210> SEQ ID NO 32
<211> LENGTH: 23
<212> TYPE: PRT
<213> ORGANISM: Mouse
<220> FEATURE:
<223> OTHER INFORMATION: E34 VL FR1

<400> SEQUENCE: 32

Asp Ile Val Met Thr Gln Ser His Lys Phe Met Ser Thr Ser Val Gly
 1               5                  10                  15

Asp Arg Val Asn Ile Thr Cys
            20

<210> SEQ ID NO 33
<211> LENGTH: 11
<212> TYPE: PRT
<213> ORGANISM: Mouse
<220> FEATURE:
<223> OTHER INFORMATION: E16, E24 and E34 CDR L1

<400> SEQUENCE: 33

Lys Ala Ser Gln Asp Val Ser Thr Ala Val Ala
 1               5                  10

<210> SEQ ID NO 34
<211> LENGTH: 15
<212> TYPE: PRT
<213> ORGANISM: Mouse
<220> FEATURE:
<223> OTHER INFORMATION: E16 FR2

<400> SEQUENCE: 34

Trp Tyr Gln Gln Lys Pro Gly Gln Ser Pro Lys Leu Leu Ile Ser
 1               5                  10                  15

<210> SEQ ID NO 35
<211> LENGTH: 15
<212> TYPE: PRT
<213> ORGANISM: Mouse
<220> FEATURE:
<223> OTHER INFORMATION: E24 FR2

<400> SEQUENCE: 35

Trp Tyr Gln Gln Lys Pro Gly Gln Ser Pro Lys Val Leu Ile Tyr
 1               5                  10                  15

<210> SEQ ID NO 36
<211> LENGTH: 15
<212> TYPE: PRT
<213> ORGANISM: Mouse
<220> FEATURE:
<223> OTHER INFORMATION: E34 FR2

<400> SEQUENCE: 36

Trp Tyr Gln Gln Lys Pro Gly Gln Ser Pro Lys Leu Leu Ile Tyr
 1               5                  10                  15
```

<210> SEQ ID NO 37
<211> LENGTH: 7
<212> TYPE: PRT
<213> ORGANISM: Mouse
<220> FEATURE:
<223> OTHER INFORMATION: E16, E24 and E34 CDR L2

<400> SEQUENCE: 37

Trp Ala Ser Thr Arg His Thr
 1               5

<210> SEQ ID NO 38
<211> LENGTH: 32
<212> TYPE: PRT
<213> ORGANISM: Mouse
<220> FEATURE:
<223> OTHER INFORMATION: E16 and E24 FR3

<400> SEQUENCE: 38

Gly Val Pro Asp Arg Phe Thr Gly Ser Gly Ser Gly Thr Asp Tyr Thr
 1               5                  10                  15

Leu Thr Ile Ser Ser Val Gln Ala Glu Asp Leu Ala Leu Tyr Tyr Cys
             20                  25                  30

<210> SEQ ID NO 39
<211> LENGTH: 32
<212> TYPE: PRT
<213> ORGANISM: Mouse
<220> FEATURE:
<223> OTHER INFORMATION: E34 FR3

<400> SEQUENCE: 39

Gly Val Pro Asp Arg Phe Thr Gly Ser Gly Ser Gly Thr His Tyr Thr
 1               5                  10                  15

Leu Thr Ile Ser Ser Val Gln Ala Glu Asp Leu Ala Leu Tyr Tyr Cys
             20                  25                  30

<210> SEQ ID NO 40
<211> LENGTH: 9
<212> TYPE: PRT
<213> ORGANISM: Mouse
<220> FEATURE:
<223> OTHER INFORMATION: E16 and E34 CDR L3

<400> SEQUENCE: 40

Gln Gln His Tyr Thr Thr Pro Leu Thr
 1               5

<210> SEQ ID NO 41
<211> LENGTH: 9
<212> TYPE: PRT
<213> ORGANISM: Mouse
<220> FEATURE:
<223> OTHER INFORMATION: E24 CDR L3

<400> SEQUENCE: 41

Gln Gln His Tyr Ser Asn Pro Pro Thr
 1               5

<210> SEQ ID NO 42
<211> LENGTH: 10
<212> TYPE: PRT
<213> ORGANISM: Mouse
<220> FEATURE:
<223> OTHER INFORMATION: E16 and E34 FR4

```
-continued

<400> SEQUENCE: 42

Phe Gly Ala Gly Thr Lys Leu Glu Leu Lys
1               5                   10

<210> SEQ ID NO 43
<211> LENGTH: 10
<212> TYPE: PRT
<213> ORGANISM: Mouse
<220> FEATURE:
<223> OTHER INFORMATION: E24 FR4

<400> SEQUENCE: 43

Phe Gly Gly Gly Thr Lys Leu Glu Ile Lys
1               5                   10
```